(12) United States Patent
Dearden et al.

(10) Patent No.: US 11,602,336 B2
(45) Date of Patent: Mar. 14, 2023

(54) SAMPLE RETRIEVAL TOOL WITH COMPLIANT RETENTION MEMBER

(71) Applicant: Intuitive Surgical Operations, Inc., Sunnyvale, CA (US)

(72) Inventors: Jason Dearden, Provo, UT (US); Jared Bruton, Provo, UT (US); Trent Zimmerman, American Fork, UT (US); Clayton Grames, East Palo Alto, CA (US); Amelia Mariah Parkinson, Salt Lake City, UT (US); Brian D. Jensen, Orem, UT (US); Spencer P. Magleby, Provo, UT (US); Larry L. Howell, Orem, UT (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 706 days.

(21) Appl. No.: 16/470,921

(22) PCT Filed: Dec. 15, 2017

(86) PCT No.: PCT/US2017/066748
§ 371 (c)(1),
(2) Date: Jun. 18, 2019

(87) PCT Pub. No.: WO2018/118698
PCT Pub. Date: Jun. 28, 2018

(65) Prior Publication Data
US 2020/0085415 A1    Mar. 19, 2020

Related U.S. Application Data

(60) Provisional application No. 62/436,229, filed on Dec. 19, 2016.

(51) Int. Cl.
*A61B 10/02* (2006.01)
*G01N 1/08* (2006.01)

(52) U.S. Cl.
CPC ........... *A61B 10/0275* (2013.01); *G01N 1/08* (2013.01); *A61B 2010/0208* (2013.01)

(58) Field of Classification Search
CPC ............ A61B 10/0266; A61B 10/0275; A61B 2010/0208; A61B 2017/320064
See application file for complete search history.

(56) References Cited

U.S. PATENT DOCUMENTS

| 3,140,614 A | 7/1964 | James et al. |
| 3,482,466 A | 12/1969 | Orlich et al. |

(Continued)

FOREIGN PATENT DOCUMENTS

| CN | 2626684 Y | 7/2004 |
| DE | 19537320 A1 | 4/1997 |

(Continued)

OTHER PUBLICATIONS

Choi D.Y., et al., "Flexure-Based Manipulator for Active Handheld Microsurgical Instrument," Proceedings of the IEEE 27th Annual Conference on Engineering in Medicine and Biology, Sep. 2005, pp. 5085-5088.

(Continued)

*Primary Examiner* — Sean P Dougherty

(57) ABSTRACT

The embodiments described herein can be used in a variety of sample retrieval, grasping, cutting, and manipulating operations. In some embodiments, an apparatus includes an elongated member and a retention member movably coupled to the elongated member. The elongated member includes a cutting portion configured to cut a target sample when moved, and defines an internal volume within which at least a portion of the target sample can be received. The retention member includes an engagement portion configured to move between a first position and a second position when the retention member is actuated. The engagement portion is configured to extend within the internal volume to exert a (Continued)

force on the target sample within the internal volume when the engagement portion is in the second position.

17 Claims, 26 Drawing Sheets

(56) References Cited

U.S. PATENT DOCUMENTS

| | | | |
|---|---|---|---|
| 4,165,745 A | 8/1979 | Heifetz | |
| 4,177,797 A | 12/1979 | Baylis et al. | |
| 4,262,676 A | 4/1981 | Jamshidi et al. | |
| 4,266,555 A | 5/1981 | Jamshidi et al. | |
| 4,310,969 A * | 1/1982 | Cannizzaro | A47J 25/00 |
| | | | 30/113.1 |
| 4,540,211 A | 9/1985 | Masserang | |
| 4,610,475 A | 9/1986 | Heiserman | |
| 4,781,202 A | 11/1988 | Janese | |
| 4,838,280 A | 6/1989 | Haaga | |
| 4,919,146 A | 4/1990 | Rhinehart et al. | |
| 4,986,278 A | 1/1991 | Ravid et al. | |
| 5,052,402 A | 10/1991 | Bencini et al. | |
| 5,318,589 A | 6/1994 | Lichtman | |
| 5,373,854 A | 12/1994 | Kolozsi | |
| 5,476,479 A | 12/1995 | Green et al. | |
| 5,496,317 A | 3/1996 | Goble et al. | |
| 5,511,556 A | 4/1996 | Desantis | |
| 5,560,373 A | 10/1996 | De | |
| 5,715,832 A | 2/1998 | Koblish et al. | |
| 5,827,305 A * | 10/1998 | Gordon | A61B 10/0266 |
| | | | 606/159 |
| 5,899,914 A | 5/1999 | Zirps et al. | |
| 6,068,603 A * | 5/2000 | Suzuki | A61B 10/04 |
| | | | 600/564 |
| 6,215,081 B1 | 4/2001 | Jensen et al. | |
| 6,315,737 B1 | 11/2001 | Skinner | |
| 6,368,290 B1 | 4/2002 | Baska | |
| 6,416,484 B1 | 7/2002 | Miller et al. | |
| 6,443,909 B1 | 9/2002 | Ouchi | |
| 6,551,254 B2 * | 4/2003 | Nishtalas | A61B 10/04 |
| | | | 600/567 |
| 6,623,482 B2 | 9/2003 | Pendekanti et al. | |
| 6,712,773 B1 | 3/2004 | Viola | |
| 7,131,951 B2 | 11/2006 | Angel | |
| 7,189,207 B2 | 3/2007 | Viola | |
| 7,635,340 B2 * | 12/2009 | Vetter | A61B 10/0275 |
| | | | 606/174 |
| 7,722,550 B2 * | 5/2010 | McClellan | A61B 10/0266 |
| | | | 600/564 |
| 7,758,515 B2 | 7/2010 | Hibner | |
| 7,918,804 B2 | 4/2011 | Monson et al. | |
| 8,157,744 B2 | 4/2012 | Joergensen et al. | |
| 8,187,271 B2 | 5/2012 | Yahagi et al. | |
| 8,197,419 B2 | 6/2012 | Field et al. | |
| 8,308,801 B2 | 11/2012 | Halverson et al. | |
| 8,323,297 B2 | 12/2012 | Hinman et al. | |
| 8,475,393 B1 * | 7/2013 | Hameed | A61B 10/06 |
| | | | 600/564 |
| 8,568,334 B2 | 10/2013 | Field et al. | |
| 8,597,280 B2 | 12/2013 | Cooper et al. | |
| 8,708,593 B2 | 4/2014 | Stratton et al. | |
| 8,945,174 B2 | 2/2015 | Blumenkranz et al. | |
| 9,204,867 B2 * | 12/2015 | Peliks | A61B 10/0275 |
| 9,237,883 B2 | 1/2016 | Sundheimer et al. | |
| 9,241,691 B2 * | 1/2016 | Vetter | A61B 10/0041 |
| 10,285,763 B2 | 5/2019 | Vale et al. | |
| 11,123,145 B2 | 9/2021 | Dearden et al. | |
| 11,160,540 B2 * | 11/2021 | Snow | A61B 10/0266 |
| 2005/0119527 A1 | 6/2005 | Banik et al. | |
| 2006/0184198 A1 | 8/2006 | Bales et al. | |
| 2006/0224082 A1 * | 10/2006 | Vetter | A61B 10/0233 |
| | | | 600/431 |
| 2007/0249960 A1 | 10/2007 | Williamson | |
| 2008/0196533 A1 | 8/2008 | Bergamasco et al. | |
| 2009/0198272 A1 | 8/2009 | Kerver et al. | |
| 2009/0209960 A1 | 8/2009 | Chojin | |
| 2010/0152574 A1 | 6/2010 | Erdman et al. | |
| 2010/0160735 A1 | 6/2010 | Bakos et al. | |
| 2010/0160827 A1 * | 6/2010 | Buressiniani | A61B 10/0275 |
| | | | 600/567 |
| 2010/0160940 A1 | 6/2010 | Lutze et al. | |
| 2013/0046317 A1 | 2/2013 | Blumenkranz | |
| 2016/0000423 A1 | 1/2016 | Shields et al. | |
| 2016/0015428 A1 | 1/2016 | Bowden et al. | |
| 2016/0022365 A1 | 1/2016 | Jensen et al. | |
| 2016/0045096 A1 | 2/2016 | Kappel et al. | |
| 2016/0051237 A1 | 2/2016 | Peliks et al. | |
| 2016/0051274 A1 | 2/2016 | Howell et al. | |
| 2016/0095584 A1 | 4/2016 | Almeida et al. | |
| 2016/0287279 A1 | 10/2016 | Bovay et al. | |
| 2016/0317133 A1 | 11/2016 | Orts et al. | |
| 2017/0042562 A1 | 2/2017 | Moody et al. | |
| 2018/0333164 A1 | 11/2018 | Arata et al. | |
| 2019/0290375 A1 | 9/2019 | Dearden et al. | |
| 2020/0008827 A1 | 1/2020 | Dearden et al. | |

FOREIGN PATENT DOCUMENTS

| | | |
|---|---|---|
| EP | 1151723 A2 | 11/2001 |
| WO | WO-2010078520 A2 | 7/2010 |
| WO | WO-2015057990 A1 | 4/2015 |
| WO | WO-2017189272 A1 | 11/2017 |
| WO | WO-2018052939 A1 | 3/2018 |

OTHER PUBLICATIONS

Doria M., et al., "Design of an Underactuated Compliant Gripper for Surgery Using Nitinol," Journal of Medical Devices, Mar. 2009, vol. 3 (1), Abstract, p. 011007, ASME.

Kota S. et al., "Design and Application of Compliant Mechanisms for Surgical Tools," Technical Briefs, Journal of Biomechanical Engineering, Nov. 2005, vol. 127, pp. 981-989, ASME.

Mertmann M., et al., "Grippers for the Micro Assembly Containing Shape Memory Actuators and Sensors," Le Journal de Physique IV France 7 (1997), Conference C5, Supplement of Journal de Physique III of Nov. 1997, pp. C5-621-C5-626.

Ramu G., et al., "A Flexure-based Deployable Stereo Vision Mechanism and Temperature and Force Sensors for Laparoscopic Tools," 14th National Conference on Machines and Mechanisms (NaCoMM09), Dec. 17-18, 2009, NaCoMM-2009-BMGR2, pp. 440-445.

Sahai R., et al., "Semi-Automated Micro Assembly for Rapid Prototyping of a One DOF Surgical Wrist," International Conference on Intelligent Robots and Systems (IROS 2003), Oct. 27-31, 2003, vol. 2, pp. 1882-1888, IEEE.

Zubir M.N.M., et al., "Development of a novel flexure based microgripper for precision manipulation of micro-objects," IEEE International Conference on Industrial Technology (ICIT 2009), 2009, pp. 1-6.

Edmondson B.J., et al., "Oriceps: Origami-Inspired Forceps," ASME 2013 Conference on Smart Materials, Adaptive Structures and Intelligent Systems, Sep. 16-18, 2013, 6 pages.

Essex Urology: "Prostate Template Bioposy for the Diagnosis of Prostate Cancer," 5 pages.

Guerinot A.E., et al., "Compliant Joint Design Principles for High Compressive Load Situations," Journal of Mechanical Design, Department of Mechanical Engineering, Brigham Young University, Jul. 2005, vol. 127 (4), pp. 774-781.

Halverson P.A., "Multi-stable Compliant Rolling-contact Elements," Brigham Young University, May 3, 2007, 61 pages.

International Search Report and Written Opinion for Application No. PCT/US2017/066748, dated Apr. 5, 2018, 21 pages.

Lassooij J., et al., "A Statically Balanced and Bi-stable Compliant End Effector Combined with a Laparoscopic 2DoF Robotic Arm," Journal of Mechanical Sciences. 2012, vol. 3, pp. 85-93.

Cook Medical: "Needles for Biopsy and Special Purpose," 2011, 36 pages.

(56) References Cited

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

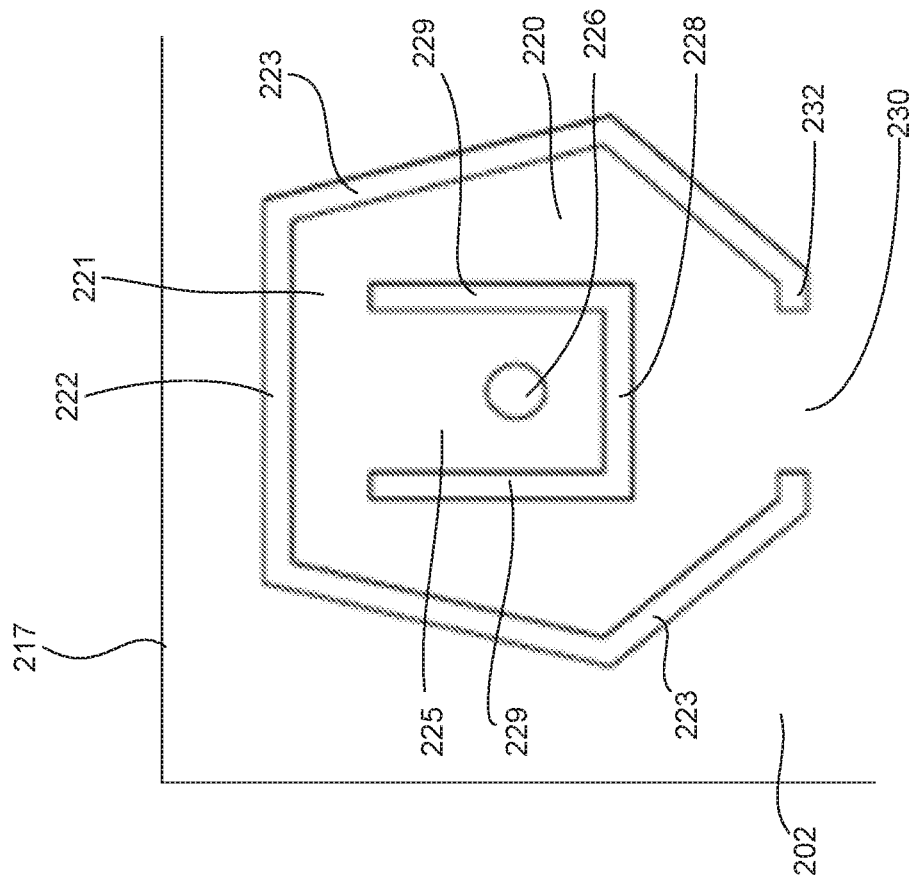
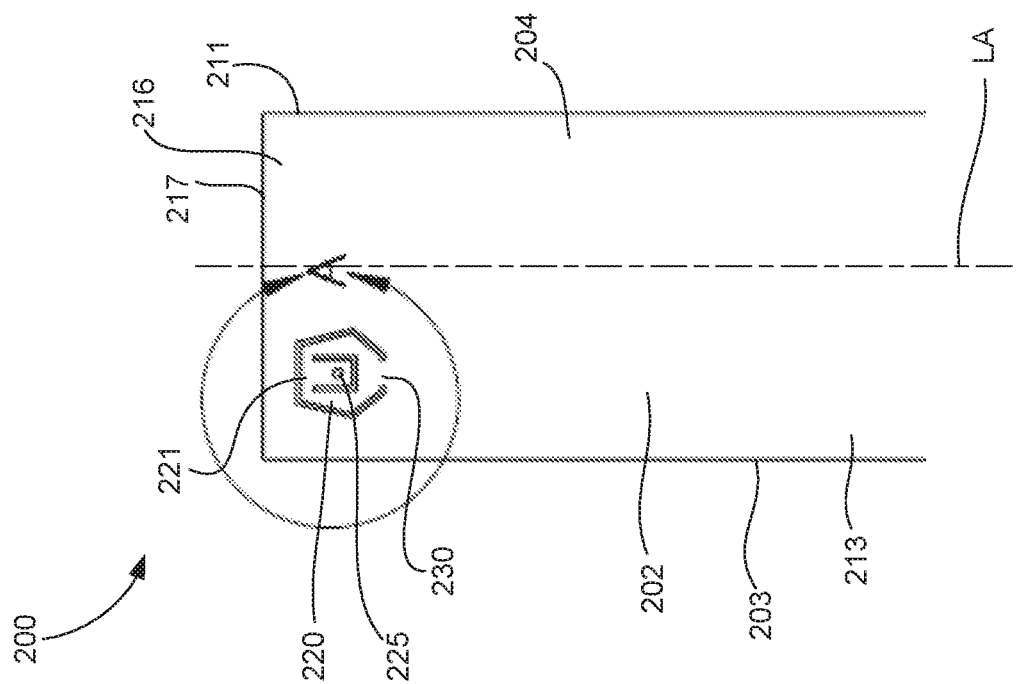

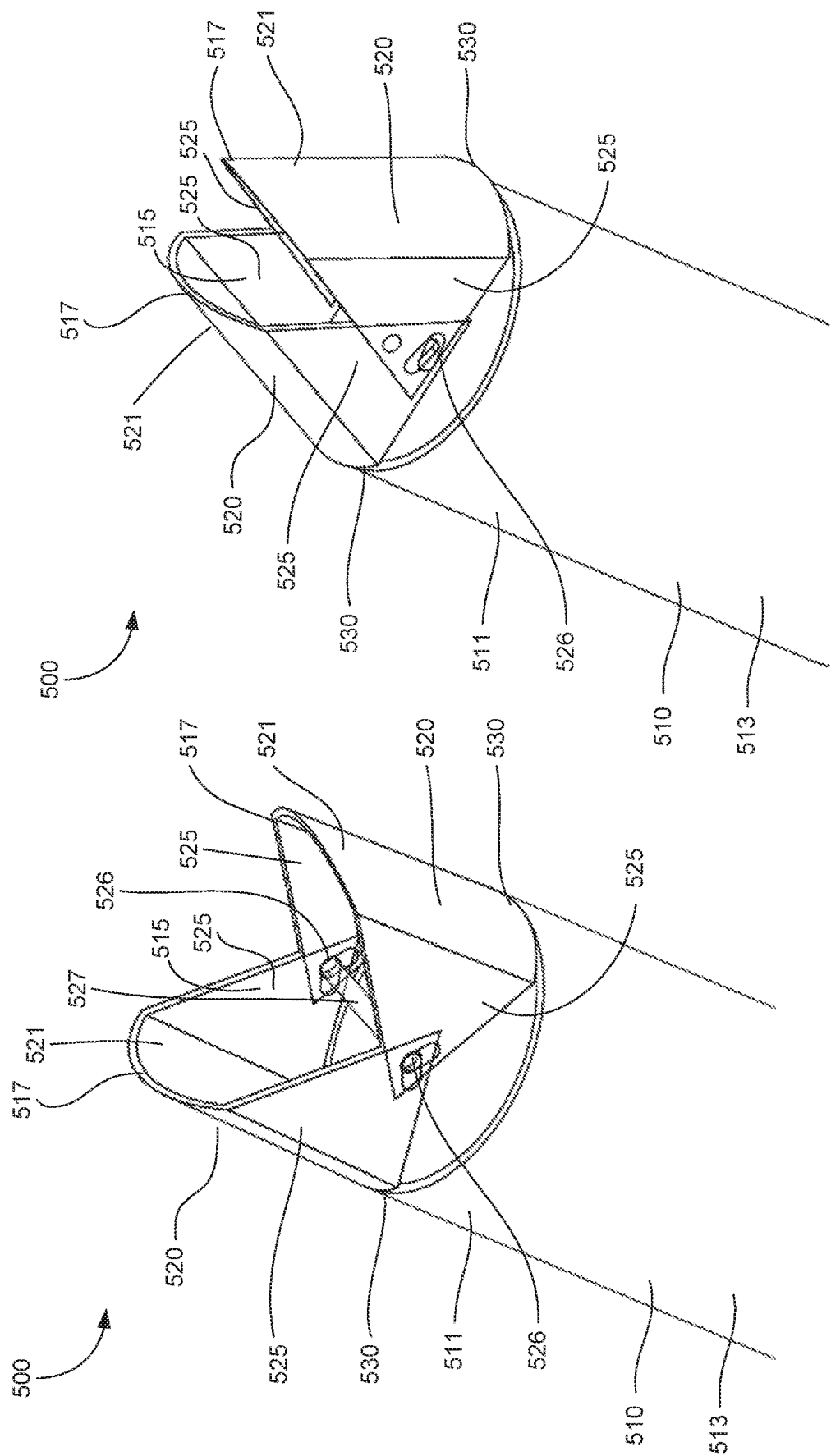

SAMPLE RETRIEVAL TOOL WITH COMPLIANT RETENTION MEMBER

CROSS-REFERENCE TO RELATED APPLICATIONS

This patent application is a U.S. national stage filing under 35 U.S.C. § 371 of International Application No. PCT/US2017/066748 (filed Dec. 15, 2017) (entitled "Sample Retrieval Tool with Compliant Retention Member"), which claims priority to and the filing date benefit of U.S. Provisional Application No. 62/436,229 (filed Dec. 19, 2016) (entitled "Sample Retrieval Tool with Compliant Retention Member"), each of which is incorporated herein by reference in its entirety.

GOVERNMENT SUPPORT

This invention was made with Government support under contracts NSF 1240417 awarded by National Science Foundation. The Government has certain rights in the invention.

BACKGROUND

The embodiments described herein relate to sample retrieval tools. More particularly, the embodiments described herein relate to sample retrieval devices having a compliant retention member that can be used, for example, in surgical applications.

Known sample retrieval tools and methods are employed to retrieve many types of samples in many different applications. Such applications include, for example, retrieving geological samples for oil and gas exploration, retrieving samples in hazardous or remote environments (e.g., during underwater or space exploration, during maintenance and repair operations involving hazardous conditions, or the like), and retrieving samples for medical purposes. For example, known biopsy procedures include retrieving a sample tissue for further testing. Known biopsy procedures are performed on many different types of tissue, including both soft tissue (e.g., breast tissue, skin tissue, or the like) and hard tissue (bone tissue).

Some known biopsy techniques are performed using a core biopsy device, which includes a cannula that is inserted into the tissue of interest. The cannula severs the tissue to produce a sample "core" that is retained within (or by) the cannula. The cannula and the retained sample are then removed from the target tissue, and the core sample is removed from the cannula for further analysis. Some known biopsy tools and methods include a multi-piece tool in which a stylet having a sample retention notch is moved within an outer cannula. In use, the stylet is extended from the cannula to expose the sample retention notch, and the cannula is subsequently moved over the stylet to cut the tissue sample and enclose the sample within the notch. Such known tools generally produce a sample having a small volume, and can be difficult to maneuver because the sample is retained in a lateral opening of the tool.

Other known biopsy tools and methods are designed to retrieve a "full" core sample, and include a multi-piece tool in which the stylet obstructs the end opening of the cannula during insertion, and is then retracted relative to the cannula to allow the core sample to extend inside of the distal end of the cannula. Thus, the core sample generally conforms to the shape and size of the cannula. Such known tools and methods, however, often rely on suction or friction forces between the sample and the cannula to retain the sample within the cannula during the withdrawal process. Moreover, such known devices often do not fully sever the distal end portion of the sample. Thus, in many instances the sample is not retained within the cannula during withdrawal. Accordingly, in an effort to retain the sample within the cannula, practitioners will often repeatedly insert and withdraw the cannula or rotate the end of the cannula to pinch the sample around and within the cannula. Such practices can result in excessive tissue damage and patient discomfort.

Some known biopsy tools include retention mechanism or mechanisms that produce a vacuum within the cannula to improve retention of the core sample therein. Such known biopsy tools, however, are complex and can be cumbersome to use.

Thus, a need exists for improved sample retrieval tools, as well as methods of assembly and use of such sample retrieval tools.

SUMMARY

This summary introduces certain aspects of the embodiments described herein to provide a basic understanding. This summary is not an extensive overview of the inventive subject matter, and it is not intended to identify key or critical elements or to delineate the scope of the inventive subject matter. In some embodiments, an apparatus includes an elongated member and a retention member movably coupled to the elongated member. The elongated member includes a cutting portion configured to cut a target sample when moved, and defines an internal volume within which at least a portion of the target sample can be received. The retention member includes an engagement portion configured to move between a first position and a second position when the retention member is actuated. The engagement portion is configured to extend within the internal volume to exert a force on the target sample within the internal volume when the engagement portion is in the second position.

In some embodiments, an apparatus includes an elongated member and a retention member. The elongated member includes a cutting portion configured to cut a target sample when the elongated member is moved. The elongated member includes a side wall defining an internal volume within which at least a portion of the target sample can be received. The retention member is monolithically constructed with and movably coupled to the elongated member. An engagement portion of the retention member moves between a first position and a second position, and is configured to exert a force on the target sample when the engagement portion is in the second position. An actuation portion of the retention member is configured to be coupled to an actuator that moves the engagement portion from the first position to the second position.

BRIEF DESCRIPTION OF THE DRAWINGS

FIG. 10 is a top view of a sample retrieval tool according to an embodiment, in a first configuration.

FIGS. 11 and 12 show an enlarged portion of the sample retrieval tool shown in FIG. 10 that is identified as the region A in FIG. 10.

FIGS. 24 and 25 are perspective views of a sample retrieval tool according to an embodiment, in a first configuration and a second configuration, respectively.

DETAILED DESCRIPTION

Figure 2:
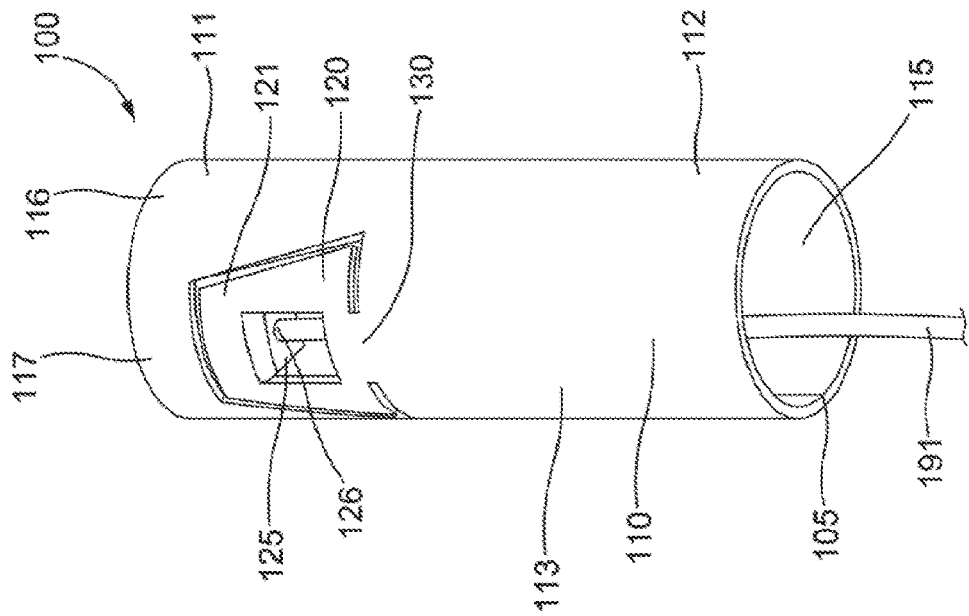
FIGS. 1 and 2 are perspective views of a sample retrieval tool according to an embodiment.

The embodiments described herein can advantageously be used in a wide variety of grasping, cutting, and manipulating operations associated with sample retrieval. In particular, the sample retrieval devices described herein can allow improved retention of the sample within the device. As described herein, the sample retrieval devices include a retention member that can be actuated to move within the sample volume defined by a cannula (or elongated member). Moreover, the retention member can be monolithically constructed with the elongated member, and in some embodiments, can include a flexure. In this manner, upon actuation, the retention member can deform to exert a retention force on the sample.

In some embodiments, an apparatus includes an elongated member and a retention member movably coupled to the elongated member. The elongated member includes a cutting portion configured to cut a target sample when moved, and defines an internal volume within which at least a portion of the target sample can be received. The retention member includes an engagement portion configured to move between a first position and a second position when the retention member is actuated. The engagement portion is configured to extend within the internal volume to exert a force on the target sample within the internal volume when the engagement portion is in the second position.

In some embodiments, an apparatus includes an elongated member and a retention member. The elongated member includes a cutting portion configured to cut a target sample when the elongated member is moved. The elongated member includes a side wall defining an internal volume within which at least a portion of the target sample can be received. The retention member is monolithically constructed with and movably coupled to the elongated member. An engagement portion of the retention member moves between a first position and a second position, and is configured to exert a force on the target sample when the engagement portion is in the second position. An actuation portion of the retention member is configured to be coupled to an actuator that moves the engagement portion from the first position to the second position.

Methods of retrieving samples are also described herein. In some embodiments, a method of retrieving a sample includes placing a distal end portion of an elongated member into contact with a target sample. The elongated member includes a side wall defining an internal volume. A cutting portion of the elongated member is moved relative to the target sample to A) cut the target sample and B) place at least a portion of the target sample within the internal volume. A retention member coupled to the elongated member is then actuated to move an engagement portion of the retention member within the internal volume thereby exerting a force on the portion of the target sample within the internal volume. The distal end portion of the elongated member is withdrawn away from the target sample.

Methods of fabricating a joint assembly are also described herein. In some embodiments, a method includes producing, in a material sheet when the material sheet is in a planar configuration, a side wall of a sample collection tool. The sample collection tool includes a retention member monolithically constructed with the side wall. The side wall defines a notch that forms a boundary of the retention member. The retention member includes an engagement portion configured to move relative to the side wall. After the producing, the material sheet is rolled such that an end portion of the side wall defines an internal volume within which at least a portion of a target sample can be received. A first side of the material sheet is then joined to a second side of the material sheet.

As used herein, the term "about" when used in connection with a referenced numeric indication means the referenced numeric indication plus or minus up to 10% of that referenced numeric indication. For example, the language "about 50" covers the range of 45 to 55. Similarly, the language "about 5" covers the range of 4.5 to 5.5.

The term "flexible" in association with a part, such as a mechanical structure, component, or component assembly, should be broadly construed. In essence, the term means the part can be repeatedly bent and restored to an original shape without harm to the part. Certain flexible components can also be resilient. For example, a component (e.g. a flexure) is said to be resilient if possesses the ability to absorb energy when it is deformed elastically, and then release the stored energy upon unloading (i.e., returning to its original state). Many "rigid" objects have a slight inherent resilient "bendiness" due to material properties, although such objects are not considered "flexible" as the term is used herein. A flexible part may have infinite degrees of freedom (DOF's).

Flexibility is an extensive property of the object being described, and thus is dependent upon the material from which the object is formed as well as certain physical characteristics of the object (e.g., cross-sectional shape, length, boundary conditions, etc.). For example, the flexibility of an object can be increased or decreased by selectively including in the object a material having a desired modulus of elasticity, flexural modulus and/or hardness. The modulus of elasticity is an intensive property of (i.e., is intrinsic to) the constituent material and describes an object's tendency to elastically (i.e., non-permanently) deform in response to an applied force. A material having a high modulus of elasticity will not deflect as much as a material having a low modulus of elasticity in the presence of an equally applied stress. Thus, the flexibility of the object can be decreased, for example, by introducing into the object and/or constructing the object of a material having a relatively high modulus of elasticity. Examples of such parts include closed, bendable tubes (made from, e.g., NITINOL®, polymer, soft rubber, and the like), helical coil springs, etc. that can be bent into various simple or compound curves, often without significant cross-sectional deformation.

Other flexible parts may approximate such an infinite-DOF part by using a series of closely spaced components that are similar to a snake-like arrangement of serial "vertebrae." In such a vertebral arrangement, each component is a short link in a kinematic chain, and movable mechanical constraints (e.g., pin hinge, cup and ball, live hinge, and the like) between each link may allow one (e.g., pitch) or two (e.g., pitch and yaw) DOFs of relative movement between the links. A short, flexible part may serve as, and be modeled as, a single mechanical constraint (a joint) that provides one or more DOF's between two links in a kinematic chain, even though the flexible part itself may be a kinematic chain made of several coupled links.

As used in this specification and the appended claims, the words "proximal" and "distal" refer to direction closer to and away from, respectively, an operator (or controller) of the surgical device. Thus, for example, the end of a retrieval tool that is farthest away from the user (and that is closest to the target tissue) would be the distal end of the retrieval tool, while the end opposite the distal end (i.e., the end manipulated by the user or coupled to the actuation shaft) would be the proximal end of the retrieval tool.

Further, specific words chosen to describe one or more embodiments and optional elements or features are not intended to limit the invention. For example, spatially relative terms—such as "beneath", "below", "lower", "above", "upper", "proximal", "distal", and the like—may be used to describe the relationship of one element or feature to another element or feature as illustrated in the figures. These spatially relative terms are intended to encompass different positions (i.e., translational placements) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the term "below" can encompass both positions and orientations of above and below. A device may be otherwise oriented (e.g., rotated 90 degrees or at other orientations) and the spatially relative descriptors used herein interpreted accordingly. Likewise, descriptions of movement along (translation) and around (rotation) various axes includes various spatial device positions and orientations. The combination of a body's position and orientation define the body's pose.

Similarly, geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

In addition, the singular forms "a", "an", and "the" are intended to include the plural forms as well, unless the context indicates otherwise. The terms "comprises", "includes", "has", and the like specify the presence of stated features, steps, operations, elements, components, etc. but do not preclude the presence or addition of one or more other features, steps, operations, elements, components, or groups.

Unless indicated otherwise, the terms apparatus, sample retrieval mechanism, sample retrieval assembly, and variants thereof, can be interchangeably used.

FIGS. 1-7 are various views of a sample retrieval assembly 100, according to an embodiment. The sample retrieval assembly 100 includes an elongated member 110 (also referred to as a cannula), a retention member 120, and an actuator 191. The sample retrieval assembly 100, and any of the sample retrieval assemblies or devices described herein, can be used in any suitable application, such as, for example, in bodily tissue retrieval procedures, geological sample retrieval procedures, part grasping procedures (e.g., during assembly of components), or the like. For example, the sample retrieval assembly 100 or any of the components therein are optionally parts of a surgical assembly that performs biopsy procedures, which can include an articulating shaft, a wrist assembly, a series of nested cannulas, or the like. Thus, the distal end portion 111 of the elongated member 110 or an end portion of the actuator 191 can be coupled to an end of a surgical instrument shaft to form a biopsy assembly.

Figure 3:
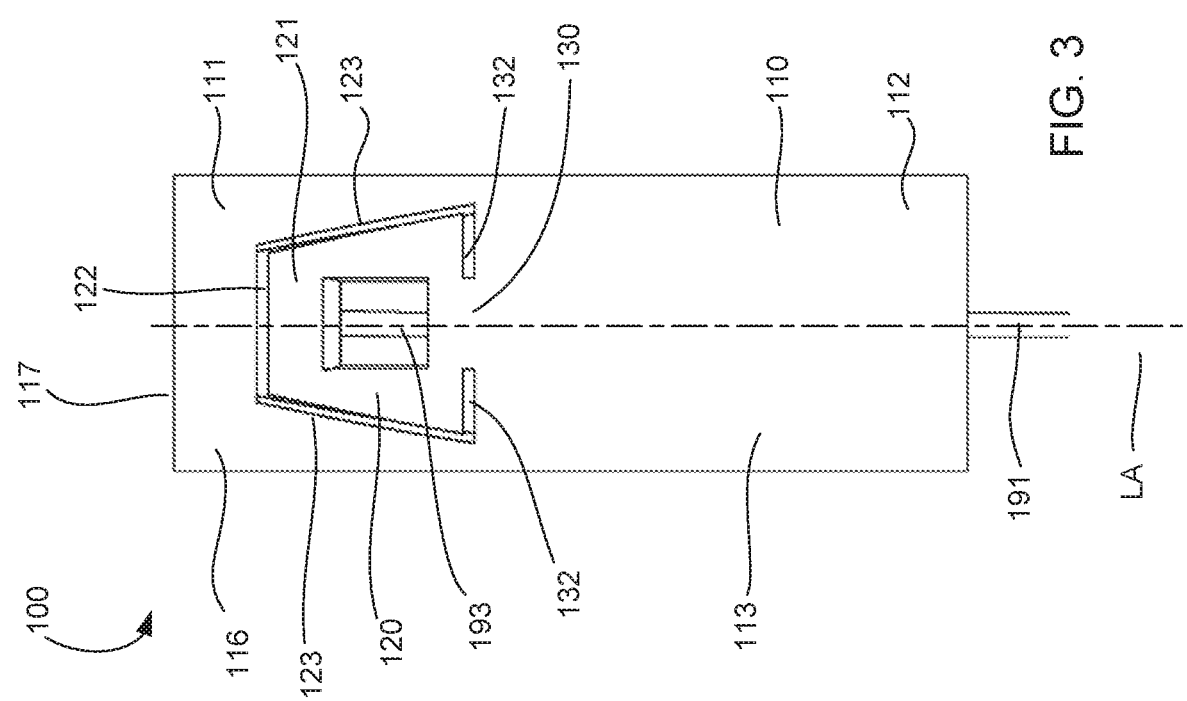
FIG. 3 is a front view of the sample retrieval tool shown in FIGS. 1 and 2.
Figure 6:
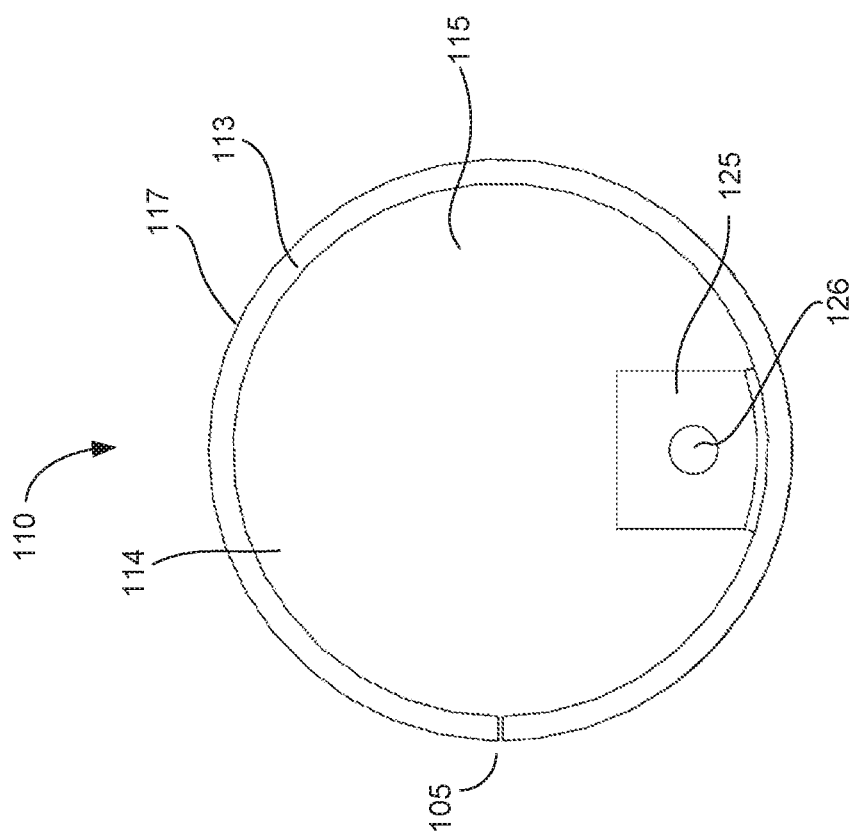
FIG. 6 is a top view of the sample retrieval tool shown in FIGS. 1 and 2.

The elongated member 110 includes a proximal end portion 112 and a distal end portion 111, and defines a longitudinal axis LA (see FIG. 3). The elongated member includes a side wall 113 that defines an internal volume 115. As described below, the internal volume 115 can receive a target sample (not shown in FIGS. 1-7). Although shown as having a cylindrical shape with the longitudinal axis LA being a longitudinal center line of the cylinder, the elongated member 110 can be any suitable shape. For example, in some embodiments, the elongated member 110 can have an elliptical, rectangular, or triangular cross-sectional shape. Said another way, in some embodiments, the cross-sectional shape of the elongated member 110 taken in a plane normal to the longitudinal axis LA need not be circular. Moreover, in some embodiments, the cross-sectional shape of the elongated member 110 can vary along the longitudinal axis LA. For example, in some embodiments, the elongated member 110, or any of the elongated members described herein, can be tapered. Specifically, in some embodiments, a size (or diameter) of the elongated member 110, or any of the elongated members described herein, can decrease from the proximal end portion 112 towards the distal end portion 111. In other embodiments, the cross-sectional size of the elongated member 110 can increase proximally to distally.

The elongated member 110 includes a cutting portion 116 configured to cut a target sample (not shown) when the elongated member is moved. Such movement can be either linear translation along the longitudinal axis LA, as shown by the arrow AA in FIG. 1, rotation about the longitudinal axis LA, as shown by the arrow BB in FIG. 1, or a combination of linear movement and rotation. As described herein, after the cutting portion 116 cuts the target sample, a portion of the cut target sample can be moved into the internal volume 115. Specifically, the distal end portion 111 defines an opening 114 in fluid communication with the internal volume 115, and through which the portion of the cut target sample can be disposed when moved into the internal volume. In this manner, the target sample is moved longitudinally, and not laterally, into the internal volume 115.

Figure 1:
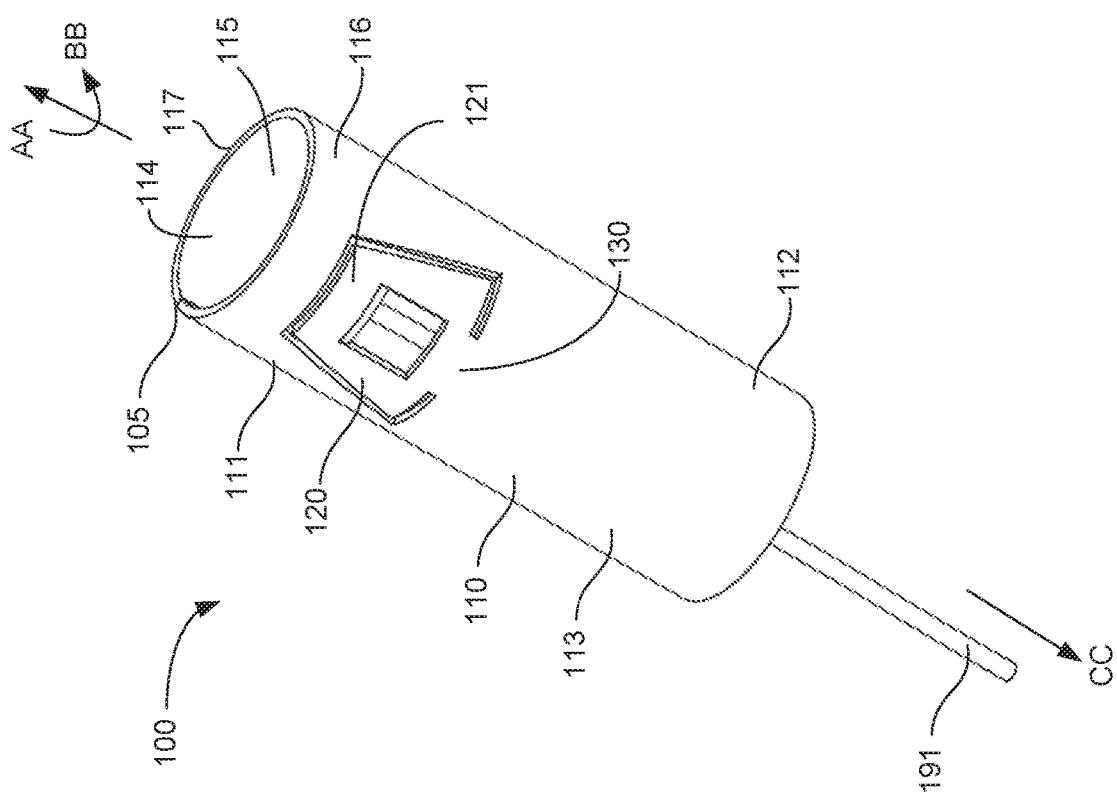

In some embodiments, the elongated member 110, and any of the elongated members described herein, can include a cutting edge at a distal-most surface of the elongated member. For example, as shown in FIG. 1, the cutting portion 116 includes a cutting edge at an end surface 117 of the elongated member 110. Specifically, the end surface 117 is the distal-most surface of the elongated member 110, and therefore defines the opening 114. Thus, as shown the cutting edge and the end surface surround the opening 114. In other embodiments, however, the cutting portion of an elongated member (including variations of the elongated member 110 or any of the elongated members described herein) can be at any suitable location along the elongated member. For example, in some embodiments, the cutting portion 116 can be located between the distal end portion 111 and the proximal end portion 112. Moreover, although the cutting edge along the end surface 117 is shown as fully surrounding the opening 114, in other embodiments, a cutting edge need only partially surround the opening 114.

The cutting edge along the end surface 117 can be any suitable structure or shape to cut, separate, perforate, dilate, or sever the target sample. For example, in some embodiments, the cutting edge can be any one of a beveled cutting edge, a serrated cutting edge, or a trephine cutting edge.

Figure 4:
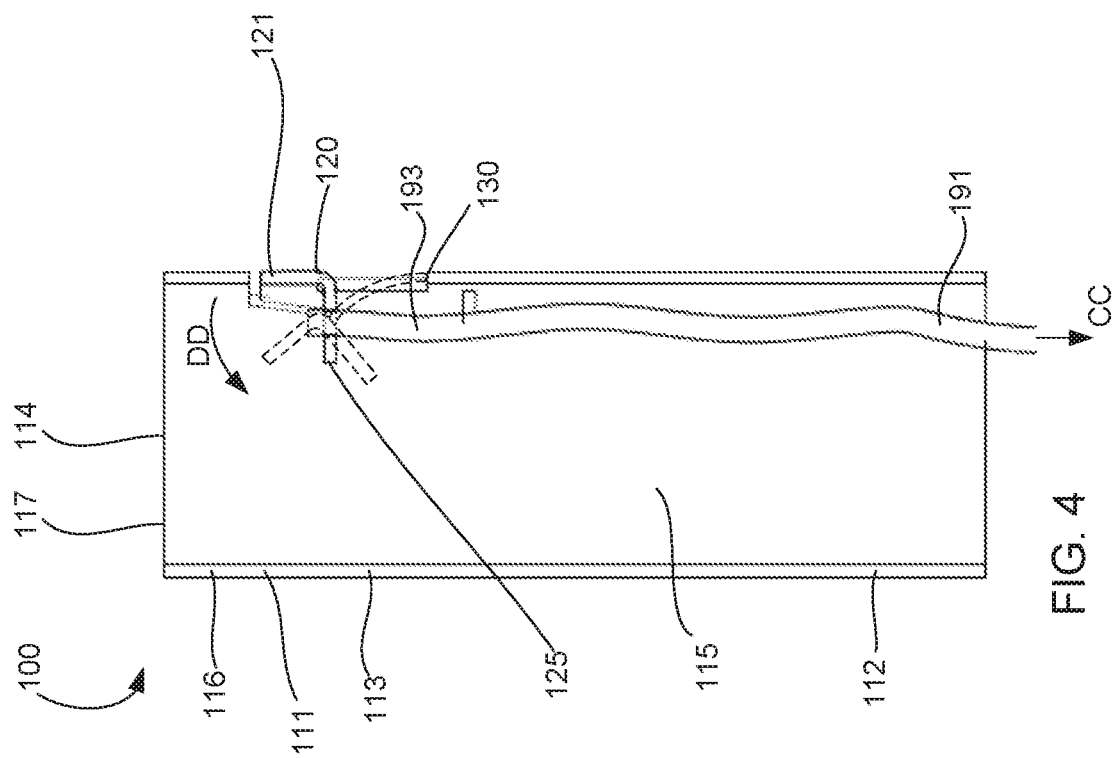
FIG. 4 is a cross-sectional view of the sample retrieval tool shown in FIGS. 1 and 2, taken along line X-X in FIG. 3.

The retention member 120 is movably coupled to the elongated member 110, and is configured to move relative to the elongated member 110 to retain the portion of the target sample within the internal volume 115. The retention member 120 includes an engagement portion 121, an actuation portion 125, and a flexure 130. As shown in FIG. 4, the actuation portion 125 is coupled to a distal end portion 193 of the actuator 191 by a coupling opening 126. In other embodiments, the actuation portion 125 can include any suitable mechanism for coupling the actuator 191 to the retention member 120.

The engagement portion 121 of the retention member 120 is configured to move between a first position (see, e.g., FIG. 4) and a second position (shown as the dashed lines in FIG. 4) when the retention member 120 is actuated. In this manner, a surface of the engagement portion 121 can exert a force (also referred to as a retention force) on the target sample within the internal volume 115 when the engagement portion 121 is in the second position. Thus, the retention member 120 is an "active" retention member, in that it is externally actuated (e.g., via the actuator 191) to exert the retention force on the target sample within the internal volume 115. More specifically, the retention member 120 and the engagement portion 121 move into the internal volume 115, as shown by the arrow DD in FIG. 4, in response to the actuator 191 being moved, as shown by the arrow CC in FIGS. 1 and 4. Similarly stated, the engagement portion 121 is aligned with the side wall 113 when the engagement portion 121 is in the first position. Said another way, when the engagement portion 121 is in the first position, a longitudinal axis of the retention member 120 is aligned with, parallel to, or coaxial with the longitudinal axis LA of the elongated member 110. In use, the engagement portion 121 rotates relative to the side wall 113 (as shown by the arrow DD) such that the engagement portion 121 is within the internal volume 115 when moved from the first position to the second position. Thus, when the engagement portion 121 is in the second position, the engagement portion is offset from the side wall 113.

The engagement portion 121 can include any surface or features that contact the target sample within the internal volume 115 to retain the target sample therein. For example, in some embodiments, the engagement portion 121 (and any of the engagement portions described herein) can include a textured surface to increase the friction between the engagement portion and the target sample to limit slipping or relative movement between the engagement portion and the target sample. In some embodiments, the engagement portion 121 (and any of the engagement portions described herein) can include a barbs, contours or other geometric features to increase contact (or friction) between the engagement portion and the target sample.

The retention member 120 is coupled to the elongated member 110 via the flexure 130 (also referred to as a living hinge). In use, the flexure 130 deforms when the retention member 120 moves relative to the elongated member 110. Similarly stated, the flexure 130 deforms when the engagement portion 121 moves from its first configuration (see, e.g., FIG. 4) to its second configuration (shown as the dashed lines in FIG. 4). In this manner, as described above, the engagement portion 121 can rotate (i.e., about a pivot axis of rotation associated with the flexure 130) relative to the side wall 113. This arrangement results in a sample retrieval assembly with low part count, reduced friction between moving parts, and the ability to scale the device to smaller sizes, as compared to a grasping mechanism that use pin joints.

In some embodiments, the flexure 130 (and any of the flexures described herein) can plastically deform when the retention member 120 is moved relative to the elongated member 110. In some such embodiments, the sample retrieval assembly 100 can be a single-use device in which the retention member 120 (and the engagement portion 121) remain in the second position even after the actuation force is released. In other embodiments, however, the flexure 130 (and any of the flexures described herein) can elastically deform, and can be repeatedly actuated. Thus, in some embodiments, the flexure 130 (and any of the flexures described herein) is a resilient member that stores energy from the actuation force and releases the energy when the actuation force is removed, thus allowing the sample retrieval assembly 100 to repeatedly be moved between the first configuration (i.e., the first position of the engagement portion 121) and the second configuration (i.e., the second position of the engagement portion 121), or any other suitable configurations.

As shown, the actuator 191 is a wire, filament, or flexible cable, the distal end portion 193 of which is attached to the actuation portion 125 of the retention member 120 via the attachment opening 126. Specifically, the actuator 191 is coupled to the actuation portion 125 such that the distal end portion 193 is within the internal volume 115. This arrangement limits contact between the movable actuator 191 and surfaces, tissue, or objects located outside of the elongated member 110. In use, the actuator 191 is moved in a proximal direction, as shown by the arrow CC in FIGS. 1 and 4, to exert the actuation force on the retention member 120, as described above. Although shown as being a flexible member, in other embodiments, the sample retrieval assembly 100 (or any of the sample retrieval assemblies described herein) can include any suitable actuator. Such actuators can include, for example, a rigid rod, a hydraulic actuator, a pneumatic actuator, or the like. In yet other embodiments, the sample retrieval assembly 100 (or any of the sample retrieval assemblies described herein) need not include an actuator. In such embodiments, for example, the practitioner can attach an actuator of their choice to the actuation portion 125 of the retention member 120.

Figure 5:
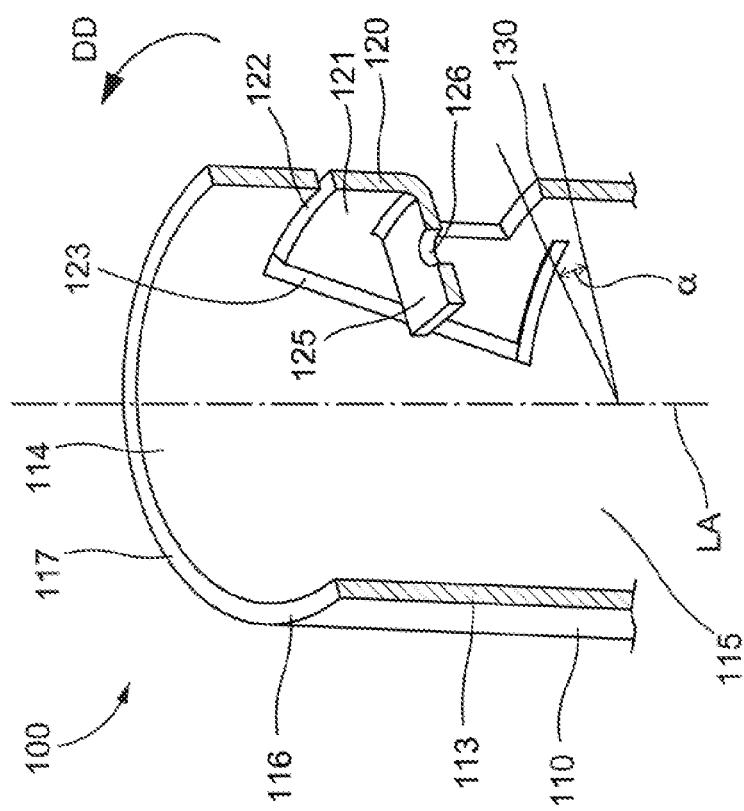
FIG. 5 is a perspective cross-sectional view of a portion of the sample retrieval tool shown in FIGS. 1 and 2, taken along line X-X in FIG. 3.
Figure 7:
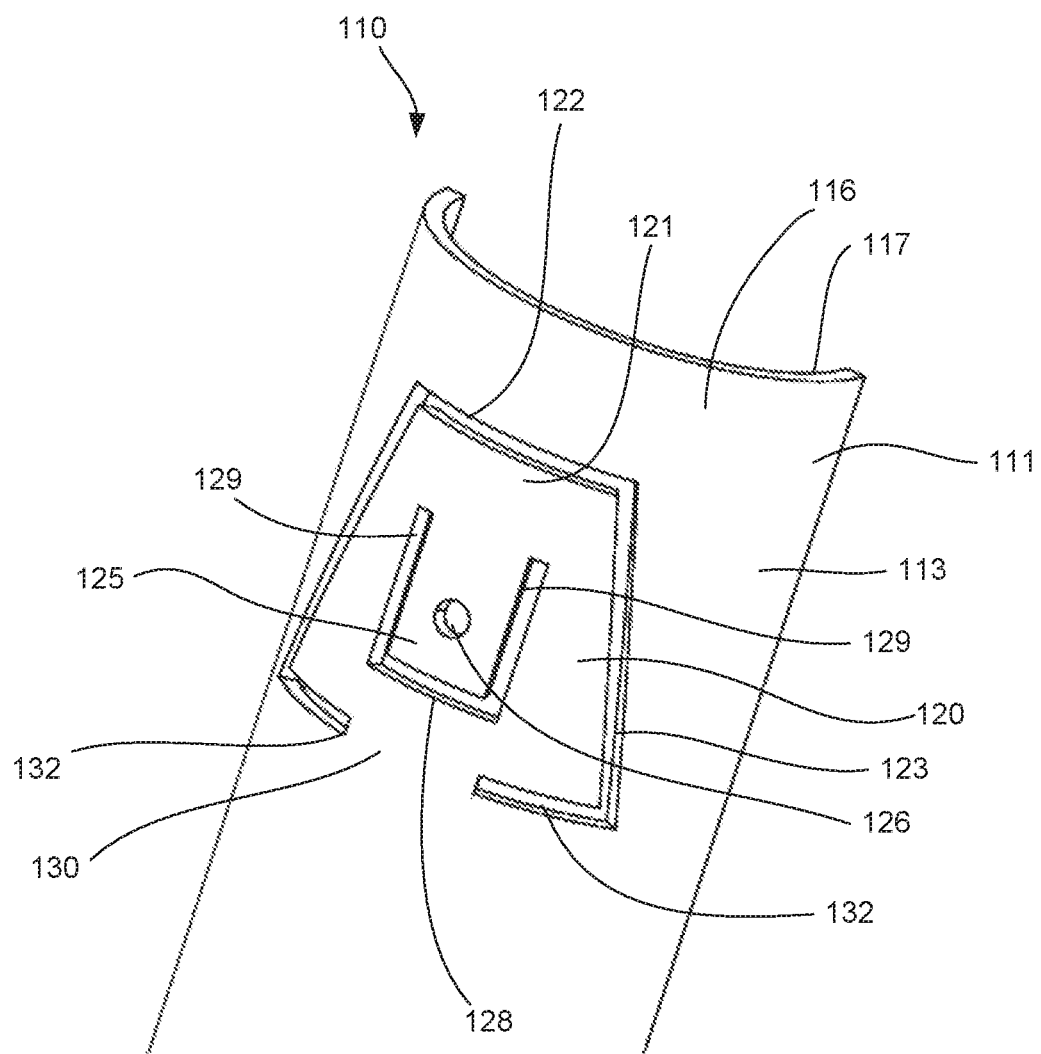
FIG. 7 is a perspective view of a portion of the sample retrieval tool shown in FIGS. 1 and 2, showing an actuation portion in a first configuration.

In some embodiments, the retention member 120 can be monolithically formed (i.e., can be integrally formed with) the elongated member 110. For example, in some embodiments, the elongated member 110 and the retention member 120 can be formed from a single material sheet according to the method 30 shown and described herein, or any or suitable methods. In some such embodiments, the material sheet can be manipulated or rolled about the longitudinal axis LA, and the edges can be joined together at a joint (see, e.g., the joint 105 in FIGS. 1 and 6) to form the internal volume 115. In such monolithically constructed designs, the side wall 113 can define a series of notches or material cut-outs to form the retention member 120, including the actuation portion 125 and the flexure 130. Specifically, the side wall 113 defines a notch or series of notches that surround a portion of the retention member 120, thereby allowing the retention member 120 to move, as described herein. Referring to FIGS. 3, 5, and 7, the side wall 113 defines a lateral notch 122 and two longitudinal notches 123 that surround a portion of the retention member 120, including the engagement portion 121.

The side wall 113 also defines two flexure notches 132 that form the flexure 130. Similarly stated, the flexure notches 132 separate the edges of the flexure 130 from the side wall 113, such that the flexure 130 can deform, as described herein. Referring to FIG. 5, the flexure notches 132 are defined such that the circumferential size of the flexure 130 (i.e., the arc of the flexure 130) has an angle (two times the angle α shown in FIG. 5, see also FIG. 8) that is within a desired range. Specifically, the angle α is within a desired range to both provide a sufficient amount of material to prevent failure of the flexure 130, while also maintaining the stiffness of the flexure 130 at a level to promote efficient and repeatable movement during actuation. For example, in some embodiments, the total arc angle (i.e., the angle about the circumference) of the flexure (i.e., the angle 2*α) is between about 20 degrees and about 40 degrees. In some embodiments, the total arc angle of the flexure (i.e., the angle 2*α) is about 30 degrees.

In considering the angle about the circumference of the flexure 130, it is noted that deflection of the flexure 130 and the stresses developed in the flexure 130 are inversely proportional to the second moment of area, I, of the flexure 130 cross-section, as shown in Eq. (1) and Eq. (2), where σ is the stress, M is the applied moment, c is the distance from the neutral axis, and I is the second moment of area. In Eq. (2), which represents the deflection of a fixed-free cantilevered beam, δ is the deflection, P is the applied load, L is the beam length, E is the modulus of elasticity, and I is the second moment of area.

$$\sigma = \frac{Mc}{I} \qquad \text{Eq. (1)}$$

$$\delta = \frac{PL^3}{3EI} \qquad \text{Eq. (2)}$$

With all other variables held constant, increasing I will result in less stress, but also less deflection for a given loading condition. If the second moment of area is doubled, the stress is reduced to half of the original value and the deflection is also reduced to half of the original value. Thus, the second moment of area was examined to determine the desired range of values for the total arc angle of the flexure 130.

Figure 8:
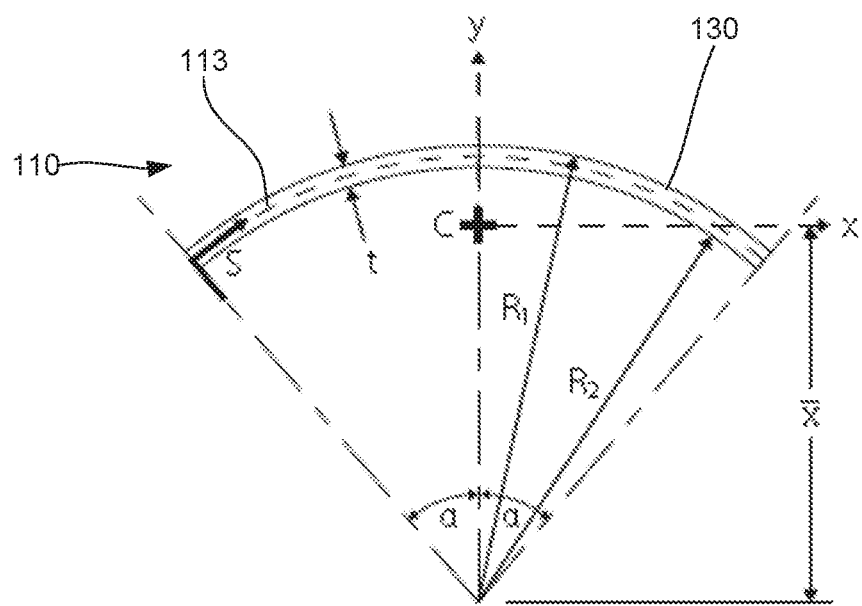
FIG. 8 is a cross-sectional view of a portion of a flexure of the sample retrieval tool shown in FIGS. 1 and 2.

For an elongated member 110 (and associated retention member 120), and any other elongated members described herein having a circular cross-sectional area, the second moment of area can be calculated at each radius about an axis through the center of curvature, as indicated by Eq. (3) and Eq. (4), below. FIG. 8 shows a schematic illustration of a cross-sectional view of the portion of the side wall 113 within which the flexure 130 is formed, and provides a listing of the variables presented in Eq. (3) and Eq. (4).

$$I_{x1} = \frac{R_1^4}{8}(2\alpha + \sin 2\alpha) \qquad \text{Eq. (3)}$$

$$I_{x2} = \frac{R_2^4}{8}(2\alpha + \sin 2\alpha) \qquad \text{Eq. (4)}$$

To find the second moment of area of a circular arc with thickness (i.e., of the flexure 130), these Eq. (3) and Eq. (4) were then subtracted to find the remaining second moment of area of the remaining material portion, as shown in Eq. (5) and Eq. (6).

$$I_x = I_{x1} - I_{x2} \qquad \text{Eq. (5):}$$

$$I_x = \frac{1}{8}(R_1^4 - R_2^4)(2\alpha + \sin 2\alpha) \qquad \text{Eq. (6):}$$

The parallel axis theorem was then used, as shown in Eq. (7) to shift the second moment of area away from the center of curvature and to the centroid to find the second moment of area about the centroid of the circular arc having a thickness. Thus, the second moment of area about the centroid is given by Eq. (8).

$$I_x = I_{\bar{x}} + Ad^2 \qquad \text{Eq. (7):}$$

$$A = \alpha(R_1^2 - R_2^2) \qquad \text{Eq. (8):}$$

To calculate $\bar{x}$, centroidal distances $\bar{x}1$ and $\bar{x}2$ were calculated, as noted in Eq. (9) and Eq. (10), below:

$$\bar{x_1} = \frac{2R_1 \sin\alpha}{3\alpha} \qquad \text{Eq. (9)}$$

$$\bar{x_2} = \frac{2R_2 \sin\alpha}{3\alpha} \qquad \text{Eq. (10)}$$

These two equations were combined using weighted areas and centroidal distances, thus resulting in Eq. (11) for the second moment of area of the cross-sectional portion of the flexure 130.

$$I_x = \frac{1}{8}(2\alpha + \sin 2\alpha)(R_1^4 - R_2^4) - \alpha(R_1^2 - R_2^2)\left(\frac{2\sin\alpha(R_1^3 - R_2^3)}{3\alpha(R_1^2 - R_2^2)}\right)^2 \qquad \text{Eq. (11)}$$

Figure 9:
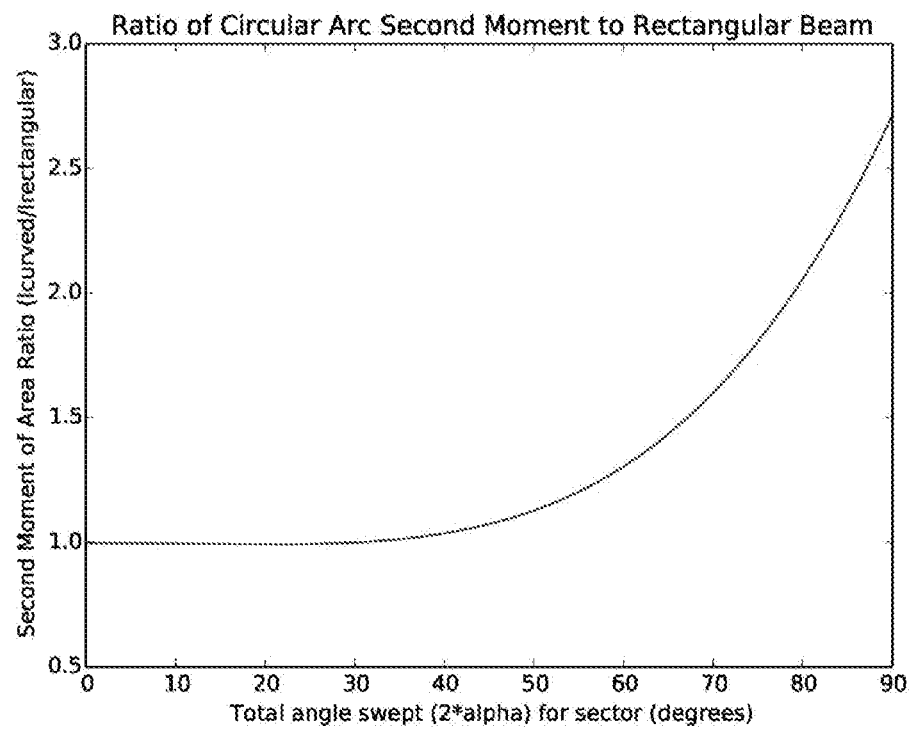
FIG. 9 is a plot of the second moment of inertia of the flexure of the sample retrieval tool shown in FIGS. 1 and 2, as a function of the swept angle of the flexure.

Based on these calculations, the second moment of area was calculated for various different values of the total angle (2*α). FIG. 9 shows a plot of the second moment of inertia of the flexure 130, as a function of the swept angle of the flexure. As shown, the second moment of area for the circular arc dramatically increases (and thus stiffness increases) when placed in bending as the total angle of the arc passes 90 degrees. Thus, in some embodiments, the total angle of the flexure 130 (i.e., the angle 2*α) is between about 20 degrees and about 40 degrees to minimize stresses during bending while also maintaining a sufficient amount of material for durability and reliability of the assembly 100.

In addition to including notches or cut-outs surrounding the engagement portion 121, the actuation portion 125 can also be monolithically constructed with the retention member 120, or the elongated member 110, or both. For example, FIG. 7 shows a portion of the elongated member 110 in a first configuration, in which the actuator 191 is not attached to the actuation portion 125. Moreover, the actuation portion 125 is in a first configuration (or position) relative to the retention member 120. Specifically, in the first configuration the actuation portion 125 is aligned with the flexure 130 and the engagement portion 121. To attach the actuator 191, the actuation portion 125 is deformed relative to the engagement portion 121. As shown in FIG. 7, the side wall 113 defines two longitudinal notches 129 and one lateral notch 128 that separate the actuation portion 125 from other portions of the retention member 120. Similarly stated, the notches 129 and the notch 128 collectively define a boundary of the actuation portion 125 of the retention member 120.

Although described as being monolithically constructed with the elongated member 110, in other embodiments, the retention member 120 (or any of retention members described herein) can be coupled to the elongated member 110 (or any of elongated members described herein) by any suitable means. For example, in some embodiments, the retention member 120 can formed separately from the elongated member 110, and later joined to the elongated member 110. For example, in some embodiments, the retention member 120 (and any of the retention members described herein) can be coupled to the elongated member 110 by welding, an adhesive bond, or the like. In other embodiments, the retention member 120 (and any of the retention members described herein) can be coupled to the elongated member 110 via mating protrusions, recesses, fasteners, or any other suitable mechanical fastening mechanism.

Figure 13:
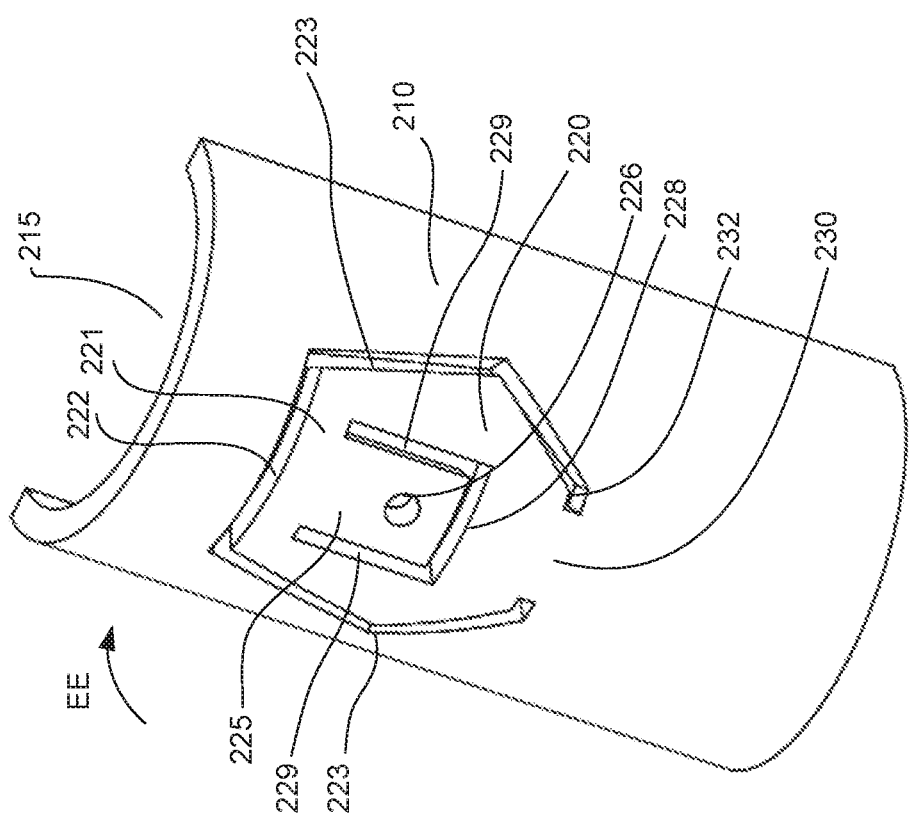
FIG. 13 is a perspective view of a portion of the sample retrieval tool shown in FIG. 10.
Figure 12:
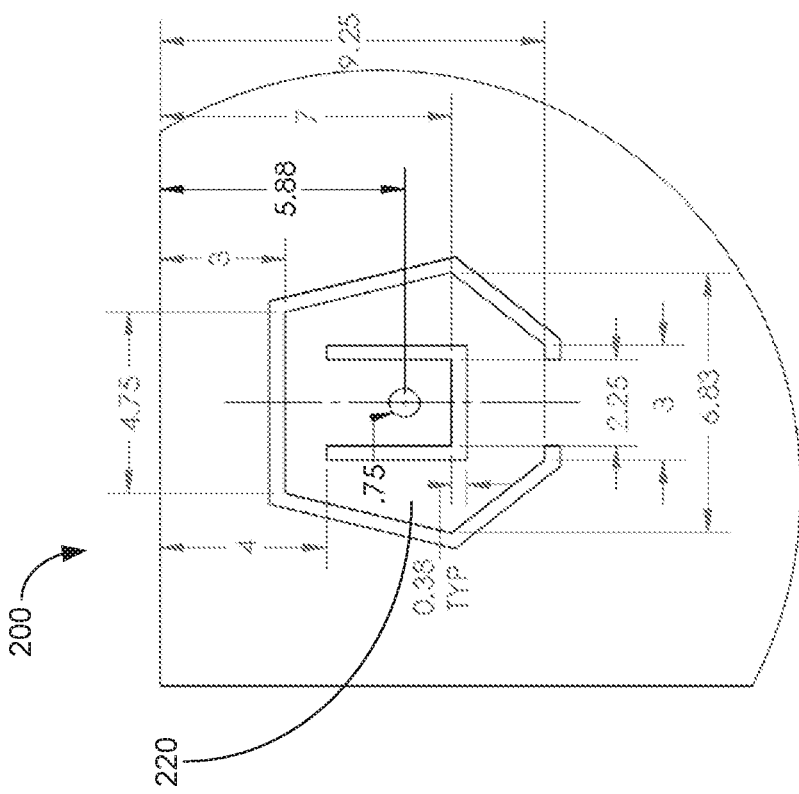

Although the engagement portion 121 is shown as including a linear engagement surface (e.g., defined by the notch 122), in other embodiments, any of the engagement portions described herein can have any suitable shape. Although the edges of the retention member 120 are shown as being linear (e.g., defined by the notes 123), in other embodiments, any of the retention members described herein can have any suitable shape. Moreover, any of the elongated members and associated retention members described herein can be monolithically formed from a single material sheet. For example, FIGS. 10-13 show various views of a sample retrieval tool 200, according to an embodiment. FIG. 10 shows a portion of the sample retrieval tool 200 in a first configuration, prior to the sample retrieval tool 200 being formed to define an internal volume 215. Specifically, FIG. 10 shows the sample retrieval tool 200 as a flat material sheet 202, prior to being formed into an elongated member 210. FIGS. 11 and 12 are enlarged views of the portion of the flat material sheet 202 identified as region A in FIG. 10. FIGS. 11 and 12 show the geometry and shape of the retention member 220, with FIG. 12 including possible dimensions (in mm) for the retention member 220. FIG. 13 shows a portion of the sample retrieval tool 200 in a second configuration, after the sample retrieval tool 200 has been formed to define an internal volume 215. As shown in FIG. 13, the actuation portion 225 of the retention member 220 is aligned with the side wall 213, and is not coupled to any actuator (e.g., the actuator 191). When formed, as shown in FIG. 13, the sample retrieval device 200 includes an elongated member 210 (also referred to as a cannula) and a retention member 220. The sample retrieval device 200, and any of the sample retrieval devices or assemblies described herein, can be used in any suitable application, such as, for example, in bodily tissue retrieval procedures, geological sample retrieval procedures, part grasping procedures (e.g., during assembly of components), or the like. For example, the sample retrieval device 200 or any of the components therein are optionally parts of a surgical assembly that performs biopsy procedures.

Figure 14:
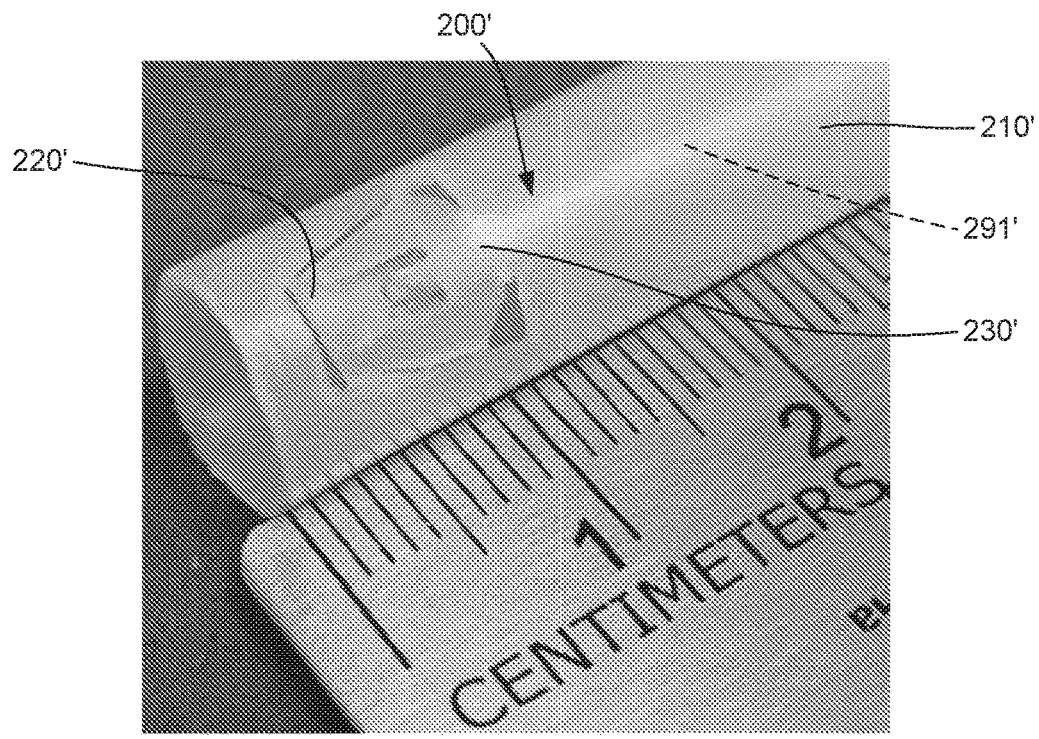
FIG. 14 is a photograph of a prototype compliant joint assembly, according to an embodiment, that corresponds to the sample retrieval tool shown in FIG. 10.

Referring to FIG. 10, the flat material sheet 202 is processed and manipulated to form a side wall 213 of the elongated member 210 (see FIG. 13). The flat material sheet 202 includes a proximal end portion, a distal end portion 211, and defines a longitudinal axis LA. Moreover, the flat material sheet 202 includes a first side edge 203 and a second side edge 204. Thus, when the material sheet 202 is manipulated to form the elongated member 210 (e.g., according to the method 30, or any other methods described herein), the first side edge 203 is joined to the second side edge 204 to form a joint (not shown in FIG. 13, but similar to the joint 105 shown and described above). In this manner, the elongated member 210 defines an internal volume 215 that can receive a target sample (not shown in FIGS. 10-14). Although FIG. 14 shows the resulting elongated member 210 as having a cylindrical shape about the longitudinal axis LA, the elongated member 210 can be any suitable shape. For example, in some embodiments, the elongated member 210 can have an elliptical, rectangular, or triangular cross-sectional shape, as described herein. Moreover, in some embodiments, the cross-sectional shape of the elongated member 210 can vary along the longitudinal axis LA. For example, in some embodiments, the elongated member 210, or any of the elongated members described herein, can be tapered, as described herein.

The elongated member 210 includes a cutting portion 216 configured to cut a target sample (not shown) when the elongated member is moved. Such movement can be either linear translation along the longitudinal axis LA, rotation about the longitudinal axis LA, or a combination of linear movement and rotation. As described herein, after the cutting portion 216 cuts the target sample, a portion of the cut target sample can be moved into the internal volume 215. In some embodiments, the elongated member 210, and any of the elongated members described herein, can include a cutting edge at a distal-most surface of the elongated member. For example, as shown in FIG. 10, the cutting portion 216 includes a cutting edge 217 at the distal-most end of the elongated member 210. In other embodiments, however, the cutting portion of an elongated member (including variations of the elongated member 210 or any of the elongated members described herein) can be at any suitable location along the elongated member. For example, in some embodiments, the cutting portion 216 can be located between the distal end portion 211 and the proximal end portion. The cutting edge along the end surface 217 can be any suitable structure or shape to cut, separate, perforate, dilate, or sever the target sample. For example, in some embodiments, the cutting edge can be any one of a beveled cutting edge, a serrated cutting edge, or a trephine cutting edge.

The retention member 220 is monolithically constructed with and movably coupled to the elongated member 210, and is configured to move relative to the elongated member 210 to retain the portion of the target sample within the internal volume 215. The retention member 220 includes an engagement portion 221, an actuation portion 225, and a flexure 230. Each of the engagement portion 221, the actuation portion 225, and the flexure 230 are monolithically constructed along with the sidewall 213 (which is formed into the elongated member 210), as described herein.

The engagement portion 221 of the retention member 220 is configured to move between a first position (FIG. 13) and a second position (not shown) when the retention member 220 is actuated. In this manner, a surface of the engagement portion 221 can exert a force (also referred to as a retention force) on the target sample when the engagement portion 221 is in the second position. Thus, the retention member 220 is an "active" retention member, in that it is externally actuated (e.g., via the actuator 291) to exert the retention force on the target sample within the internal volume 215. More specifically, in some embodiments, the retention member 220 and the engagement portion 221 moves into the internal volume 215, as shown by the arrow EE in FIG. 13, in response to movement of an actuator (not shown). Similarly stated, as shown in FIG. 13, the engagement portion 221 is aligned with the side wall 213 when the engagement portion 221 is in the first position. Said another way, when the engagement portion 221 is in the first position, a longitudinal axis of the retention member 220 is aligned with, parallel to, or coaxial with the longitudinal axis LA of the elongated member 210. When actuated, the engagement portion 221 rotates relative to the side wall 213 (as shown by the arrow EE) to engage the tissue sample. In some embodiments, the engagement portion 221 is within the internal volume 215 when moved from the first position to the second position. Thus, when the engagement portion 221 is in the second position, the engagement portion is offset from the side wall 213. In other embodiments, however, the engagement portion 221 can engage the tissue sample while remaining outside of the internal volume 215.

The engagement portion 221 can include any surface or features that contact the target sample within the internal volume 215 to retain the target sample therein. For example, in some embodiments, the engagement portion 221 (and any of the engagement portions described herein) can include a textured surface to increase the friction between the engagement portion and the target sample to limit slipping or relative movement between the engagement portion and the target sample. In some embodiments, the engagement portion 221 (and any of the engagement portions described herein) can include a barbs, contours or other geometric features to increase contact (or friction) between the engagement portion and the target sample.

The retention member 220 is coupled to the elongated member 210 via the flexure 230 (also referred to as a living hinge). In use, the flexure 230 deforms when the retention member 220 moves relative to the elongated member 210. Similarly stated, the flexure 230 deforms when the engagement portion 221 moves from its first configuration (see, e.g., FIG. 13) to its second configuration (not shown). In this manner, as described above, the engagement portion 221 can rotate (i.e., about a pivot axis of rotation associated with the flexure 230) relative to the side wall 213. This arrangement results in a sample retrieval assembly with low part count, reduced friction between moving parts, and the ability to scale the device to smaller sizes, as compared to a grasping mechanism that use pin joints.

As stated above, the retention member 220 is monolithically formed (integrally formed) with the elongated member 210 in the material sheet 202. Thus, referring to FIG. 11, the side wall 213 defines a series of notches or material cut-outs to form the retention member 220, including the engagement portion 221, the actuation portion 225, and the flexure 230. Specifically, the side wall 213 defines a notch or series of notches that surround a portion of the retention member 220, thereby allowing the retention member 220 to move, as described herein. In particular, the side wall 213 defines a lateral notch 222 and two longitudinal notches 223 that surround a portion of the retention member 220. In contrast to the longitudinal notches 123 described above with reference to the elongated member 110, the longitudinal notches 223 are discontinuous (i.e., they do not follow a single line or curve), and form a retention member 220 having tapered sides.

The side wall 213 also defines two flexure notches 232 that form the flexure 230. Similarly stated, the flexure notches 232 separate the edges of the flexure 230 from the side wall 213, such that the flexure 230 can deform, as described herein. The flexure notches 232 are defined such that the circumferential size of the flexure 230 (i.e., the arc of the flexure 230) has an angle that is within a desired range. Specifically, the angle (not identified, but similar to the angle α described above with respect to the flexure 130) is within a desired range to both provide a sufficient amount of material to prevent failure of the flexure 230, while also maintaining the stiffness of the flexure 230 at a level to promote efficient and repeatable movement during actuation. For example, in some embodiments, the total arc of the flexure is between about 20 degrees and about 40 degrees. In some embodiments, the total arc of the flexure is about 30 degrees.

In some embodiments, the flexure 230 (and any of the flexures described herein) can plastically deform when the retention member 220 is moved relative to the elongated member 210. In some such embodiments, the sample retrieval device 200 can be a single-use device in which the retention member 220 (and the engagement portion 221) remain in the second position even after any applied actuation force is released. In other embodiments, however, the flexure 230 (and any of the flexures described herein) can elastically deform, and can be repeatedly actuated. Thus, in some embodiments, the flexure 230 (and any of the flexures described herein) is a resilient member that stores energy from the actuation force and releases the energy when the actuation force is removed, thus allowing the sample retrieval device 200 to repeatedly actuated.

As shown in FIG. 11, the actuation portion 225 includes a coupling opening 226 to which an actuator (not shown, but which can be any actuator of the types shown and described herein, including the actuator 191) can be coupled. In other embodiments, however, the actuation portion 225 can include any other suitable mechanism for coupling the actuator to the retention member 220. Such coupling mechanisms can include, for example, notches, clips, protrusions, or the like. The actuation portion 225 is also be monolithically constructed with the retention member 220. Specifically, FIGS. 10-13 show the actuation portion 225 is in a first configuration (or position) relative to the retention member 220, in which the actuation portion 225 is aligned with the flexure 230 and the engagement portion 221. The side wall 213 defines two longitudinal notches 229 and one lateral notch 228 that separate the actuation portion 225 from other portions of the retention member 220. Similarly stated, the notches 229 and the notch 228 collectively define a boundary of the actuation portion 225 of the retention member 220. To attach an actuator to the actuation portion 225, the actuation portion 225 is deformed relative to the engagement portion 221, and the actuator (not shown) is coupled within the opening 226.

Any of the sample retrieval assemblies or devices described herein can be used in any suitable sample retrieval application, such as, for example, bodily tissue retrieval procedures, geological sample retrieval procedures, part grasping procedures (e.g., during assembly of components), or the like. For example, the sample retrieval assemblies or any of the components therein can be used to perform a biopsy procedure. Procedures for using any of the devices described herein are described with respect to the devices shown in FIGS. 14-17, and the flow chart in FIG. 18. The methods described herein, however, can be used with any of the devices shown and described herein. Specifically, FIG. 14 is a photograph of a large-scale prototype sample retrieval assembly 200'. The prototype sample retrieval assembly 200' is similar in design to the sample retrieval device 200 described above, and is therefore not described in detail here. The sample retrieval device 200' was constructed from Nylon 6/6 tubing (having an outer diameter of 9.525 mm and a wall thickness of 0.794 mm), rather than from a flat material sheet (as shown above for the device 200).

As shown, the sample retrieval assembly 200' includes an elongated member 210' (also referred to as a cannula), a retention member 220', and an actuator 291'. The elongated member 210' defines an internal volume 215' that can receive a portion of a target sample S (see FIGS. 16 and 17). The elongated member 210' includes a cutting portion 216' that is similar to the cutting portions 116 and 216, and is configured to cut the target sample S when the elongated member is moved. As shown the cutting portion 216' includes a cutting edge at the end surface of the elongated member 210'.

The retention member 220' is similar to the retention member 220 described above, and is configured to move relative to the elongated member 210' to retain the portion of the target sample S within the internal volume 215'. The retention member 220' includes an engagement portion (similar to the engagement portion 221), an actuation portion (similar to the actuation portion 225, and a flexure 230' (similar to the flexure 230). As shown, the actuation portion is coupled to an actuator 291'.

Figure 15:
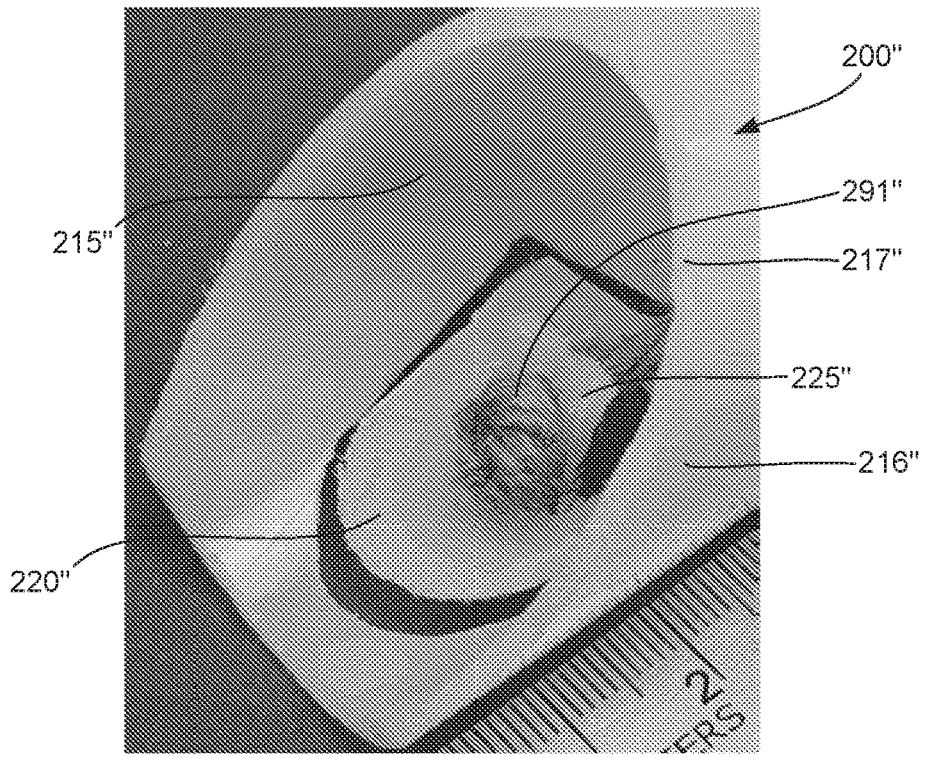
FIG. 15 is a photograph of a prototype compliant joint assembly, according to an embodiment.

Although the cutting portion 216' (and the cutting portion 216) are shown as having a flat end surface (i.e., an end surface that is normal to the longitudinal axis of the elongated member), in other embodiments, an elongated member can include an end surface that is tapered with respect to the longitudinal axis. For example, FIG. 15 is a photograph of a large-scale prototype sample retrieval assembly 200". The prototype sample retrieval assembly 200" is similar in design to the sample retrieval device 200 and the retrieval device 200' described above, and is therefore not described in detail herein. As shown, the sample retrieval assembly 200" includes an elongated member 210" (also referred to as a cannula), a retention member 220", and an actuator 291". The elongated member 210" defines an internal volume 215" that can receive a portion of a target sample S (see FIGS. 16 and 17). The elongated member 210" includes a cutting portion 216" that is similar to the cutting portions 116 and 216, and is configured to cut the target sample S when the elongated member is moved. As shown the cutting portion 216" includes a tapered cutting edge 217" at the end surface of the elongated member 210".

Figure 17:
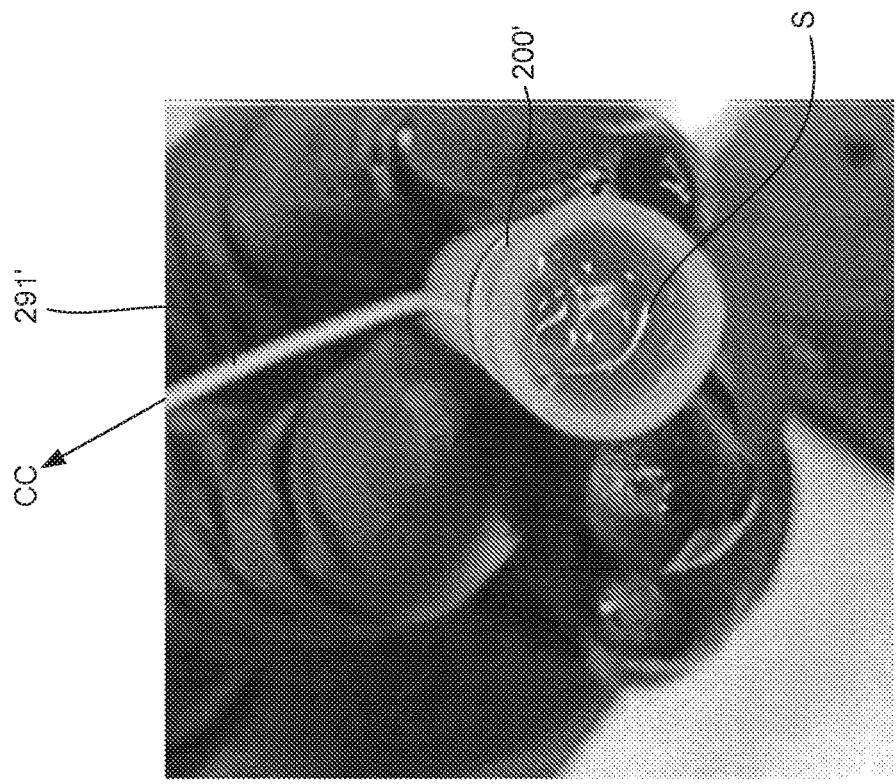
FIGS. 16 and 17 are photographs showing the operation of the prototype compliant joint assembly shown in FIG. 14.
Figure 18:
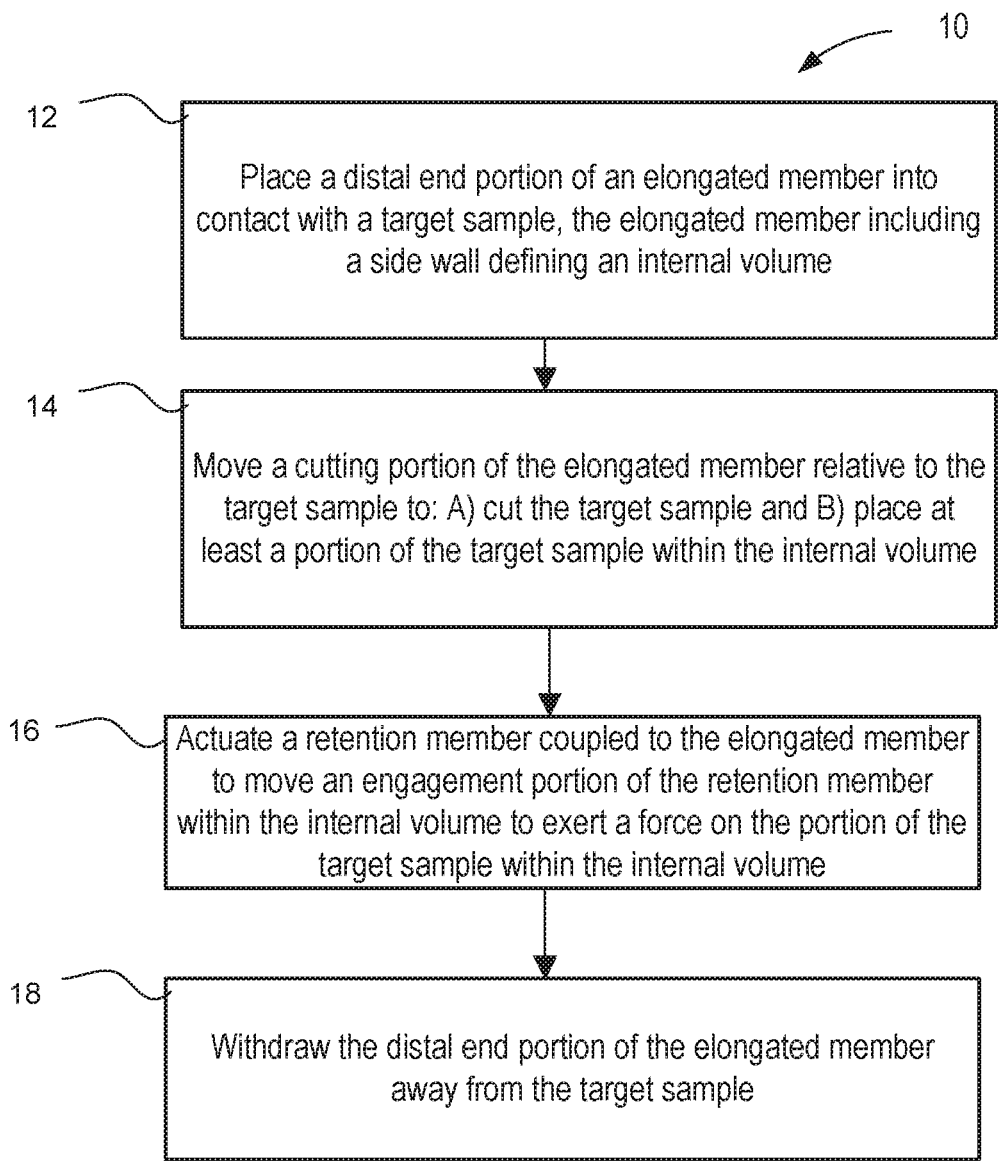
FIG. 18 is a flow diagram of a method of retrieving a sample, according to an embodiment.

Any of the sample retrieval assemblies or devices described herein can be used in any suitable sample retrieval application. FIG. 18 is a flow chart of a method 10 of retrieving a sample, according to an embodiment. The method includes placing a distal end portion of an elongated member (also referred to as a cannula) into contact with a target sample, at 12. The target sample can be any suitable target sample, such as the tissue sample S shown in FIGS. 16 and 17. In other embodiments, the target sample can be a geological sample, a food sample, a manufactured product, or the like. The elongated member can be any of the elongated members or cannulas described herein, and includes a side wall (such as the side wall 213 described above) defining an internal volume (such as the internal volume 215 or 215' described above).

Figure 16:
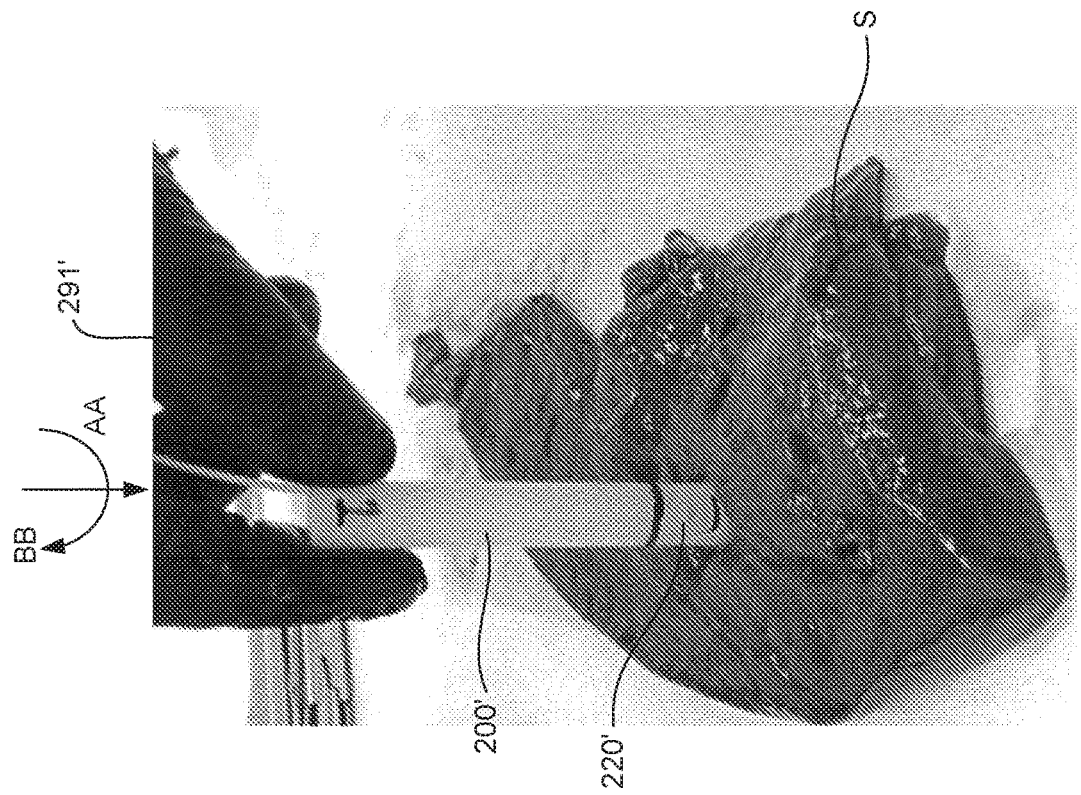

A cutting portion of the elongated member is moved relative to the target sample to A) cut the target sample and B) place at least a portion of the target sample within the internal volume, at 14. The cutting portion can be any cutting portion of the types shown and described herein, such as, for example, the cutting portion 216 or 216'. Referring to FIG. 16, the elongated member can be moved in any suitable manner, such as linear movement along the longitudinal axis of the elongated member (as shown by the arrow AA in FIG. 16), rotation of the elongated member about the longitudinal axis (as shown by the arrow BB in FIG. 16), or both. As shown in FIG. 17, the moving results in a portion of the cut sample S being placed into the internal volume of the elongated member via a distal end opening (i.e., similar to the opening 114 or 214 shown and described above).

A retention member coupled to the elongated member is then actuated to move an engagement portion of the retention member within the internal volume to exert a force on the portion of the target sample within the internal volume, at 16. In this manner, the portion of the sample (e.g., the tissue core sample) is retained within the internal volume, as shown in FIG. 17. The retention member can be any of the retention members described herein, such as, for example, the retention member 120 or the retention member 220. In some embodiments, the retention member includes a flexure that is deformed to move the engagement portion when the retention member is actuated. In some embodiments, the flexure, the retention member, and the side wall can be monolithically constructed, as described above with reference to the sample retrieval device 200. In other embodiments, however, the retention member can be separately constructed from, and then later attached to, the elongated member.

The retention member can be actuated by any of the methods and via any of the structures or components described herein. For example, in some embodiments, the retention member can be actuated by the exertion of a proximal force on a cable or flexible member attached to the actuation portion of the retention member. The actuator (or cable) can be similar to the actuator 191 or the actuator 291' shown and described herein. In other embodiments, the actuator can be external to (i.e., on the outside of) the elongated member. In yet other embodiments, the actuator can be a rigid member.

The distal end portion of the elongated member is then withdrawn away from the target sample, 18.

Figure 19:
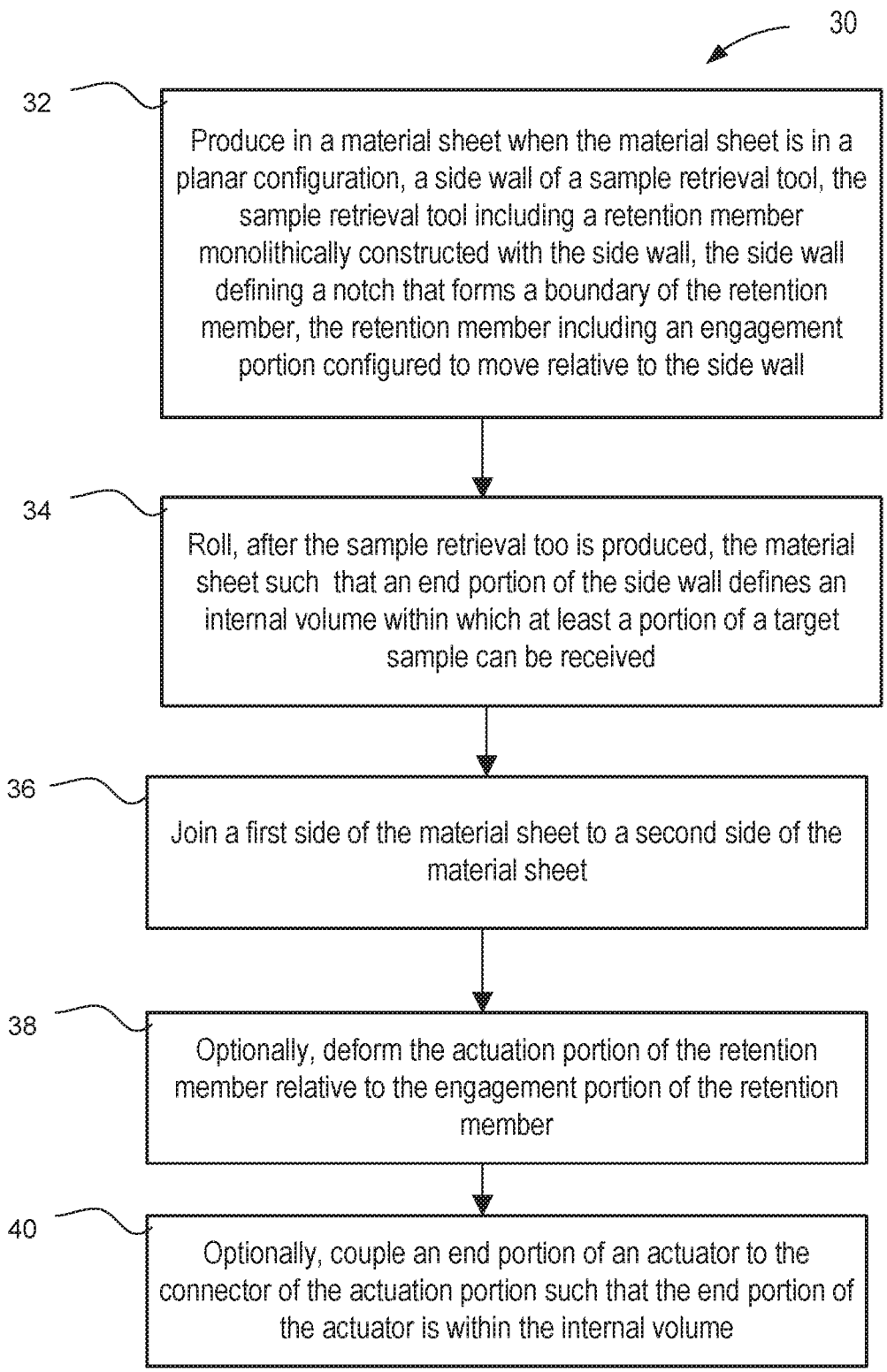
FIG. 19 is a flow diagram of a method of fabricating a sample retrieval tool, according to an embodiment.

As described above with respect to the retrieval device 200, any of the sample retrieval devices, can be monolithically constructed from a material sheet. For example, FIG. 19 is a flow chart of a method 30 of producing a sample retrieval tool, according to an embodiment. The method 30 can be performed to produce any of the devices, joint assemblies, or components thereof described herein. The method 30 includes producing, in a material sheet when the material sheet is in a planar configuration, a side wall of a sample retrieval tool, at 32. The sample retrieval tool includes a retention member monolithically constructed with the side wall, and the side wall defines a notch that forms a boundary of the retention member. The retention member includes an engagement portion configured to move relative to the side wall. The sample retrieval tool can be any of the sample retrieval tools described herein, such as, for example, the sample retrieval tool 100 or the sample retrieval tool 200. In some embodiments, the notch is defined by removing material from the material sheet. The material can be removed by any suitable method, such as, for example, electrical discharge machining (EDM), laser-cutting, waterjet, and traditional machining.

The method further includes rolling, after the producing, the material sheet such that such that an end portion of the side wall defines an internal volume within which at least a portion of a target sample can be received, at 34. In some embodiments, the rolling includes forming a cylinder that defines the internal volume. A first side of the material sheet is then joined to a second side of the material sheet, at 36. The sides of the material sheet can be joined using any suitable method, such as via welding, forming an adhesive bond, or the like.

In some embodiments, the method 30 optionally includes deforming the actuation portion of the retention member relative to the engagement portion of the retention member, at 38. In this manner, the actuation portion can be configured for being coupled to an actuator (such as the actuator 191 described above). In some embodiments, the method 30 optionally includes coupling an end portion of an actuator to the connector of the actuation portion such that the end portion of the actuator is within the internal volume, at 40.

Figure 21:
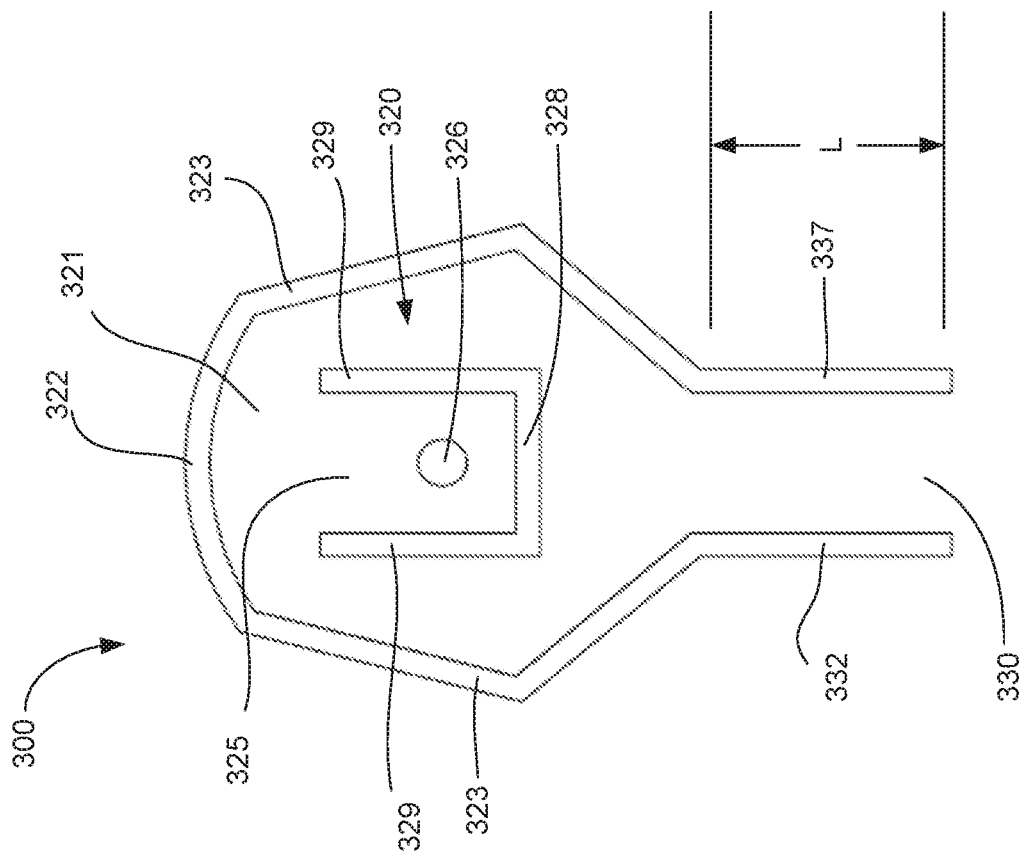
FIG. 21 is a front view of a portion of the sample retrieval tool shown in FIG. 21.
Figure 20:
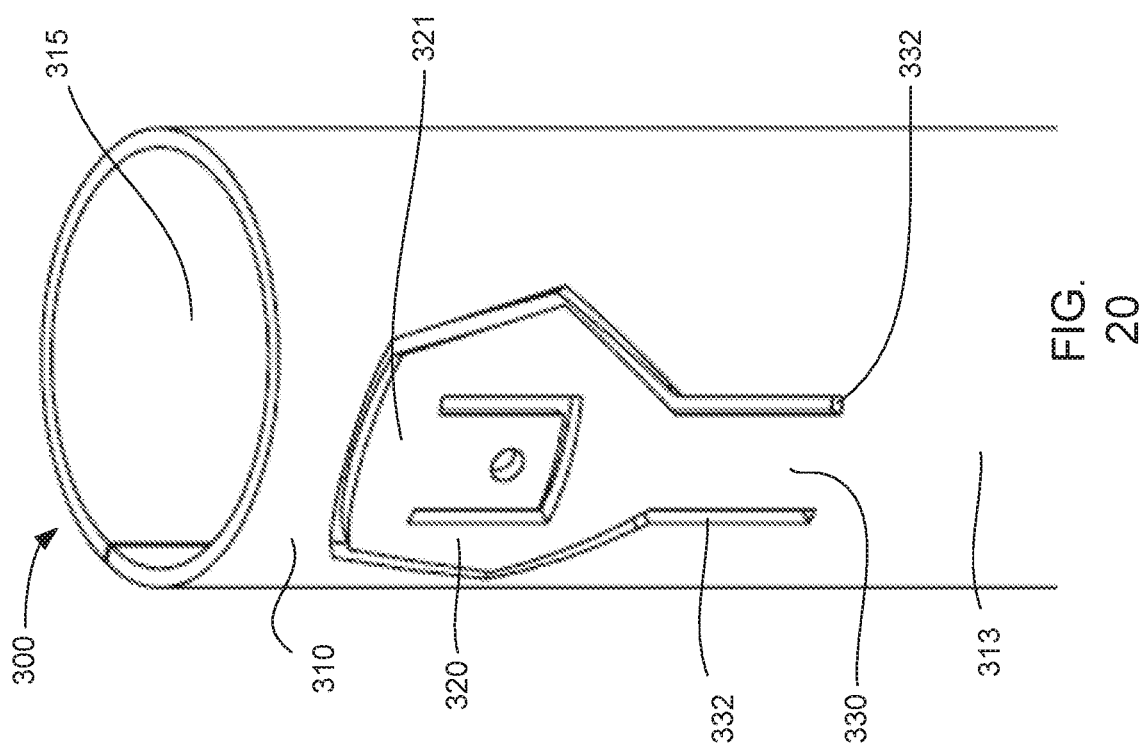
FIG. 20 is a perspective view of a sample retrieval tool according to an embodiment, in a first configuration.

In some embodiments, a sample retrieval tool can include a flexure sized, shaped, and configured to deform in any suitable manner to move (or control the movement of) an engagement portion of a retention member. For example, in some embodiments, such as that shown above with respect to the flexure 130, a flexure can have a short length (i.e., a short distance along the longitudinal axis). Such configurations can be suitable for plastic deformation of the flexure, and thus the associated sample retrieval tool may be configured as a single-use device. In other embodiments, however, a flexure can be configured to elastically deform, and thus can be repeatedly actuated. For example, in some embodiments, a flexure can have a longer length than that shown for the flexure 130. As one example, FIGS. 20 and 21 show various views of a sample retrieval tool 300, according to an embodiment. FIG. 20 shows a portion of the sample retrieval tool 300 after it has been formed to define an internal volume 315. FIG. 21 is an enlarged view showing the shape and geometry of the retention member 320 and the flexure 330 when the sample retrieval tool 300 is in a flat configuration (i.e., prior to having been formed, as shown in FIG. 20). Moreover, both FIGS. 20 and 21 show the actuation portion 325 of the retention member 320 being aligned with the side wall 313, and not coupled to any actuator (e.g., the actuator 191). The sample retrieval device 300 includes an elongated member 310 (also referred to as a cannula) having a side wall 313 that defines the internal volume 315 within which a target sample (not shown) can be received. The sample retrieval device also includes a retention member 320. The sample retrieval device 300, and any of the sample retrieval devices or assemblies described herein, can be used in any suitable application, such as, for example, in bodily tissue retrieval procedures, geological sample retrieval procedures, part grasping procedures (e.g., during assembly of components), or the like. For example, the sample retrieval device 300 or any of the components therein are optionally parts of a surgical assembly that performs biopsy procedures.

The sample retrieval device 300 can be formed from a flat material sheet 302 to form a side wall 313 of the elongated member 310, as described above. Moreover, although FIG. 20 shows the resulting elongated member 310 as having a cylindrical shape about the longitudinal axis LA, the elongated member 310 can be any suitable shape. For example, in some embodiments, the elongated member 310 can have an elliptical, rectangular, or triangular cross-sectional shape, as described herein. The elongated member 310 is similar to the elongated member 110 and the elongated member 210 described above, and is thus not described in detail herein. For example, the elongated member 310 includes a cutting portion configured to cut a target sample when the elongated member is moved, similar to the cutting portions 116 and 216 described above. The elongated member 310 can also be coupled to an actuator, similar to the actuator 191 described above, to actuate the retention member 320.

The retention member 320 is movably coupled to the elongated member 310, and is configured to move relative to the elongated member 310 to retain the portion of the target sample within the internal volume 315. The retention member 320 includes an engagement portion 321, an actuation portion 325, and a flexure 330. The engagement portion 321 of the retention member 320 is configured to move between a first position (FIG. 20) and a second position (not shown) when the retention member 320 is actuated. In this manner, a surface of the engagement portion 321 can exert a force (also referred to as a retention force) on the target sample when the engagement portion 321 is in the second position.

Thus, the retention member 320 is an "active" retention member, in that it is externally actuated (e.g., via an actuator, not shown) to exert the retention force on the target sample within the internal volume 315. More specifically, in some embodiments, the retention member 320 and the engagement portion 321 move into the internal volume 315 when actuated. Similarly stated, as shown in FIG. 20, the engagement portion 321 is aligned with the side wall 313 when the engagement portion 321 is in the first position. Said another way, when the engagement portion 321 is in the first position, a longitudinal axis of the retention member 320 is aligned with, parallel to, or coaxial with the longitudinal axis LA of the elongated member 310. When actuated, the engagement portion 321 rotates relative to the side wall 313 to engage the tissue sample. In some embodiments, the engagement portion 321 is within the internal volume 315 when moved from the first position to the second position. Thus, when the engagement portion 321 is in the second position, the engagement portion is offset from the side wall 313. In other embodiments, however, the engagement portion 321 can engage the tissue sample while remaining outside of the internal volume 315.

The engagement portion 321 can include any surface or features that contact the target sample within the internal volume 315 to retain the target sample therein. For example, in some embodiments, the engagement portion 321 (and any of the engagement portions described herein) can include a textured surface to increase the friction between the engagement portion and the target sample to limit slipping or relative movement between the engagement portion and the target sample. In some embodiments, the engagement portion 321 (and any of the engagement portions described herein) can include a barbs, contours or other geometric features to increase contact (or friction) between the engagement portion and the target sample.

The retention member 320 is coupled to the elongated member 310 via the flexure 330 (also referred to as a living hinge). In use, the flexure 330 deforms when the retention member 320 moves relative to the elongated member 310. Similarly stated, the flexure 330 deforms when the engagement portion 321 moves from its first configuration (see, e.g., FIG. 20) to its second configuration (not shown). In this manner, as described above, the engagement portion 321 can rotate (i.e., about a pivot axis of rotation associated with the flexure 330) relative to the side wall 313. This arrangement results in a sample retrieval assembly with low part count, reduced friction between moving parts, and the ability to scale the device to smaller sizes, as compared to a grasping mechanism that use pin joints.

Referring to FIG. 21, the side wall 313 defines a series of notches or material cut-outs to form the retention member 320, including the engagement portion 321, the actuation portion 325, and the flexure 330. Specifically, the side wall 313 defines a notch or series of notches that surround a portion of the retention member 320, thereby allowing the retention member 320 to move, as described herein. In particular, the side wall 313 defines a lateral notch 322 and two longitudinal notches 323 that surround a portion of the retention member 320. In contrast to the lateral notch 222 described above with reference to the elongated member 210, the lateral notch 322 is curved.

The side wall 313 also defines two flexure notches 332 that form the flexure 330. Similarly stated, the flexure notches 332 separate the edges of the flexure 330 from the side wall 313, such that the flexure 330 can deform, as described herein. The flexure notches 332 are defined such that the circumferential size of the flexure 330 (i.e., the arc of the flexure 330) has an angle that is within a desired range. Specifically, the angle (not identified, but similar to the angle α described above with respect to the flexure 130) is within a desired range to both provide a sufficient amount of material to prevent failure of the flexure 330, while also maintaining the stiffness of the flexure 330 at a level to promote efficient and repeatable movement during actuation. For example, in some embodiments, the total arc of the flexure is between about 20 degrees and about 40 degrees. In some embodiments, the total arc of the flexure is about 30 degrees.

The flexure notches 332 are also defined such that the flexure 330 has a length L. The length L can be sufficient to distribute the stress that is produced by actuation across a larger portion of the side wall 313. Similarly stated, the length L of the flexure can reduce the localized stress as compared with that resulting from a shorter flexure design (e.g., as shown for the flexure 220), thereby increasing the fatigue life of the flexure 330. In this manner, the flexure can elastically deform, and thus can be repeatedly actuated. Accordingly, the flexure 330 is a resilient member that stores energy from the actuation force and releases the energy when the actuation force is removed, thus allowing the sample retrieval device 300 to repeatedly actuated. The length L of the flexure 330 can be any suitable length. For example, in some embodiments, a ratio of the length L of the edge of the flexure 330 to a diameter of the cylinder formed by the elongated member 310 is between about 0.2 and about 1.0. In other embodiments, a ratio of the length L of the edge of the flexure 330 to the diameter of the cylinder formed by the elongated member 310 is between about 0.7 and about 1.5.

As shown in FIG. 21, the actuation portion 325 includes a coupling opening 326 to which an actuator (not shown, but which can be any actuator of the types shown and described herein, including the actuator 191) can be coupled. In other embodiments, however, the actuation portion 325 can include any other suitable mechanism for coupling the actuator to the retention member 320. Such coupling mechanisms can include, for example, notches, clips, protrusions, or the like. FIG. 21 shows the actuation portion 325 is in a first configuration (or position) relative to the retention member 320, in which the actuation portion 325 is aligned with the flexure 330 and the engagement portion 321. The side wall 313 defines two longitudinal notches 329 and one lateral notch 328 that separate the actuation portion 325 from other portions of the retention member 320. Similarly stated, the notches 329 and the notch 328 collectively define a boundary of the actuation portion 325 of the retention member 320. To attach an actuator to the actuation portion 325, the actuation portion 325 is deformed relative to the engagement portion 321, and the actuator (not shown) is coupled within the opening 326.

Figure 22:
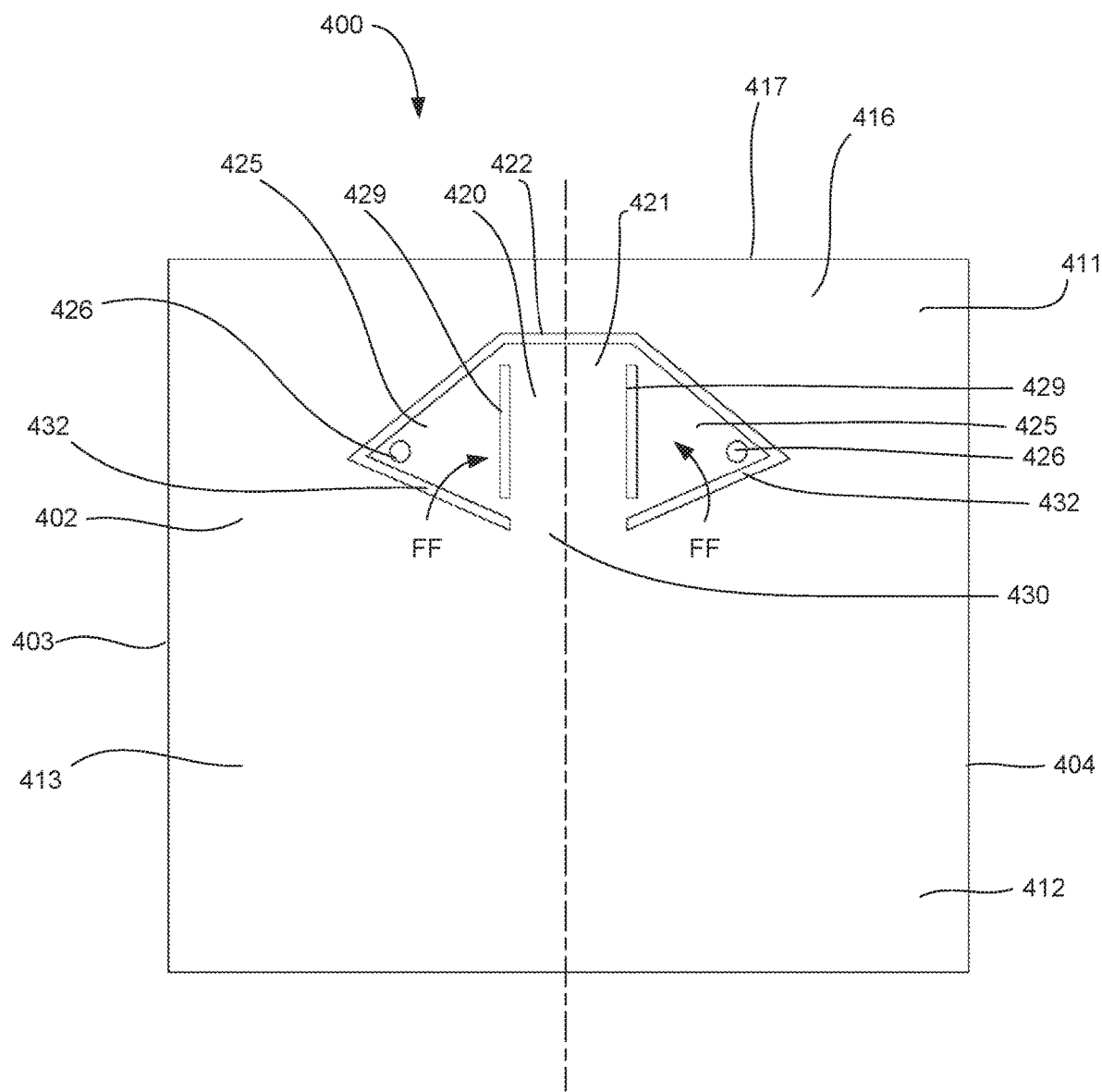
FIGS. 22 and 23 are top views of a sample retrieval tool according to an embodiment, in a first configuration.
Figure 23:
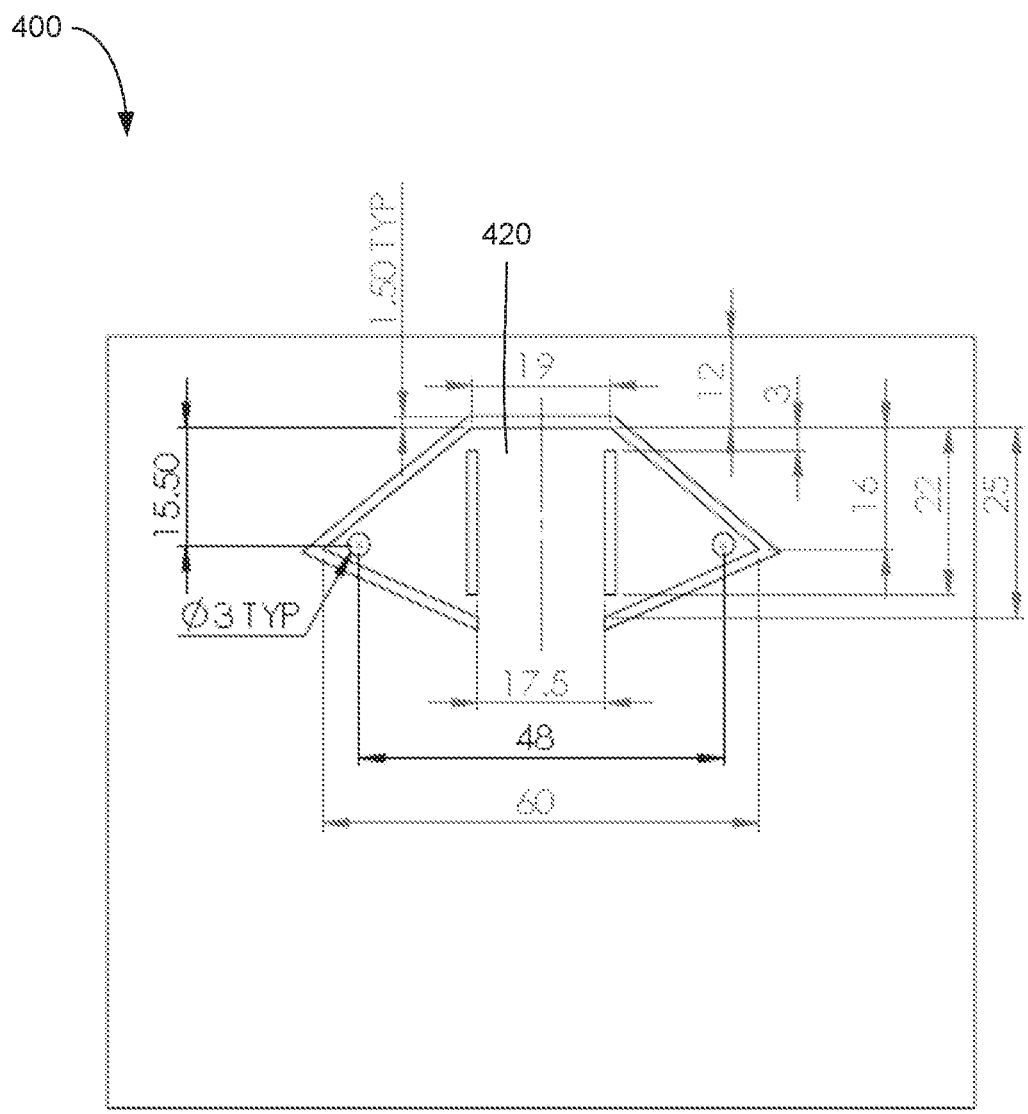

Although the sample retrieval tools shown and described above include a single retention member having a single actuation portion, in other embodiments, a sample retrieval tool can include any number of retention members. Moreover, in other embodiments, a sample retrieval tool can include a retention member having any number and configuration of actuation portions. For example, FIGS. 22 and 23 show a monolithically-constructed sample retrieval tool 400, according to an embodiment, that includes a retention member 420 having two actuation portions 425. FIG. 22 shows a portion of the sample retrieval tool 400 in a first configuration, prior to the sample retrieval tool 400 being formed to define an internal volume (similar to the internal volumes 115, 215, 315 described herein). Specifically, FIG.

22 shows the sample retrieval tool 400 as a flat material sheet 402, prior to being formed into an elongated member. FIG. 23 shows the flat material sheet 402, and includes possible dimensions (in mm) for the retention member 420. When formed, the sample retrieval device 400 includes an elongated member (also referred to as a cannula) and a retention member 420. The sample retrieval device 400, and any of the sample retrieval devices or assemblies described herein, can be used in any suitable application, such as, for example, in bodily tissue retrieval procedures, geological sample retrieval procedures, part grasping procedures (e.g., during assembly of components), or the like. For example, the sample retrieval device 400 or any of the components therein are optionally parts of a surgical assembly that performs biopsy procedures.

Referring to FIG. 22, the flat material sheet 402 is processed and manipulated to form a side wall 413 of the elongated member 410 (see FIG. 13). The flat material sheet 402 includes a proximal end portion 412, a distal end portion 411, and defines a longitudinal axis LA. Moreover, the flat material sheet 402 includes a first side edge 403 and a second side edge 404. Thus, when the material sheet 402 is manipulated to form the elongated member (e.g., according to the method 30, or any other methods described herein), the first side edge 403 is joined to the second side edge 404 to form a joint (not shown in FIG. 22, but similar to the joint 105 shown and described above). In this manner, the elongated member defines an internal volume that can receive a target sample, as described above with respect to the method 10. The resulting elongated member can have any suitable cross-sectional shape, such as, for example, a circular, elliptical, rectangular, or triangular cross-sectional shape, as described herein. Moreover, in some embodiments, the cross-sectional shape of the elongated member can vary along the longitudinal axis LA. For example, in some embodiments, the elongated member, or any of the elongated members described herein, can be tapered, as described herein.

The elongated member 410 includes a cutting portion 416 configured to cut a target sample (not shown) when the elongated member is moved. Such movement can be either linear translation along the longitudinal axis LA, rotation about the longitudinal axis LA, or a combination of linear movement and rotation. As described herein, after the cutting portion 416 cuts the target sample, a portion of the cut target sample can be moved into the internal volume. In some embodiments, the elongated member can include a cutting edge at a distal-most surface of the elongated member. For example, as shown in FIG. 22, the cutting portion 416 includes a cutting edge 417 at the distal-most end of the elongated member. In other embodiments, however, the cutting portion of an elongated member can be at any suitable location along the elongated member. For example, in some embodiments, the cutting portion 416 can be located between the distal end portion 411 and the proximal end portion. The cutting edge along the end surface 417 can be any suitable structure or shape to cut, separate, perforate, dilate, or sever the target sample. For example, in some embodiments, the cutting edge can be any one of a beveled cutting edge, a serrated cutting edge, or a trephine cutting edge.

The retention member 420 is monolithically constructed with and movably coupled to the elongated member, and is configured to move relative to the elongated member to retain the portion of the target sample within the internal volume. The retention member 420 includes an engagement portion 421, two actuation portions 425, and a flexure 430. Each of the engagement portion 421, the actuation portions 425, and the flexure 430 are monolithically constructed along with the sidewall 413 (which is formed into the elongated member), as described herein.

The engagement portion 421 of the retention member 420 is configured to move between a first position and a second position when the retention member 420 is actuated, as described above with respect to the retention members 120, 220, and 320. In this manner, a surface of the engagement portion 421 can exert a force (also referred to as a retention force) on the target sample when the engagement portion 421 is in the second position. As shown in FIG. 22, the engagement portion 421 is aligned with the side wall 413 when the engagement portion 421 is in the first position. Said another way, when the engagement portion 421 is in the first position, a longitudinal axis of the retention member 420 is aligned with, parallel to, or coaxial with the longitudinal axis LA of the elongated member. When actuated, the engagement portion 421 rotates relative to the side wall 413 to engage the tissue sample. The engagement portion 421 can include any surface or features that contact the target sample within the internal volume to retain the target sample therein. For example, in some embodiments, the engagement portion 421 can include a textured surface to increase the friction between the engagement portion and the target sample to limit slipping or relative movement between the engagement portion and the target sample. In some embodiments, the engagement portion 421 can include a barbs, contours or other geometric features to increase contact (or friction) between the engagement portion and the target sample.

The retention member 420 is coupled to the elongated member 410 via the flexure 430 (also referred to as a living hinge). In use, the flexure 430 deforms when the retention member 420 moves relative to the elongated member 410. Similarly stated, the flexure 430 deforms when the engagement portion 421 moves from its first configuration to its second configuration. In this manner, as described above, the engagement portion 421 can rotate (i.e., about a pivot axis of rotation associated with the flexure 430) relative to the side wall 413. This arrangement results in a sample retrieval assembly with low part count, reduced friction between moving parts, and the ability to scale the device to smaller sizes, as compared to a grasping mechanism that use pin joints.

As stated above, the retention member 420 is monolithically formed (integrally formed) with the elongated member 410 in the material sheet 402. Thus, the side wall 413 defines a series of notches or material cut-outs to form the retention member 420, including the engagement portion 421, the actuation portions 425, and the flexure 430. Specifically, the side wall 413 defines a notch or series of notches that surround a portion of the retention member 420, thereby allowing the retention member 420 to move, as described herein. In particular, the side wall 413 defines a lateral notch 422 and angled notches 423 that surround a portion of the retention member 420 and the two actuation portions 425.

The side wall 413 also defines two flexure notches 432 that intersect with the angled notches 423 and form the flexure 430. Similarly stated, the flexure notches 432 separate the edges of the flexure 430 from the side wall 413, such that the flexure 430 can deform, as described herein. The flexure notches 432 are defined such that the circumferential size of the flexure 430 (i.e., the arc of the flexure 430) has an angle that is within a desired range. Specifically, the angle (not identified, but similar to the angle α described above with respect to the flexure 130) is within a desired range to both provide a sufficient amount of material to prevent failure of the flexure 430, while also maintaining the stiffness of the flexure 430 at a level to promote efficient and repeatable movement during actuation. For example, in some embodiments, the total arc of the flexure is between about 20 degrees and about 40 degrees. In some embodiments, the total arc of the flexure is about 30 degrees.

In some embodiments, the flexure 430 (and any of the flexures described herein) can plastically deform when the retention member 420 is moved relative to the elongated member 410. In some such embodiments, the sample retrieval device 400 can be a single-use device in which the retention member 420 (and the engagement portion 421) remain in the second position even after any applied actuation force is released. In other embodiments, however, the flexure 430 (and any of the flexures described herein) can elastically deform, and can be repeatedly actuated. Thus, in some embodiments, the flexure 430 (and any of the flexures described herein) is a resilient member that stores energy from the actuation force and releases the energy when the actuation force is removed, thus allowing the sample retrieval device 400 to repeatedly actuated.

As shown in FIG. 22, each actuation portion 425 includes a coupling opening 426 to which an actuator, pin, or other mechanism (not shown, but which can be any actuator of the types shown and described herein, including the actuator 191) can be coupled. In other embodiments, however, the actuation portion 425 can include any other suitable mechanism for coupling the actuator, pin, or other mechanism to the retention member 420. Such coupling mechanisms can include, for example, notches, clips, protrusions, or the like. The actuation portion 425 is also be monolithically constructed with the retention member 420. Specifically, FIG. 22 shows the actuation portion 425 is in a first configuration (or position) relative to the retention member 420, in which the actuation portion 425 is aligned with the flexure 430 and the engagement portion 421. The side wall 413 defines two longitudinal notches 429 that separate the actuation portions 425 from other portions of the retention member 420. Similarly stated, the notches 429, the notches 423, and the flexure notches 432 collectively define a boundary of each actuation portion 425 of the retention member 420. To attach an actuator to the actuation portions 425, each actuation portion 425 is first deformed relative to the engagement portion 421, as shown by the arrows PP in FIG. 22. The actuation portions 425 can then be coupled together via a pin coupling (within the openings 426, see e.g., the device 500 below). The pin (not shown) can then be coupled to a single actuator, similar to the actuator 191 described above. In some embodiments, the actuation portions 425 can be separately coupled to individual actuators. The "dual actuation portion" configuration can provide spatially different attachment points for the actuator, can provide a different moment arm for actuation, or the like.

Although the sample retrieval tools shown and described above an elongated member having a cutting portion that is distinct from the retention member, in other embodiments, a sample retrieval tool can include one or more retention members that also include a cutting portion. For example, FIGS. 24 and 25 show a portion of a sample retrieval tool 500 that includes two retention members 520, each having a cutting edge 517, according to an embodiment. FIG. 24 shows the sample retrieval tool 500 in a first configuration and FIG. 25 shows the sample retrieval tool 500 in a second configuration.

The sample retrieval assembly 500 includes an elongated member 510 (also referred to as a cannula) and two retention members 520. The sample retrieval assembly 500, and any of the sample retrieval assemblies or devices described herein, can be used in any suitable application, such as, for example, in bodily tissue retrieval procedures, geological sample retrieval procedures, part grasping procedures (e.g., during assembly of components), or the like. For example, the sample retrieval assembly 500 or any of the components therein are optionally parts of a surgical assembly that performs biopsy procedures, which can include an articulating shaft, a wrist assembly, a series of nested cannulas, or the like. Thus, the distal end portion 511 of the elongated member 510 or an end portion of an actuator (not shown) can be coupled to an end of a surgical instrument shaft to form a biopsy assembly.

The elongated member 510 includes a distal end portion 511, and has a side wall 513 that defines an internal volume 515. As described herein, the internal volume 515 can receive a target sample. Although shown as having a cylindrical shape, the elongated member 510 can be any suitable shape. For example, in some embodiments, the elongated member 510 can have an elliptical, rectangular, or triangular cross-sectional shape. Moreover, in some embodiments, the cross-sectional shape of the elongated member 510 can vary along its longitudinal axis. For example, in some embodiments, the elongated member 510, or any of the elongated members described herein, can be tapered.

The retention members 520 are movably coupled to the elongated member 510, and are configured to move relative to the elongated member 510 to retain the portion of the target sample within the internal volume 515. Each retention member 520 includes an engagement portion 521, two opposing actuation portions 525, and a flexure 530. As shown in FIG. 24, the opposing actuation portions 525 are coupled together by a pin 527 that is coupled within a coupling opening 526 of each actuation portion 525. The opposing actuation portions 525 can be similar in design to the actuation portions 425 shown and described above, and can be formed, for example by a series of notches that define the edges of the respective coupling portion 525. The pin 527 can be coupled to an actuator (not shown) that is similar any of the actuators shown and described herein, such as the actuator 191. In other embodiments, the actuation portions 525 can include any suitable mechanism for coupling the pin 527 or an actuator to each retention member 520.

Each retention member 520 includes a cutting edge 517 configured to cut a target sample (not shown) when the elongated member 510 is moved. Such movement can be either linear translation, rotation, or a combination of linear movement and rotation. As described herein, after the cutting edge 517 cuts the target sample, a portion of the cut target sample can be moved into the internal volume 515. Specifically, the cutting edges 517 are the distal-most surface of each respective retention member 520. Moreover, unlike the cutting portion 116 (with its cutting edge 117) described above, the cutting edges 517 only partially surround the opening into the internal volume 515. The cutting edges 517 can be any suitable structure or shape to cut, separate, perforate, dilate, or sever the target sample. For example, in some embodiments, the cutting edge can be any one of a beveled cutting edge, a serrated cutting edge, or a trephine cutting edge.

Although the retention members 520 are shown as including the cutting edges 517, in other embodiments, the elongated member 510 can be disposed within ("nested within") a second elongated member (not shown) that surrounds the retention members 520, and that includes a cutting portion.

The engagement portion 521 of each retention member 520 is configured to move between a first position (FIG. 24) and a second position (FIG. 25) when the retention members 520 are actuated. For example, the retention members 520 can move inward, as shown by the arrows GG in FIG. 25, when a proximal force is exerted on the pin 527. In this manner, a surface of the engagement portion 521 can exert a force (also referred to as a retention force) on the target sample within the internal volume 515 when the engagement portion 521 is in the second position. Thus, the engagement portion 521 is aligned with the side wall 513 when the engagement portion 521 is in the first position. Said another way, when the engagement portion 521 is in the first position, a longitudinal axis of the retention member 520 is aligned with, parallel to, or coaxial with the longitudinal axis LA of the elongated member 510. In use, the engagement portion 521 rotates relative to the side wall 513 (as shown by the arrow DD) such that the engagement portion 521 is within the internal volume 515 when moved from the first position to the second position. Thus, when the engagement portion 521 is in the second position, the engagement portion is offset from the side wall 513.

The engagement portions 521 can include any surface or features that contact the target sample within the internal volume 515 to retain the target sample therein. For example, in some embodiments, the engagement portions 521 (and any of the engagement portions described herein) can include a textured surface to increase the friction between the engagement portion and the target sample to limit slipping or relative movement between the engagement portion and the target sample. In some embodiments, the engagement portion 521 (and any of the engagement portions described herein) can include a barbs, contours or other geometric features to increase contact (or friction) between the engagement portion and the target sample.

Each retention member 520 is coupled to the elongated member 510 via its respective flexure 530 (also referred to as a living hinge). In use, the flexures 530 deform when the retention members 520 move relative to the elongated member 510. Similarly stated, the flexures 530 deform when the engagement portions 521 move from their first configuration (FIG. 24) to their second configuration (FIG. 25). In this manner, as described above, the engagement portion 521 can rotate (i.e., about a pivot axis of rotation associated with the flexure 530) relative to the side wall 513. This arrangement results in a sample retrieval assembly with low part count, reduced friction between moving parts, and the ability to scale the device to smaller sizes, as compared to a grasping mechanism that use pin joints.

In some embodiments, the flexures 530 (and any of the flexures described herein) can plastically deform when the retention member 520 is moved relative to the elongated member 510. In some such embodiments, the sample retrieval assembly 500 can be a single-use device in which the retention member 520 (and the engagement portion 521) remain in the second position (or configuration) even after the actuation force is released. In other embodiments, however, the flexures 530 (and any of the flexures described herein) can elastically deform, and can be repeatedly actuated. Thus, in some embodiments, the flexures 530 (and any of the flexures described herein) is a resilient member that stores energy from the actuation force and releases the energy when the actuation force is removed, thus allowing the sample retrieval assembly 500 to repeatedly be moved between the first configuration (i.e., the first position of the engagement portions 521) and the second configuration (i.e., the second position of the engagement portions 521), or any other suitable configurations.

In some embodiments, the retention members 520 can be monolithically formed (i.e., can be integrally formed with) the elongated member 510. For example, in some embodiments, the elongated member 510 and the retention members 520 can be formed from a single material sheet according to the method 30 shown and described herein, or any or suitable methods.

Figure 26:
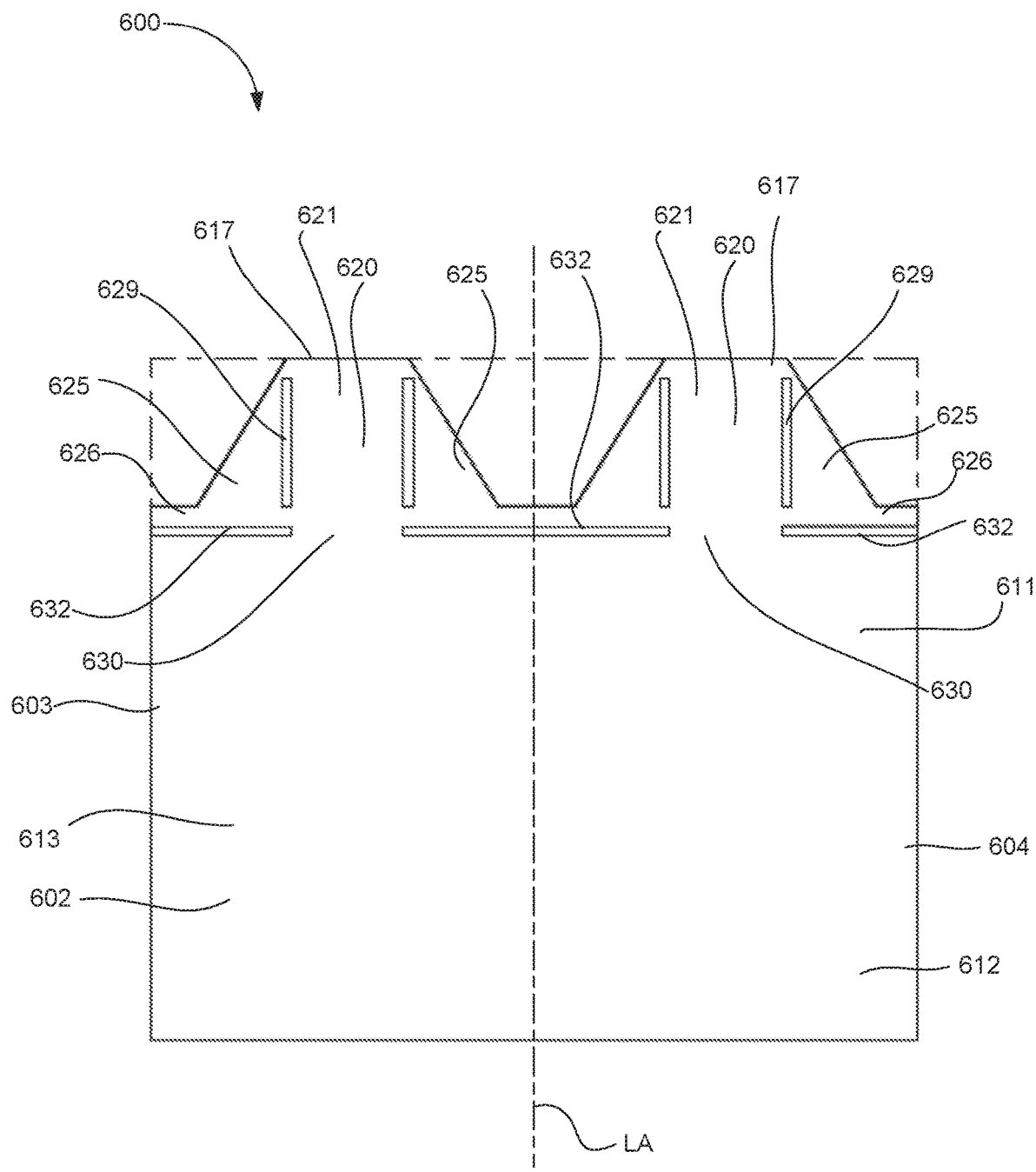
FIGS. 26 and 27 are top views of a sample retrieval tool according to an embodiment, in a first configuration.
Figure 27:
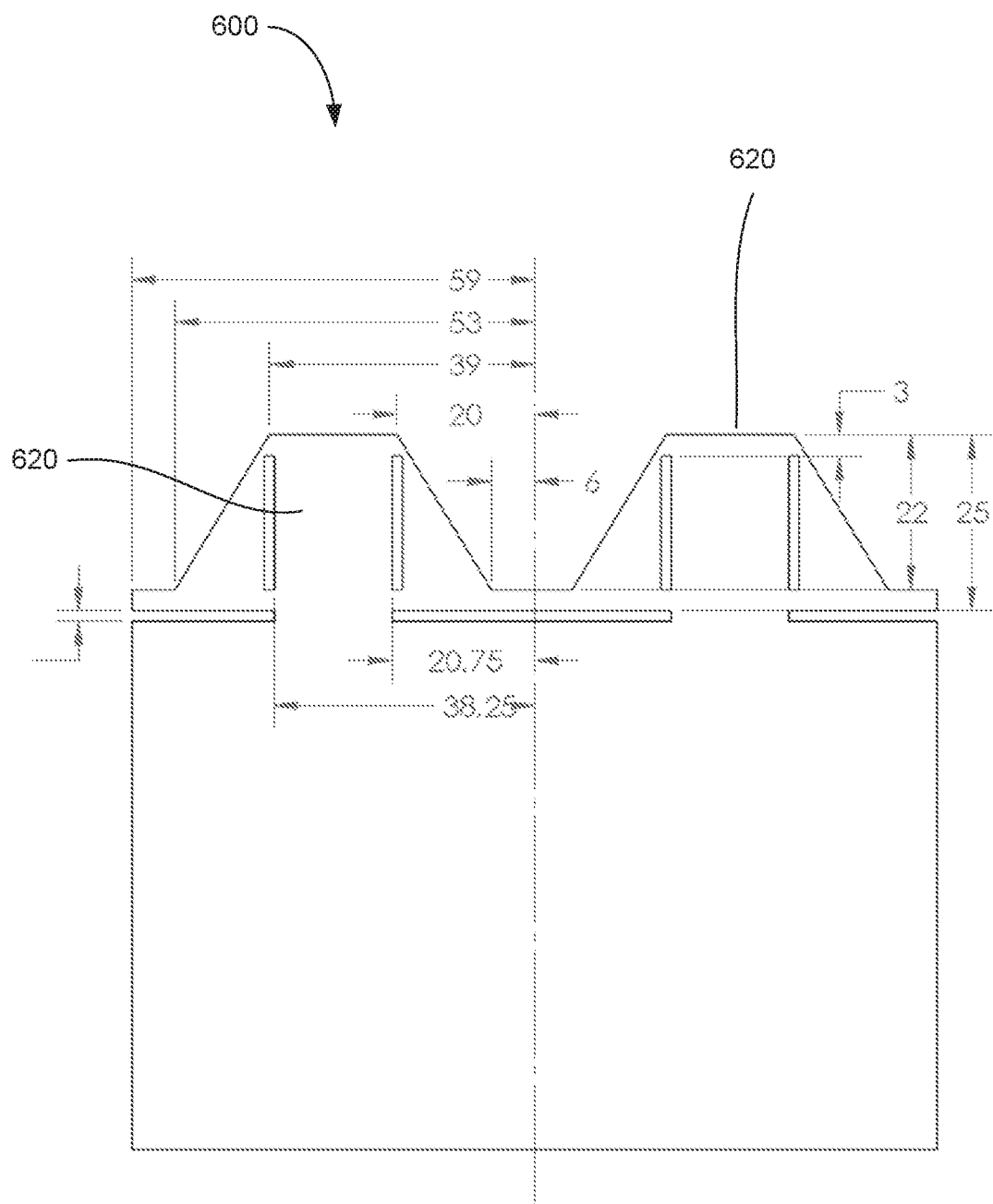

Although the sample retrieval tool 500 is shown as including two retention members, each with opposing actuation portions having separate ends (and that can be joined together, for example, via the pin 527), in other embodiments, a sample retrieval tool can include multiple actuation portions that are coupled together when the sample retrieval tool is formed. For example, FIGS. 26 and 27 show a monolithically-constructed sample retrieval tool 600, according to an embodiment, that includes two retention members 620, each having two actuation portions 625. FIG. 26 shows a portion of the sample retrieval tool 600 in a first configuration, prior to the sample retrieval tool 600 being formed to define an internal volume (similar to the internal volumes 115, 215, 315 described herein). Specifically, FIG. 26 shows the sample retrieval tool 600 as a flat material sheet 602, prior to being formed into an elongated member. FIG. 27 shows the flat material sheet 602, and includes possible dimensions (in mm) for the retention members 620. When formed, the sample retrieval device 600 includes an elongated member (also referred to as a cannula) and two retention members 620. The sample retrieval device 600, and any of the sample retrieval devices or assemblies described herein, can be used in any suitable application, such as, for example, in bodily tissue retrieval procedures, geological sample retrieval procedures, part grasping procedures (e.g., during assembly of components), or the like. For example, the sample retrieval device 600 or any of the components therein are optionally parts of a surgical assembly that performs biopsy procedures.

Referring to FIG. 26, the flat material sheet 602 is processed and manipulated to form a side wall 613 of the elongated member 610 (see FIG. 13). The flat material sheet 602 includes a proximal end portion 612, a distal end portion 611, and defines a longitudinal axis LA. Moreover, the flat material sheet 602 includes a first side edge 603 and a second side edge 604. Thus, when the material sheet 602 is manipulated to form the elongated member (e.g., according to the method 30, or any other methods described herein), the first side edge 603 is joined to the second side edge 604 to form a joint (not shown in FIG. 26, but similar to the joint 105 shown and described above). In this manner, the elongated member defines an internal volume that can receive a target sample, as described above with respect to the method 10. The resulting elongated member can have any suitable cross-sectional shape, such as, for example, a circular, elliptical, rectangular, or triangular cross-sectional shape, as described herein. Moreover, in some embodiments, the cross-sectional shape of the elongated member can vary along the longitudinal axis LA. For example, in some embodiments, the elongated member, or any of the elongated members described herein, can be tapered, as described herein.

Each of the retention members 620 includes a cutting edge 617 configured to cut a target sample (not shown) when the elongated member is moved. The cutting edges 617 are similar to the cutting edges 517 described above, and are therefore not described in detail herein. The retention members 620 are monolithically constructed with and movably coupled to the elongated member, and are configured to move relative to the elongated member to retain the portion of the target sample within the internal volume. Each retention member 620 includes an engagement portion 621, two actuation portions 625 (not all actuation portions are labeled), and a flexure 630. Each of the engagement portions 621, the actuation portions 625, and the flexures 630 are monolithically constructed along with the sidewall 613 (which is formed into the elongated member), as described herein.

The engagement portion 621 of each retention member 620 is configured to move between a first position and a second position when the retention member 620 is actuated, as described above with respect to the retention members 120, 220, 320, 420 and 520. In this manner, a surface of the engagement portion 621 can exert a force (also referred to as a retention force) on the target sample when the engagement portions 621 are in the second position. The engagement portions 621 can include any surface or features that contact the target sample within the internal volume to retain the target sample therein. For example, in some embodiments, the engagement portions 621 can include a textured surface to increase the friction between the engagement portion and the target sample to limit slipping or relative movement between the engagement portion and the target sample. In some embodiments, the engagement portions 621 can include a barbs, contours or other geometric features to increase contact (or friction) between the engagement portion and the target sample.

The retention members 620 are coupled to the side wall 613 (and ultimately, the elongated member) via the flexure 630 (also referred to as a living hinge). In use, the flexure 630 deforms when the retention member 620 moves relative to the elongated member 610. Similarly stated, the flexure 630 deforms when the engagement portion 621 moves from its first configuration to its second configuration. In this manner, as described above, the engagement portions 621 can rotate (i.e., about a pivot axis of rotation associated with the flexures 630) relative to the side wall 613. As stated above, the retention members 620 are monolithically formed (integrally formed) with the elongated member 610 in the material sheet 602. Thus, the side wall 613 defines a series of notches or material cut-outs to form the retention member 620, including the engagement portions 621, the actuation portions 625, and the flexures 630. Specifically, the side wall 613 defines a notch or series of notches that surround a portion of the retention member 620, thereby allowing the retention member 620 to move, as described herein.

The side wall 613 defines a series of flexure notches 632 that form the flexures 630 and also the connecting portions of the actuation portions 625. Similarly stated, the flexure notches 632 separate the edges of each flexure 630 from the side wall 613, such that the flexure 630 can deform, as described herein. The flexure notches 632 are defined such that the circumferential size of the flexure 630 (i.e., the arc of the flexure 630) has an angle that is within a desired range. Specifically, the angle (not identified, but similar to the angle α described above with respect to the flexure 130) is within a desired range to both provide a sufficient amount of material to prevent failure of the flexure 630, while also maintaining the stiffness of the flexure 630 at a level to promote efficient and repeatable movement during actuation. For example, in some embodiments, the total arc of the flexure is between about 20 degrees and about 40 degrees. In some embodiments, the total arc of the flexure is about 30 degrees.

As shown in FIG. 26, each actuation portion 625 includes two coupling legs 626 (not all are identified) to which an actuator, pin, or other mechanism (not shown, but which can be any actuator of the types shown and described herein, including the actuator 191) can be coupled. The central coupling leg between the two adjacent actuation portions 625 is monolithically constructed as a single leg. Thus, at least one side of two adjacent actuation portions is coupled upon formation. The other sides (adjacent the edges 603, 604) can be coupled together after the material sheet 602 is rolled. The side wall 613 defines series of longitudinal notches 629 that separate the actuation portions 625 from other portions of the retention members 620. Similarly stated, the notches 629 and the flexure notches 632 collectively define a boundary of each actuation portion 625 of the retention member 620. To attach an actuator to the actuation portions 625, each actuation portion 625 is first deformed relative to the engagement portion 621. The actuation portions 625 can then be coupled to a single actuator, similar to the actuator 191 described above. In some embodiments, the actuation portions 625 can be separately coupled to individual actuators. The "dual actuation portion" configuration can provide spatially different attachment points for the actuator, can provide a different moment arm for actuation, or the like.

Additional Prototypes and Test Results

Figure 29:
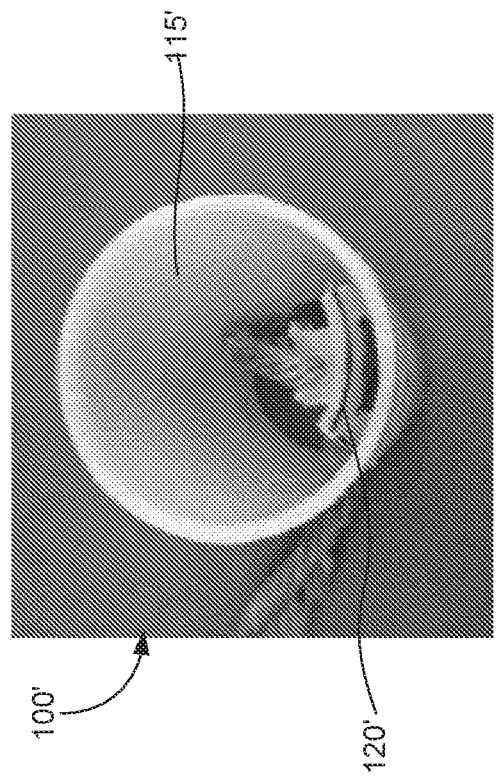
FIGS. 28 and 29 are photographs showing a side view and a top view, respectively, of a prototype sample retrieval tool, according to an embodiment.
Figure 28:
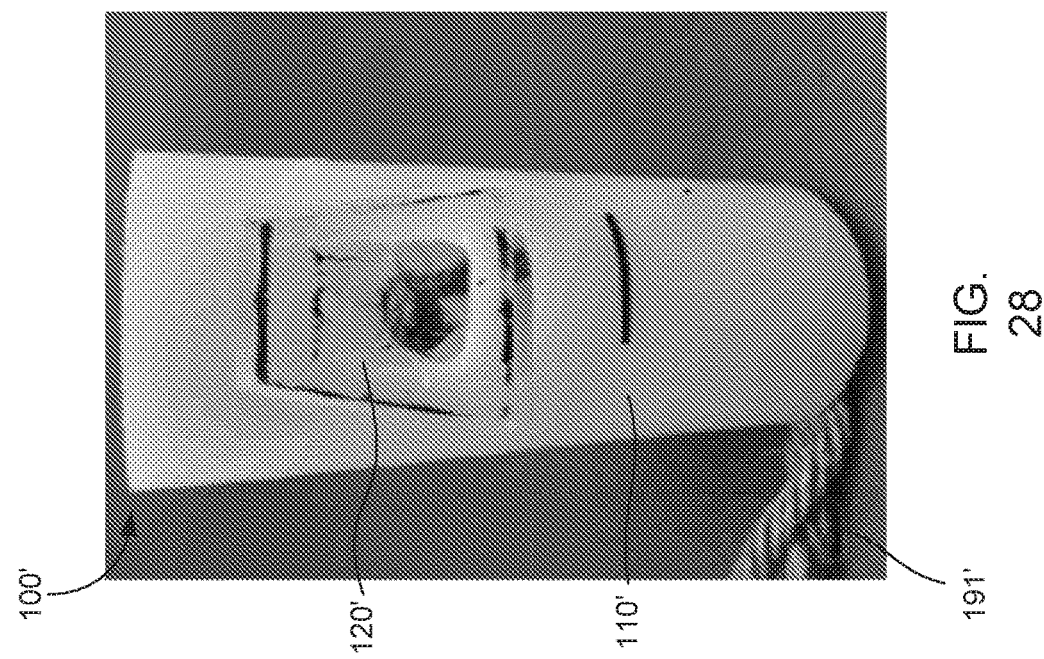

To evaluate the performance of the sample retrieval tools described herein, a series of physical prototype sample retrieval assemblies were made. As discussed below, the performance of the prototype joint assemblies was compared to assess differences in performance between the various designs. Specifically, FIGS. 28 and 29 are photographs showing a side view and a top view, respectively, of a large-scale prototype sample retrieval assembly 100'. The prototype sample retrieval assembly 100' is similar in design to the sample retrieval device 100 described above, and is therefore not described in detail herein.

As shown, the sample retrieval assembly 100' includes an elongated member 110' (also referred to as a cannula), a retention member 120', and an actuator 191'. The elongated member 110' defines an internal volume 115' that can receive a portion of a target sample. The elongated member 110' includes a cutting portion that is similar to the cutting portions 116 and 216, and is configured to cut the target sample when the elongated member is moved. The retention member 120' is similar to the retention member 120 described above, and is configured to move relative to the elongated member 110' to retain the portion of the target sample within the internal volume 115'. The retention member 120' includes an engagement portion (similar to the engagement portion 121), an actuation portion (similar to the actuation portion 125, and a flexure (similar to the flexure 130). As shown, the actuation portion is coupled to an actuator 191'. The prototype sample retrieval assembly 100' is referred to as the "integrated tip with single grabber" (or I.1.E) in the test results discussed below.

Figure 30:
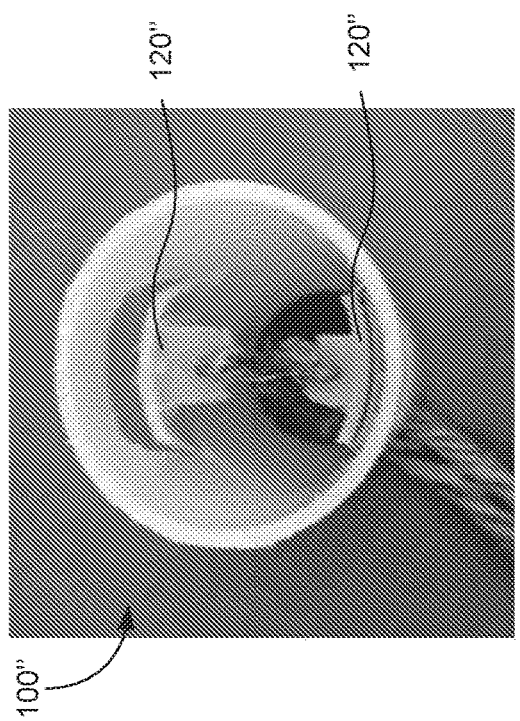
FIG. 30 is a photograph showing a top view of a prototype sample retrieval tool, according to an embodiment.

Although the sample retrieval tool 100' is shown as including a single retention member 120' (or grabber), in other embodiments, a sample retrieval tool can include any number of retention members. For example, FIG. 30 is a photograph of a large-scale prototype sample retrieval assembly 100''. The prototype sample retrieval assembly 100'' is similar in design to the sample retrieval device 100 and the retrieval device 100' described above, and is therefore not described in detail herein. As shown, the sample retrieval assembly 100'' includes two retention members 110'. The prototype sample retrieval assembly 100' is referred to as the "integrated tip with dual grabber" (or I.2.E) in the test results discussed below. Although not shown in FIGS. 28-30, in some embodiments, a sample retrieval tool can include a cutting edge on the retention members, such as that shown above with respect to the sample retrieval tools 500, 600 shown above. Prototype sample retrieval assemblies were produced having this configuration, and are referred to as the "integrated tip with single grabber—cutting edge on grabber" (or I.1.G) and the "integrated tip with dual grabber—cutting edge on grabber" (or I.2.G), respectively, in the test results discussed below.

Figure 32:
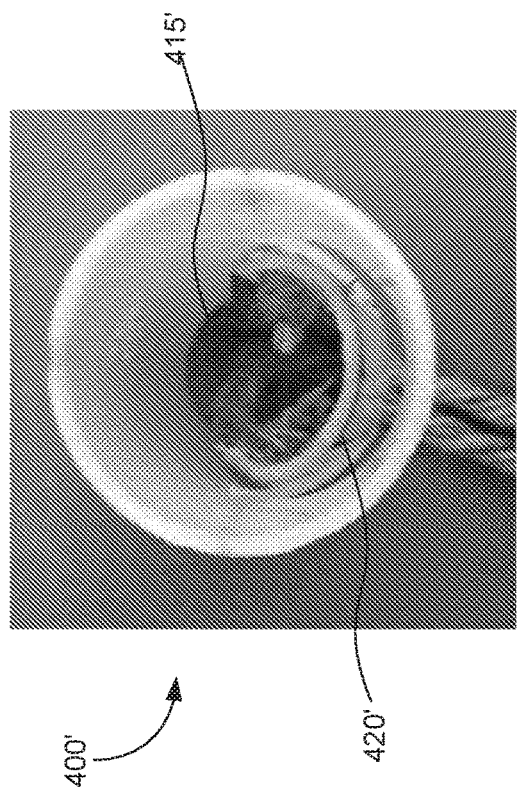
FIGS. 31 and 32 are photographs showing a side view and a top view, respectively, of a prototype sample retrieval tool, according to an embodiment.
Figure 31:
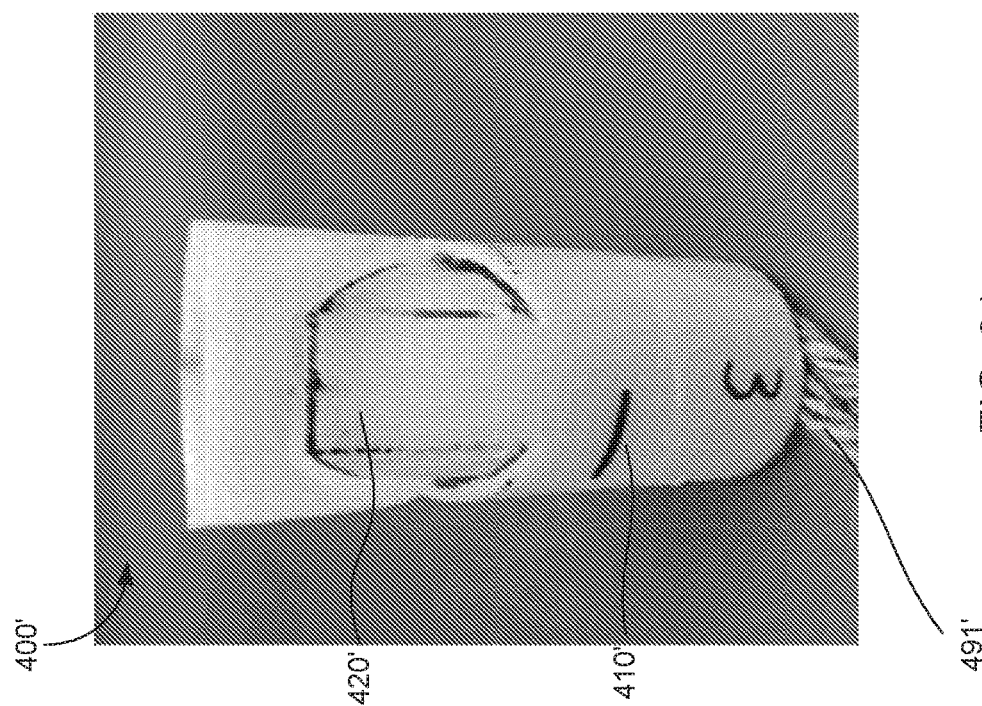

FIGS. 31 and 32 are photographs showing a side view and a top view, respectively, of a large-scale prototype sample retrieval assembly 400'. The prototype sample retrieval assembly 400' is similar in design to the sample retrieval device 400 described above, and is therefore not described in detail herein. As shown, the sample retrieval assembly 400' includes an elongated member 410' (also referred to as a cannula), a retention member 420', and an actuator 491'. The elongated member 410' defines an internal volume 415' that can receive a portion of a target sample. The elongated member 410' includes a cutting portion that is similar to the cutting portions 116 and 216, and is configured to cut the target sample when the elongated member is moved. The retention member 420' is similar to the retention member 420 described above, and is configured to move relative to the elongated member 410' to retain the portion of the target sample within the internal volume 415'. The retention member 420' includes an engagement portion (similar to the engagement portion 421), an actuation portion (similar to the actuation portion 425, and a flexure (similar to the flexure 430). As shown, the actuation portion is coupled to an actuator 491'. The prototype sample retrieval assembly 400' is referred to as the "pyramid with single grabber" (or P.1.E) in the test results discussed below.

Figure 33:
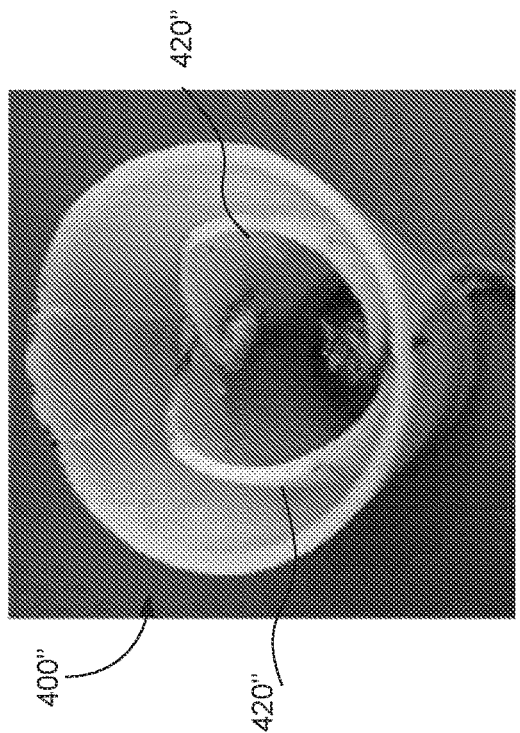
FIG. 33 is a photograph showing a top view of a prototype sample retrieval tool, according to an embodiment.

FIG. 30 is a photograph of a large-scale prototype sample retrieval assembly 400". The prototype sample retrieval assembly 400" is similar in design to the sample retrieval device 400 and the retrieval device 400' described above, and is therefore not described in detail herein. As shown, the sample retrieval assembly 400" includes two retention members 410'. The prototype sample retrieval assembly 400' is referred to as the "pyramid with dual grabber" (or P.2.E) in the test results discussed below. Although not shown in FIGS. 31-33, in some embodiments, a sample retrieval tool can include a cutting edge on the retention members, such as that shown above with respect to the sample retrieval tools 500, 600 shown above.

Figure 35:
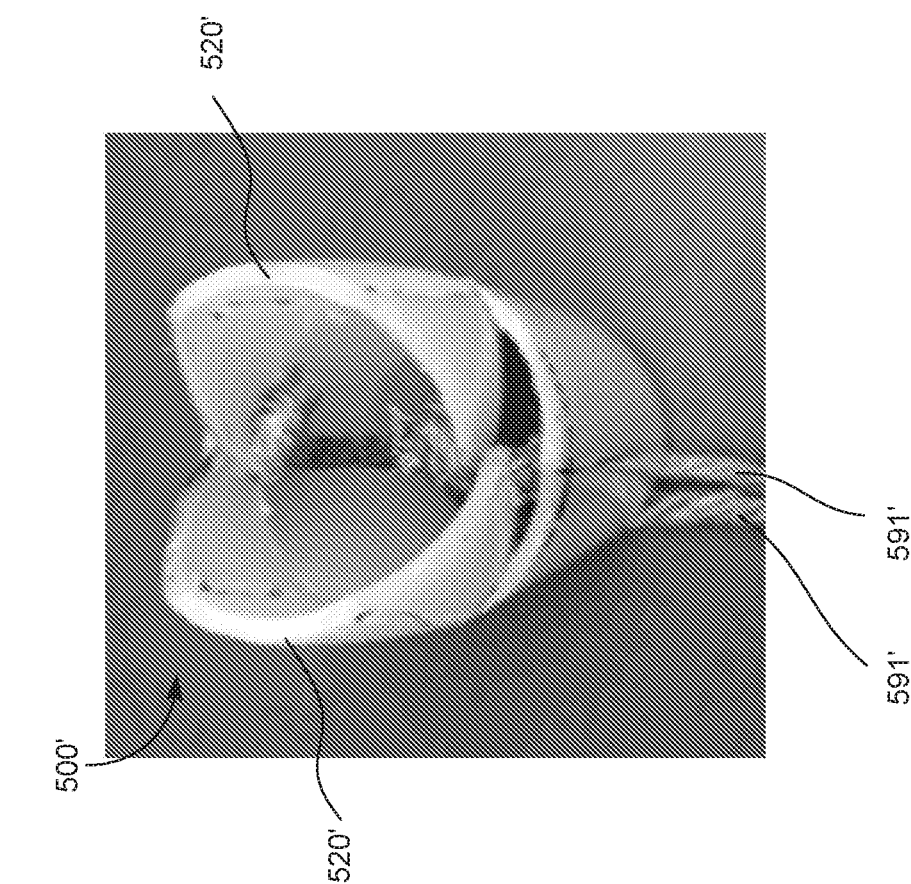
FIGS. 34 and 35 are photographs showing a side view and a top view, respectively, of a prototype sample retrieval tool, according to an embodiment.
Figure 34:
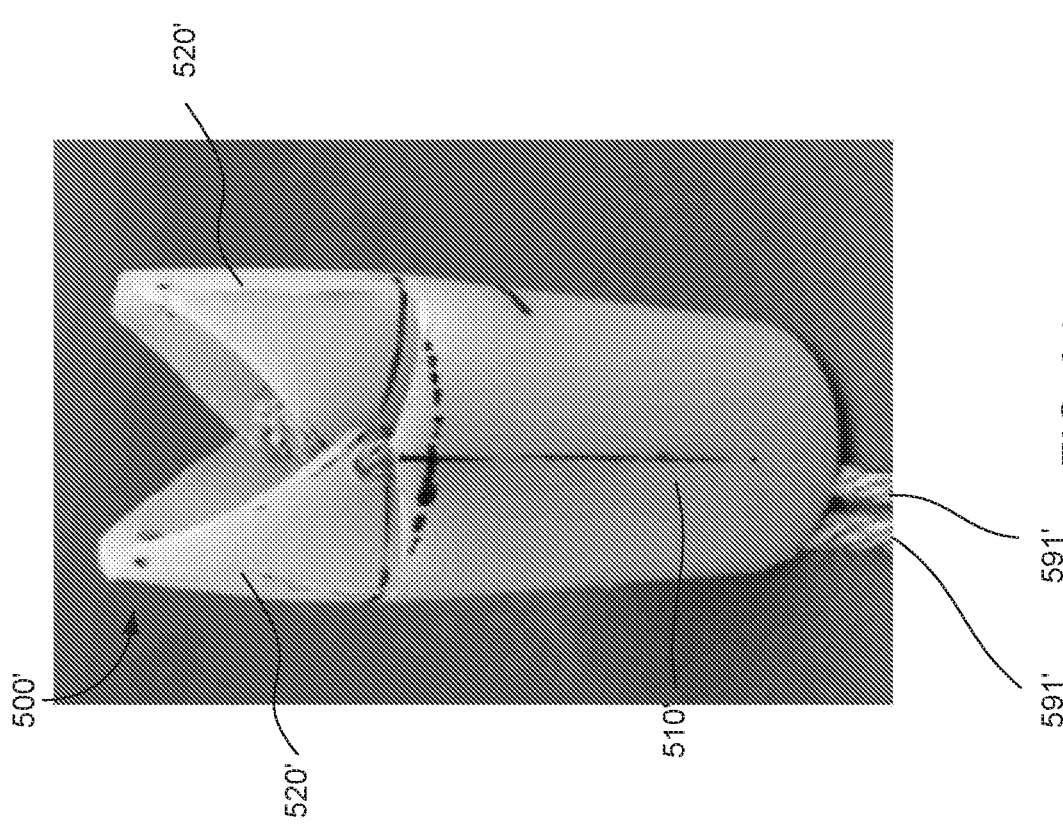

Prototype sample retrieval assemblies were produced having this configuration, and are referred to as the "pyramid with single grabber—cutting edge on grabber" (or P.1.G) and the "pyramid with dual grabber—cutting edge on grabber" (or P.2.G), respectively, in the test results discussed below. For example, FIGS. 34 and 35 are photographs showing a side view and a top view, respectively, of a large-scale prototype sample retrieval assembly 500'. The prototype sample retrieval assembly 500' is similar in design to the sample retrieval device 500 described above, and is therefore not described in detail herein. As shown, the sample retrieval assembly 500' includes an elongated member 510' (also referred to as a cannula), two retention members 520', and an actuator 591'. The elongated member 510' defines an internal volume 515' that can receive a portion of a target sample. The retention members 520' include a cutting portion that is similar to the cutting portions 116, 216 or the cutting edge 517, and that is configured to cut the target sample when the elongated member is moved. The retention members 520' are similar to the retention members 520 described above, and are configured to move relative to the elongated member 510' to retain the portion of the target sample within the internal volume 515'. The retention members 520' include an engagement portion (similar to the engagement portion 521), an actuation portion (similar to the actuation portion 525, and a flexure (similar to the flexure 530). As shown, the actuation portions are coupled to a series of actuators 591'. The prototype sample retrieval assembly 500' is referred to as the "pyramid with dual grabber—cutting edge on grabber" (or P.2.G) in the test results discussed below.

Figure 37:
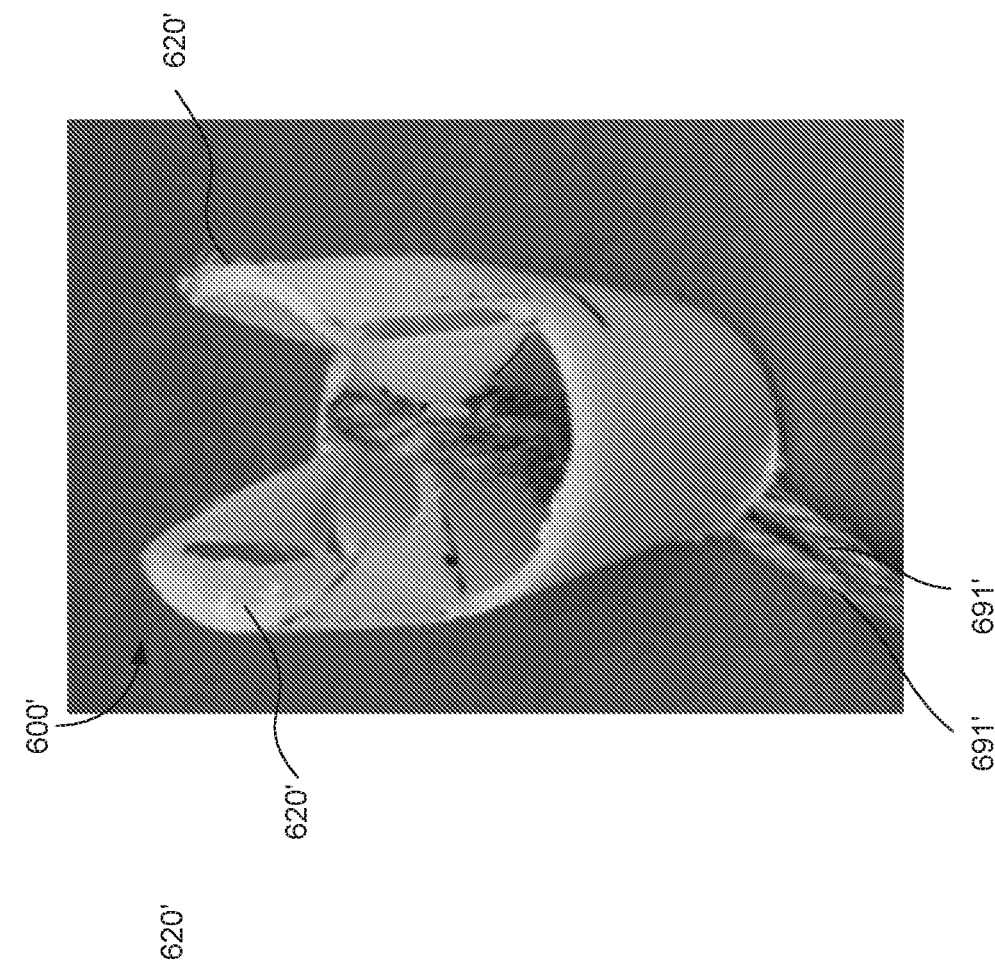
FIGS. 36 and 37 are photographs showing a side view and a top view, respectively, of a prototype sample retrieval tool, according to an embodiment.
Figure 36:
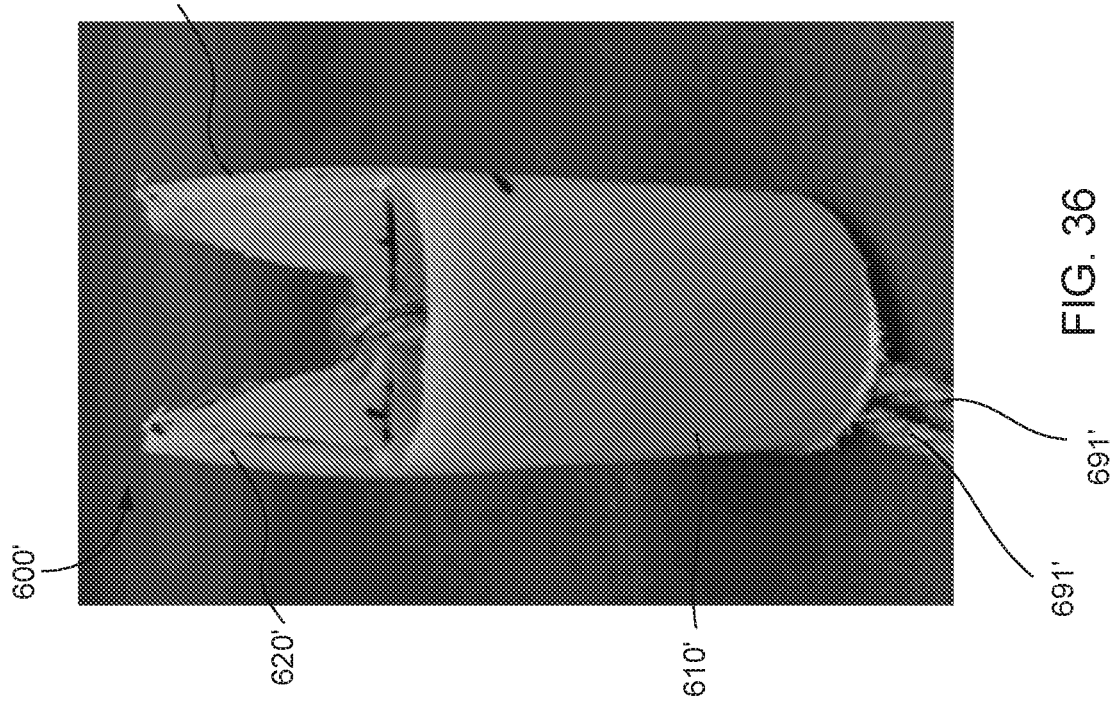

FIGS. 36 and 37 are photographs showing a side view and a top view, respectively, of a large-scale prototype sample retrieval assembly 600'. The prototype sample retrieval assembly 600' is similar in design to the sample retrieval device 600 described above, and is therefore not described in detail herein. As shown, the sample retrieval assembly 600' includes an elongated member 610' (also referred to as a cannula), two retention members 620', and an actuator 691'. The elongated member 610' defines an internal volume 615' that can receive a portion of a target sample. The retention members 620' include a cutting portion that is similar to the cutting portions 116, 216 or the cutting edge 617, and that is configured to cut the target sample when the elongated member is moved. The retention members 620' are similar to the retention members 620 described above, and are configured to move relative to the elongated member 610' to retain the portion of the target sample within the internal volume. The retention members 620' include an engagement portion (similar to the engagement portion 621), an actuation portion (similar to the actuation portion 625, and a flexure (similar to the flexure 630). As shown, the actuation portions are coupled to a series of actuators 691'. The prototype sample retrieval assembly 600' is referred to as the "coupled with two grabbers—cutting edge on grabbers" (or C.2.G) in the test results discussed below. Prototype assemblies were also made that included a single retention member ("coupled with single grabber—cutting edge on grabbers" (or C.1.G)); with a single retention member and with the cutting edge on the elongated member ("coupled with single grabber" (or C.1.E)); and with two retention members and with the cutting edge on the elongated member ("coupled with two grabbers" (or C.2.E)).

Test were conducted on the prototype sample retrieval tools to evaluate the performance the various designs. For the first series of tests, cups of gelatin (the substance used to simulate a target sample) were labeled and assigned to each combination of factors. A random experimental order was created using a random number generator, and each cup numbered accordingly. A test fixture was used to ensure that the prototypes sample retrieval tools entered the gelatin perpendicular to the surface. Similarly stated, the sample retrieval tools were aligned such that the longitudinal axis of each prototype was perpendicular to the surface of the target sample. A 500-gram weight was placed on top of the prototype to produce the linear movement of the elongated member into the target sample (i.e., the gelatin). The prototype was allowed to cut through the surface and travel until it stopped cutting through the gelatin, at which point a ruler was placed next to the cup and the distance traveled was measured in millimeters. The process was repeated for each prototype according to the random order.

Figure 38:
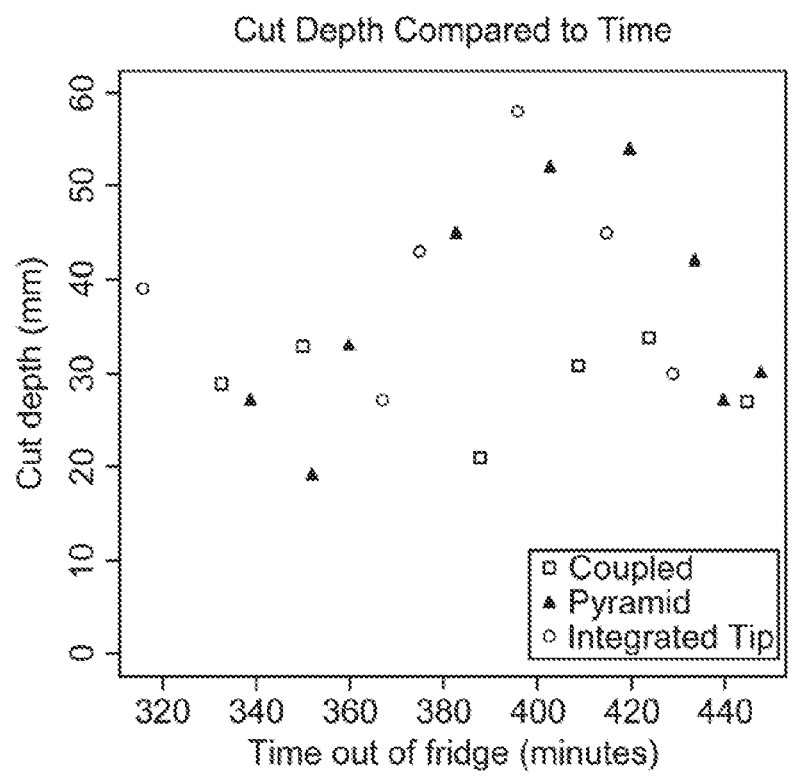
FIG. 38 is a plot of the depth of sample cut for various prototype designs as a function of the time during which the sample was not refrigerated.

FIG. 38 is a plot of the depth of sample cut for various prototype designs as a function of the time during which the sample was not refrigerated. This test was performed to determine whether the cut depth was related to the time the gelatin had been slightly warming. As can be seen in FIG. 38, the results appear to be random, and thus it was concluded that the time spent out of the refrigerator did not significantly impact the results.

Figure 39:
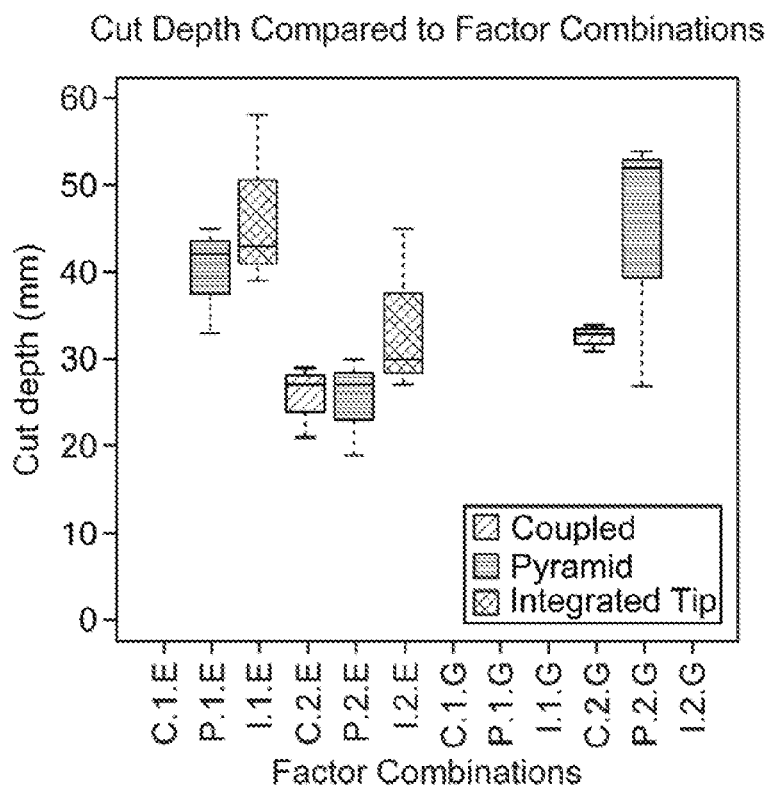
FIG. 39 is a plot of the depth of sample cut for various prototype designs.

FIG. 39 is a plot of the depth of sample cut for various prototype designs. Median values are plotted as the solid line in the middle of each box, with maximum and minimum values shown by the location of the end of the whiskers on the top and bottom, respectively. Based on this test, it was concluded that the pyramid double-grabber with grabber cutting (prototype design P.2.G) provided the best cutting performance, followed by the integrated tip single-grabber with tube end cutting (prototype design I.1.E) and the pyramid single grabber with tube end cutting (prototype design P.1.E). Moreover, FIG. 39 shows that the coupled double-grabber with grabber cutting (prototype design C.2.G) was the most consistent of the seven prototypes.

A second series of tests was conducted using the gelatin samples (to simulate a target sample) and the prototype designs. In particular, immediately following the "depth of cut" experiment, the prototype (which was already inserted into the gelatin from the first series of tests) was adjusted (inserted more in some cases and pulled out some in a few) until the gelatin was 12 mm past the base of the grabber. This was done to simulate inserting the grabber into tissue and going to the same point behind the grabber before actuating. A test fixture was then set over the sample to allow for actuation without disturbing the prototype and gelatin interaction in the cup, and the prototype retention member ("grabber") was actuated. While actuated, the end of the prototype was transferred to another container on a scale, and the mass of the extracted gelatin m was measured. Based on the known density of the gelatin, volume was calculated.

Figure 40:
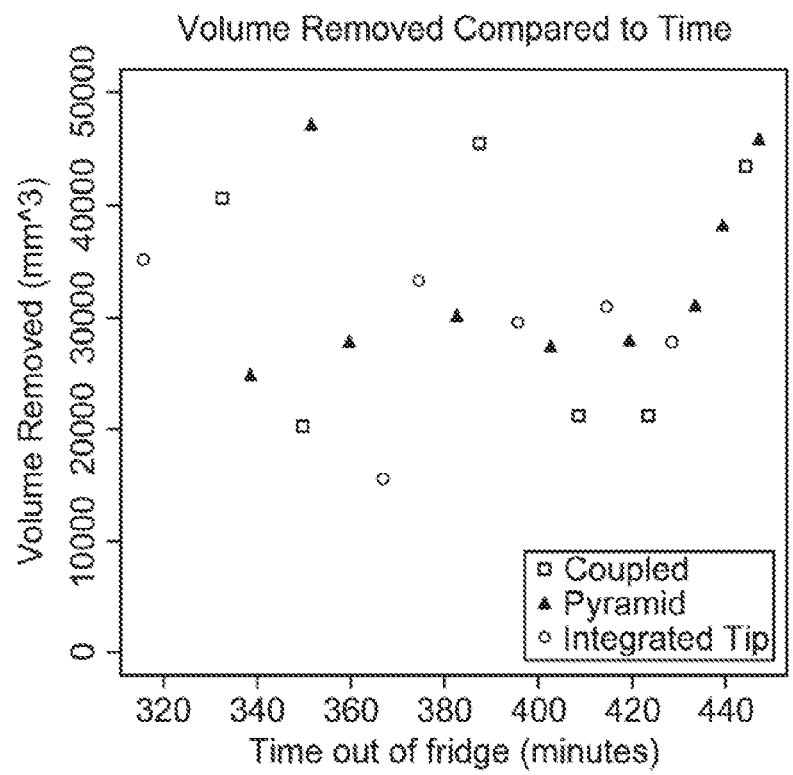
FIG. 40 is a plot of the volume of sample removed for various prototype designs as a function of the time during which the sample was not refrigerated.
Figure 41:
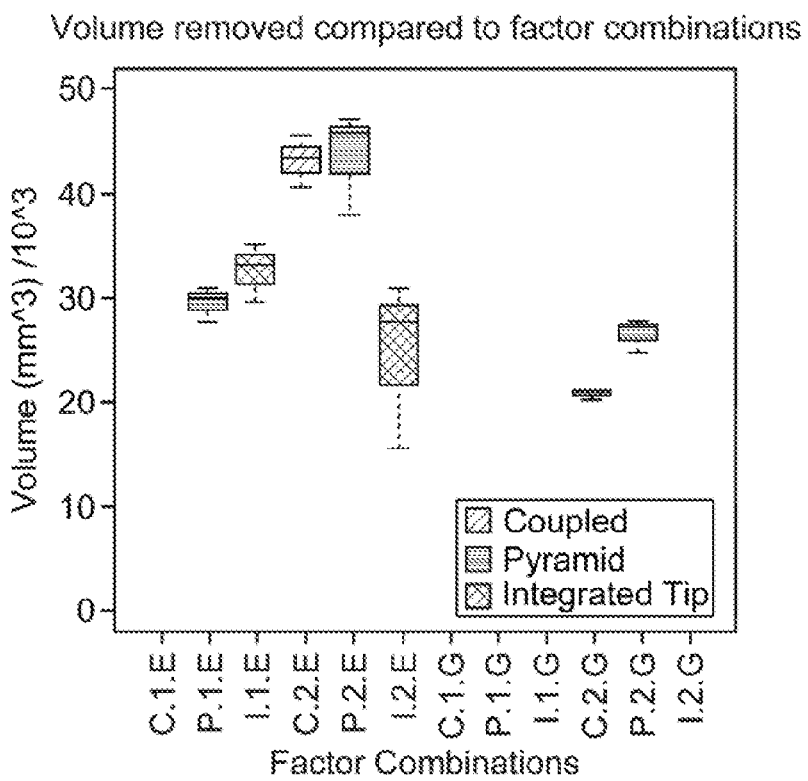
FIG. 41 is a plot of the volume of sample removed for various prototype designs.

The extracted volume results are displayed in FIGS. 40 and 41. In particular, FIG. 40 is a plot of the volume of sample removed for various prototype designs as a function of the time during which the sample was not refrigerated. As can be seen in FIG. 40, the results appear to be random, and thus it was concluded that the time spent out of the refrigerator did not significantly impact the results.

FIG. 41 is a plot of the volume of sample removed for various prototype designs. Median values are plotted as the solid line in the middle of each box, with maximum and minimum values shown by the location of the end of the whiskers on the top and bottom, respectively. Based on this test, it was concluded that the pyramid-tip double-grabber with grabber end cutting (prototype design P.2.G) was the consistently removed the highest volume of tissue, followed closely by the coupled double-grabber with tube end cutting (prototype design C.2.E). One interesting final note is that the coupled double-grabber with grabber cutting (prototype design C.2.G) was again the most consistent of the seven prototypes. By examining FIG. 41, it can be surmised that, in general, the prototypes cutting with a tube surface are typically better than the those cutting with the grabber (i.e., the retention member). This conclusion, however, should be tempered by the fact that there are only two prototypes that cut with their grabber compared to five that cut with a tube, and the grabber-cutting prototypes are underrepresented as a result.

Figure 42:
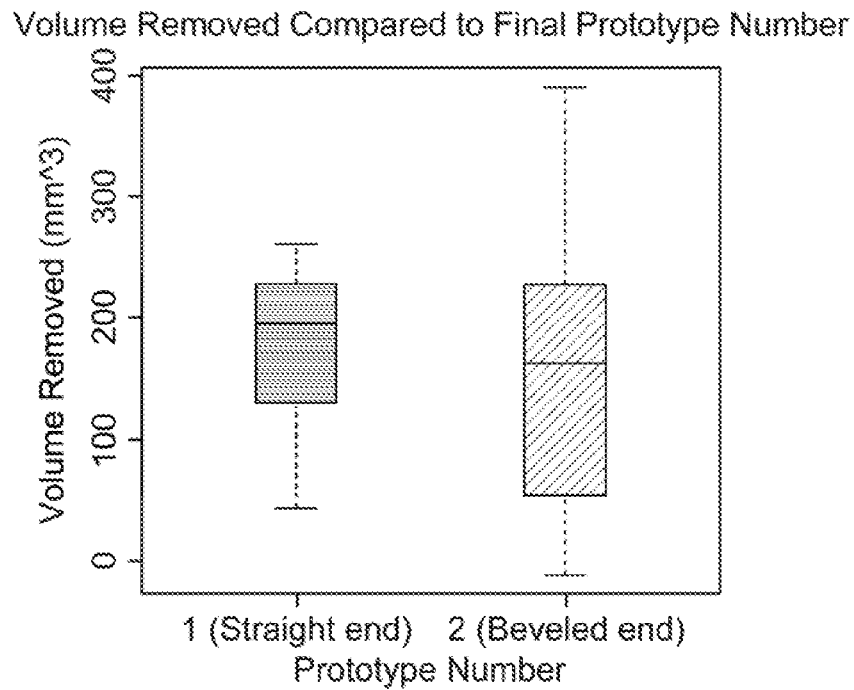
FIG. 42 is a plot of the volume of sample removed for a prototype having a straight cutting edge and a prototype having a beveled cutting edge.

FIG. 42 is a plot of the volume of sample removed for a prototype having a straight cutting edge (e.g., prototype 200') and a prototype having a beveled cutting edge (e.g., prototype 200"). Each prototype was tested ten times, and results are presented as a boxplot with the dark line being the median value. As can be seen, Prototype 2 (bevel) has a higher maximum value, but Prototype 1 (flat end) has a higher mean and median value.

Figure 43:
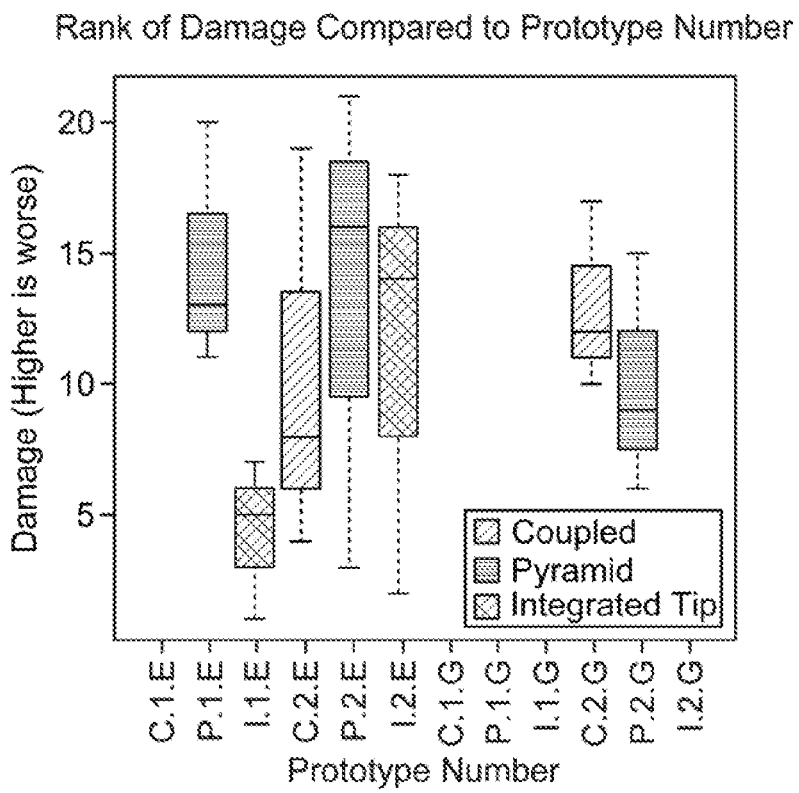
FIG. 43 is a plot showing a ranking of sample damage for various prototype designs.

During the above-mentioned testing, photographs were taken of the gelatin samples to allow qualitative comparison of how much the prototype disturbed the surrounding tissue throughout the process. One or two side photographs (depending on if the insertion was symmetrical or not), and an angled top photo were taken and presented to an independent individual who was instructed to rank them relative to one another. The photographs were ranked according to the damage caused to surrounding "tissue" by the simulated biopsy process performed with the prototypes. It should be noted that depth of cut was not a primary concern when comparing damage. Rather, the collateral damage done to the external gelatin that was not directly impacted by the grasper was assessed, as well as the damage done on the edges of the hole created by the elongated members. FIG. 43 is a plot showing a ranking of sample damage for various prototype designs. In general, it can be concluded that the integrated tip single-grabber with end cutting damaged the tissue the least.

Figure 45:
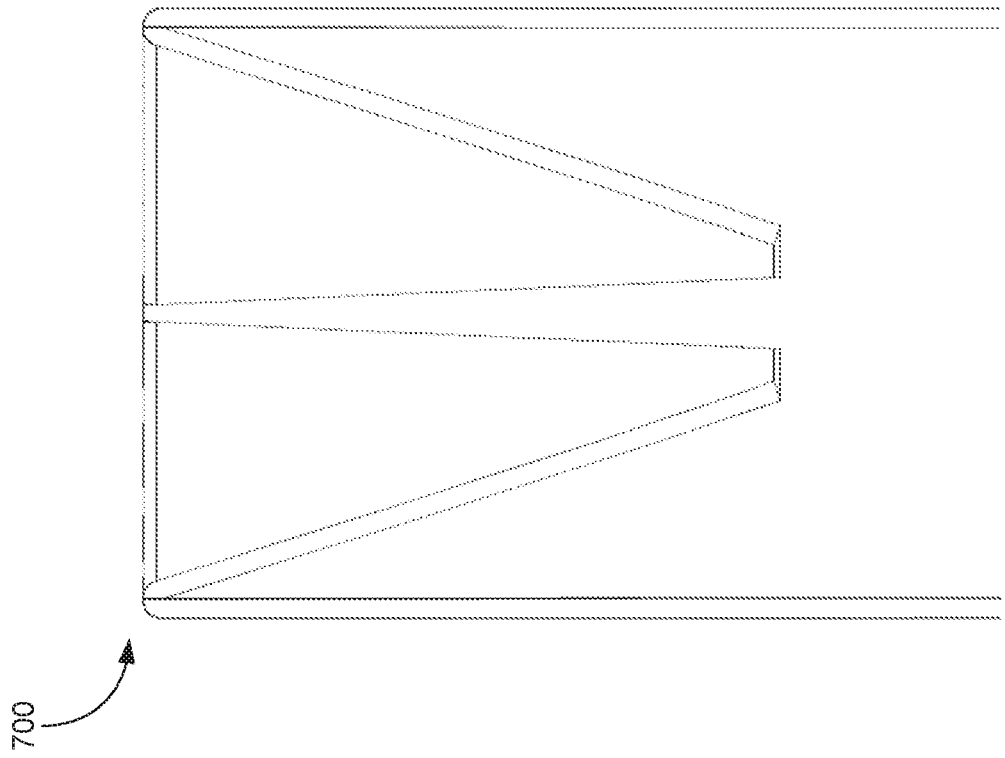
FIGS. 44 and 45 are a perspective view and a cross-sectional view, respectively, of a sample retrieval tool, according to an embodiment.
Figure 44:
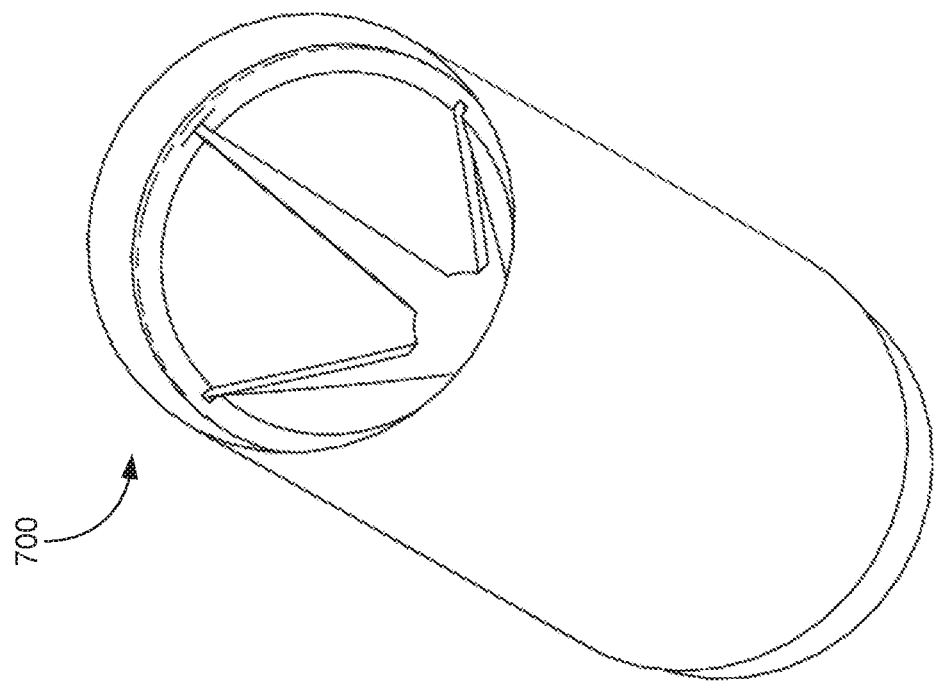

FIGS. 44 and 45 are a perspective view and a cross-sectional view, respectively, of a sample retrieval tool 700, according to an embodiment. The sample retrieval tool 700 includes an inner elongated member and an outer elongated member. The inner elongated member includes a series of inwardly-flexing retention members.

Figure 47:
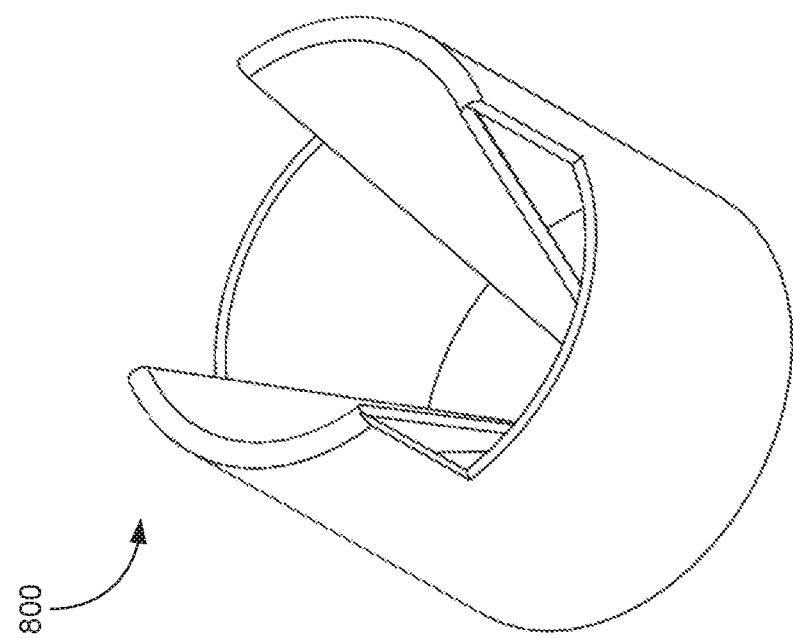
FIGS. 46 and 47 are perspective views of a sample retrieval tool, according to an embodiment.
Figure 46:
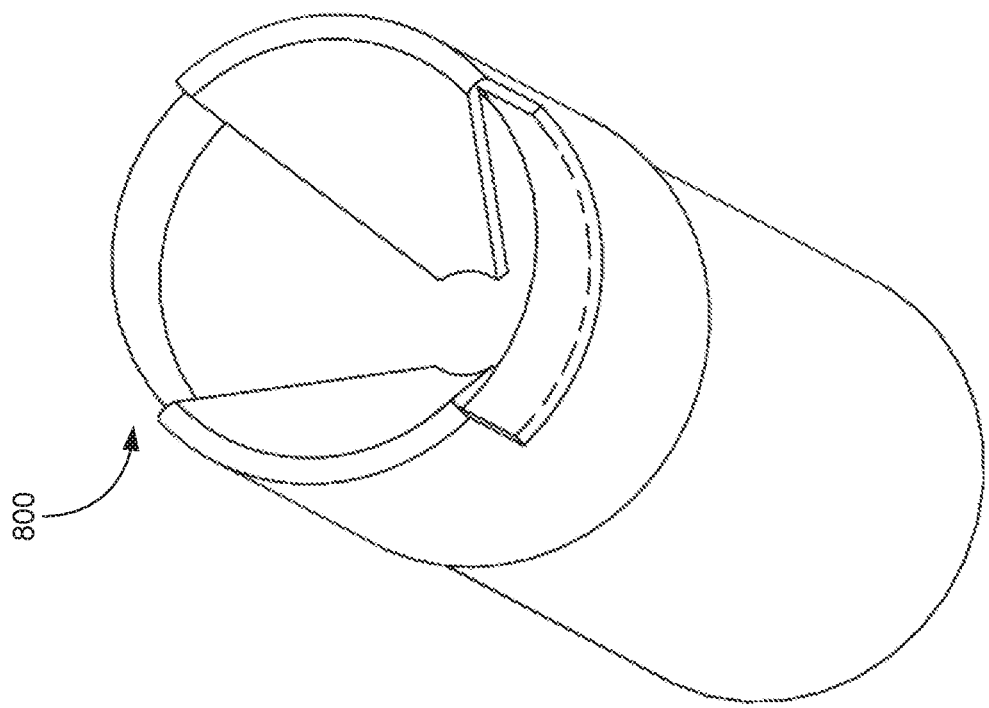

FIGS. 46 and 47 are perspective views of a sample retrieval tool 800, according to an embodiment. The sample retrieval tool 700 includes an inner elongated member and an outer elongated member. The outer elongated member is disposed about the inner member, and includes a series of inwardly-flexing retention members.

Any of the flexures, sample retrieval tools, or retention members described herein can be constructed from any suitable material to produce the desired flexibility, resilience, and durability during operation. For example, in some embodiments, any of the flexures, sample retrieval tools, or retention members described herein can be fabricated from stainless steel, titanium, metallic glass, and the nickel titanium alloy, Nitinol®. Nitinol® (also referred to as NiTi) includes nearly equal atomic percentages of nickel and titanium. NiTi can exhibit the superelastic effect and is therefore suitable for use in the compliant mechanisms described herein due to the large strains that it can undergo before yielding. Flexures constructed from NiTi can reach strains of between about 6% and about 8% with very small material set. Conversely, steels generally reach strains on the order of less than 1% before yielding.

While various embodiments have been described above, it should be understood that they have been presented by way of example only, and not limitation. Where methods and/or schematics described above indicate certain events and/or flow patterns occurring in certain order, the ordering of certain events and/or operations may be modified. While the embodiments have been particularly shown and described, it will be understood that various changes in form and details may be made.

For example, any of the tool members can be constructed from any material, such as medical grade stainless steel, nickel alloys, titanium alloys or the like. Further, any of the flexures, sample retrieval tools, retention members, or components described herein can be constructed from multiple pieces that are later joined together. For example, in some embodiments, an elongated member can be constructed by joining together separately constructed components. In other embodiments, however, any of the flexures, sample retrieval tools, retention members, or components described herein can be monolithically constructed.

Any of the sample retrieval tools described herein can include a stylet to obstruct, pierce, separate tissue.

Although the retention member 120 is shown as being coupled to the actuator 191 by the actuation portion 125, in other embodiments, the retention member 120 (and any of the retention members shown and described herein) can be coupled to an actuator by any suitable mechanism. For example, in some embodiments, a retention member can include an engagement portion that is coupled to an actuator by a magnetic coupling.

Although various embodiments have been described as having particular features and/or combinations of components, other embodiments are possible having a combination of any features and/or components from any of embodiments as discussed above. Aspects have been described in the general context of medical devices, and more specifically surgical instruments, but inventive aspects are not necessarily limited to use in medical devices.

What is claimed is:

1. An apparatus, comprising:
an elongated member comprising a cutting portion and a side wall, the cutting portion being configured to cut a target sample when the elongated member is moved, and the side wall defining an internal volume within which at least a portion of the target sample can be received; and
a retention member movably coupled to the elongated member, the retention member comprising an engagement portion and an actuation member;
wherein the actuation member of the retention member is configured to be coupled to an actuator;
the engagement portion of the retention member includes a flexure at a proximal end portion of the engagement portion that allows the engagement portion to move between a first position in which a distal end portion of the engagement portion is substantially aligned with the side wall of the elongated member and a second position in which the distal end portion of the engagement portion is disposed within the internal volume as the retention member is actuated by the actuator;
the engagement portion at the second position exerts a force on the target sample within the internal volume;
the retention member and the side wall are monolithically constructed;
the side wall comprises a first notch that surrounds a portion of the retention member except for the flexure; and
the retention member comprises a second notch that surrounds a portion of the actuation member.

2. The apparatus of claim 1, wherein:
the cutting portion comprises a cutting edge at an end surface of the elongated member;
the end surface defines an opening in fluid communication with the internal volume; and
the cutting edge surrounds the opening.

3. The apparatus of claim 1, wherein:
the cutting portion comprises a cutting edge at an end surface of the elongated member, the cutting edge being any one of a beveled cutting edge, a serrated cutting edge, or a trephine cutting edge.

4. The apparatus of claim 1, wherein:
the engagement portion is configured to rotate relative to the side wall when the engagement portion is moved from the first position to the second position.

5. The apparatus of claim 1, wherein:
the flexure is configured to deform when an actuation force is exerted on the retention member to move the engagement portion from the first position to the second position.

6. The apparatus of claim 1, wherein:
the side wall forms a cylinder that defines the internal volume; and
the flexure defines an angle about a circumference of the cylinder when the engagement portion is in the first position, the angle being between about 20 degrees and about 40 degrees.

7. The apparatus of claim 1, wherein:
the flexure is configured to deform when the actuator exerts an actuation force on the actuation member to move the engagement portion from the first position to the second position;
the engagement portion rotates relative to the side wall about a pivot axis when the flexure deforms; and
the flexure is configured to deform elastically when the actuator exerts the actuation force.

8. The apparatus of claim 1, wherein:
the apparatus further comprises a second retention member movably coupled to the elongated member;
the second retention member comprises a second engagement portion that moves between a third position and a fourth position when the second retention member is actuated; and
the second engagement portion at the fourth position exerts a second force on the target sample within the internal volume.

9. An apparatus, comprising:
an elongated member comprising a cutting portion and a side wall, the cutting portion being configured to cut a target sample as the elongated member is moved, and the side wall defining an internal volume within which at least a portion of the target sample can be received;
a first retention member monolithically constructed with and movably coupled to the elongated member, the first retention member comprising a first engagement portion and an actuation member, the first engagement portion being configured to move between a first position and a second position, the first engagement portion being configured to exert a first force on the target sample when the first engagement portion is in the second position, and the actuation member being configured to be coupled to an actuator that moves the first engagement portion from the first position to the second position; and
a second retention member monolithically constructed with and movably coupled to the elongated member, the second retention member comprising a second engagement portion configured to move between a third position and a fourth position when the second engagement portion of the second retention member is actuated, the second engagement portion of the second retention member being configured to exert a second force on the target sample when the second engagement portion is in the fourth position,
the first engagement portion of the first retention member includes a flexure at a proximal end portion of the first engagement portion that allows the first engagement portion to move between the first position in which a distal end portion of the first engagement portion is substantially aligned with the side wall of the elongated member and the second position in which the distal end portion of the first engagement portion is disposed within the internal volume as the first retention member is actuated by the actuator, the side wall comprises a first notch that surrounds a portion of the first retention member except for the flexure; and the first retention member comprises a second notch that surrounds a portion of the actuation member.

10. The apparatus of claim 9, wherein:

the first engagement portion of the first retention member is configured to rotate relative to the side wall when moved from the first position to the second position.

11. The apparatus of claim 9, wherein:

the flexure is configured to deform when the actuator exerts an actuation force on the actuation member of the first retention member to move the first engagement portion from the first position to the second position.

12. The apparatus of claim 11, wherein:

the side wall forms a cylinder that defines the internal volume;

the first notch separates an edge of the flexure from the side wall such that the first engagement portion rotates relative to the side wall about a pivot axis when the flexure deforms; and a ratio of a length of the edge to a diameter of the cylinder is between about 0.2 and 1.0.

13. The apparatus of claim 9, wherein:

the actuator is a first actuator; and the second retention member comprises an actuation member configured to be coupled to a second actuator, the second actuator being configured to move the second engagement portion of the second retention member from the third position to the fourth position.

14. The apparatus of claim 9, wherein:

the second retention member comprises a second actuation member configured to be coupled to the actuator; and the actuator is configured to move the second engagement portion of the second retention member from the third position to the fourth position.

15. The apparatus of claim 1, further comprising:

the actuator, the actuator being coupled to the actuation member such that the actuation member is deformed relative to the engagement portion prior to moving the elongated member to cut the target sample.

16. The apparatus of claim 1, wherein the second notch surrounds a portion of the actuation member except for a connecting portion of the actuation member at a distal end of the actuation member connecting the actuation member to the retention member.

17. An apparatus, comprising:

an elongated member comprising a cutting portion and a side wall, the cutting portion being configured to cut a target sample when the elongated member is moved, and the side wall defining an internal volume within which at least a portion of the target sample can be received; and a retention member movably coupled to the elongated member, the retention member comprising an engagement portion and an actuation member;

wherein the actuation member of the retention member is configured to be coupled to an actuator;

the engagement portion of the retention member moves between a first position and a second position as the retention member is actuated by the actuator;

the engagement portion at the second position exerts a force on the target sample within the internal volume;

the side wall comprises a first notch that surrounds a portion of the retention member such that only a proximal end portion of the retention member is directly coupled to the side wall; and the retention member comprises a second notch that surrounds a portion of the actuation member.

\* \* \* \* \*